United States Patent
Chyu et al.

(10) Patent No.: US 9,221,876 B2
(45) Date of Patent: Dec. 29, 2015

(54) METHODS FOR TREATING KIDNEY DISEASE WITH FRAGMENTS OF APOB-100

(71) Applicant: Cedars-Sinai Medical Center, Los Angeles, CA (US)

(72) Inventors: Kuang-Yuh Chyu, Los Angeles, CA (US); Prediman K. Shah, Los Angeles, CA (US); Paul Dimayuga, Burbank, CA (US)

(73) Assignee: CardioVax, LLC, Torrance, CA (US)

( * ) Notice: Subject to any disclaimer, the term of this patent is extended or adjusted under 35 U.S.C. 154(b) by 0 days.

(21) Appl. No.: 14/357,204

(22) PCT Filed: Nov. 6, 2012

(86) PCT No.: PCT/US2012/063705
§ 371 (c)(1),
(2) Date: May 8, 2014

(87) PCT Pub. No.: WO2013/070603
PCT Pub. Date: May 16, 2013

(65) Prior Publication Data
US 2014/0308306 A1 Oct. 16, 2014

Related U.S. Application Data

(60) Provisional application No. 61/558,908, filed on Nov. 11, 2011.

(51) Int. Cl.
| | |
|---|---|
| A61P 13/12 | (2006.01) |
| A61K 38/10 | (2006.01) |
| C07K 7/08 | (2006.01) |
| C07K 14/775 | (2006.01) |
| A61K 38/17 | (2006.01) |
| A61K 39/00 | (2006.01) |
| A61K 35/17 | (2015.01) |

(52) U.S. Cl.
CPC . *C07K 7/08* (2013.01); *A61K 35/17* (2013.01); *A61K 38/10* (2013.01); *A61K 38/1709* (2013.01); *A61K 39/0012* (2013.01); *C07K 14/775* (2013.01); *A61K 2039/55505* (2013.01); *A61K 2039/6081* (2013.01)

(58) Field of Classification Search
None
See application file for complete search history.

(56) References Cited

U.S. PATENT DOCUMENTS

| | | | |
|---|---|---|---|
| 7,544,360 B2 * | 6/2009 | Nilsson et al. ............. | 424/185.1 |
| 2009/0093066 A1 | 4/2009 | Blackshear | |
| 2011/0256134 A1 | 10/2011 | Bunting et al. | |

FOREIGN PATENT DOCUMENTS

| | | |
|---|---|---|
| EP | 2788012 | 10/2014 |
| WO | WO2011060329 | 5/2011 |
| WO | 2012065135 A2 | 5/2012 |
| WO | 2012074725 A2 | 6/2012 |
| WO | WO2013070603 | 5/2013 |

OTHER PUBLICATIONS

Wells (1990) Biochemistry 29(37): 8509-8517.*
Ngo et al (1994) "The Protein Folding Problem and Tertiary Structure Prediction, Chapter 14: Computational Complexity Protein Structure Prediction, and the Levinthal Paradox" pp. 433-440 and 492-495 only.*
Bork (2000) Genome Research 10:398.*
Skolnick et al (2000) Trends in Biotech. 18(1): 34.*
Doerks et al (1998) Trends in Genetics 14(6): 248.*
Brenner (1999) Trends in Genetics 15(4): 132.*
Luke, 1999. Nephrol Dial Transplant. 14: 2271-2278.*
Chyu et al, 2005. Biochem Biophys Res Comm. 338: 1982-1989.*
ISR for PCT/US2012/063705, 3 pages.
Written Opinion for PCT/US2012/063705, 7 pages.
IPRP for PCT/US2012/063705, 1 page.
EP Application No. 12847583.7 Extended Search Report dated Jul. 3, 2015; 9 pages.
Chyu et al. CD8+T Cells Mediate the Athero-Protective Effect of Immunization with an ApoB-100 Peptide. PLoS One (2012). 7(2): e30780, 12 pages.
Honjo et al. ApoB-100 Related Peptide Vaccine Reduces Hypertension and Mortality in a Model of Angiotensin II-Induced Aortic Aneurysm in Apo E (-/-) Mice: A Novel Therapeutic Paradigm. Circulation (2011). 124(21), Suppl S. Abstract Only.
Honjo et al. ApoB-100 Related Peptide Immunization Confers Protection Against Angiotension II-induced Renal Inflammatory Responses. Circulation (2012). 126(21), Suppl S. Abstract Only.
Honjo et al. CD8+T Cells Elicited by an ApoB-100 Related Peptide Vaccine Mediate Protection Against Angiotension II-induced Hypertension and Renal Fibrosis. Hypertension (2013). 62(3), Suppl S. Abstract Only.
Zhao et al. Athero-protective Effects of Immunization with apoB-100 Related Peptide Vaccine in apoE-/-Mice is Associated with Enhanced CD8 Regulatory T Cell Response. Circulation (2009). 120(18), Suppl 2. Abstract Only.

* cited by examiner

*Primary Examiner* — Zachary Howard
(74) *Attorney, Agent, or Firm* — Nixon Peabody LLP; Seth Levy; Hema Vakharia-Rao

(57) ABSTRACT

The invention provides compositions comprising immunogenic fragments of ApoB-100 for eliciting an immune response in a subject or vaccinating a subject, so as to treat, prevent, 5 inhibit and/or reduce symptoms of kidney diseases in the subject. The compositions include immunogenic fragments of ApoB-100, CD8+ T cells activated with immunogenic fragments of ApoB-100 or a combination thereof.

15 Claims, 4 Drawing Sheets

METHODS FOR TREATING KIDNEY DISEASE WITH FRAGMENTS OF APOB-100

CROSS-REFERENCE TO RELATED APPLICATIONS

This application is the National Phase of International Application PCT/US2012/063705, filed Nov. 6, 2012, which designated the U.S. and that International Application was published under PCT Article 21(2) in English. The present application also claims the benefit of the filing date of U.S. Provisional Application No. 61/558,908 filed Nov. 11, 2011, the disclosures of each of which are incorporated herein by reference in their entirety.

FIELD OF INVENTION

The invention provides compositions and methods for treating kidney diseases in a subject in need thereof. The compositions include one or more peptides of ApoB-100 as set forth in Table 1 and/or derivatives, peptidomimetics, pharmaceutical equivalents and/or analogs thereof.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The renin-angiotensin system (RAS) or the renin-angiotensin-aldosterone system (RAAS) is a hormone system that regulates blood pressure and fluid balance and is activated when there is a drop in blood volume or blood pressure. When the blood volume is low, renin is secreted into the plasma by the juxtaglomerular cells of the kidneys. The plasma renin carries out the conversion of angiotensinogen released by the liver to angiotensin I (Kumar et al., 2010 "11". *Pathologic Basis of Disease* (Eighth ed.). Philadelphia: Saunders Elsevier. p. 493. ISBN 978-1-4160-3121-5). Angiotensin I (AngI) is then converted to angiotensin II (AngII) by the angiotensin converting enzyme (ACE) found in the lungs. AngII is a potent vaso-active peptide which causes blood vessels to constrict, resulting in increased blood pressure. AngII also stimulates the secretion of the hormone aldosterone from the adrenal cortex. Aldosterone causes the tubules of the kidneys to increase the reabsorption of sodium and water into the blood. This increases the volume of fluid in the body, which also increases blood pressure.

AngII activates at least two receptors, namely, angiotensin II type 1 ($AT_1$) and angiotensin II type II ($AT_2$). Majority of the effects of AngII, such as vasoconstriction, proteinuria, fibrosis and inflammation are mediated by the $AT_1$ receptor. Hypertension and proteinuria are the most important risk factors for the progression of renal disease. Haemodynamic and non-haemodynamic effects of angiotensin II are critically involved in the development and maintenance of hypertension and proteinuria. Therefore, suppression of angiotensin II formation by angiotensin-converting enzyme (ACE) inhibitors and blockade of $AT_1$ receptor by angiotensin II receptor blockers (ARB) are powerful therapeutic strategies that effectively slow the progression of renal disease by lowering blood pressure and proteinuria (Wenzel et al., *J Renin Angiotensin Aldosterone Syst*. 2010 March; 11(1):37-41. Epub 2009 Oct. 27; Wenzel U O, *Contrib Nephrol* 2001; 135:200-11). It has been speculated that the $AT_2$ receptor may exhibit beneficial effects (such as anti-proteinuric, anti-fibrotic and anti-inflammatory) and that the blockade of the $AT_1$ receptor results in increased synthesis of AngII which in turn stimulates the $AT_2$ receptor (Wenzel et al., *J Renin Angiotensin Aldosterone Syst*. 2010 March; 11(1):37-41. Epub 2009 Oct. 27).

The inventors observed that peptides of ApoB-100 reduce the levels of the $AT_1$ receptor and therefore these peptides serve as therapeutics in kidney diseases.

SUMMARY OF THE INVENTION

The invention provides composition comprising one or more peptides of ApoB-100 and/or derivatives, peptidomimetics, pharmaceutical equivalents and/or analogs thereof.

In one embodiment, the composition comprises one or more peptides of ApoB-100 and/or immunogenically active portions, derivatives, peptidomimetics, pharmaceutical equivalents and/or an analogs thereof and a pharmaceutically acceptable carrier that induces and/or enhances an immune response. The composition elicits an immune response and/or used for immunization. The composition further comprises a pharmaceutically acceptable carrier. In some embodiments, the carriers induce and/or enhance an immune response. In an embodiment, the peptide of ApoB-100 is any one or more of peptides P1 to P302 as set forth in Table 1. In a further embodiment, one or more of the peptides of ApoB-100 are immunogenic peptides of ApoB-100.

In another embodiment, the composition includes one or more peptides of ApoB-100 and/or derivatives, peptidomimetics, pharmaceutical equivalents and/or an analogs thereof and CD8+ T cells. The CD8+ T cells are activated by one or more immunogenic peptides of ApoB-100. The composition further comprises a pharmaceutically acceptable carrier. In some embodiments, the carrier induces and/or enhances an immune response. The CD8+ T cells may be autologous. In an embodiment, the peptide of ApoB-100 is any one or more of peptides P1 to P302 as set forth in Table 1. In a further embodiment, one or more of the peptides of ApoB-100 are immunogenic peptides of ApoB-100.

The compositions of invention may be used for treating kidney disease, inhibiting kidney disease, preventing kidney disease and/or promoting prophylaxis of kidney disease in a subject in need thereof. The methods for these indications include providing compositions that include one or more peptides of ApoB-100 and/or derivatives, peptidomimetics, pharmaceutical equivalents and/or analogs thereof, and administering an effective amount of the composition so as to treat, inhibit, prevent and/or promote prophylaxis of kidney disease in the subject.

BRIEF DESCRIPTION OF FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
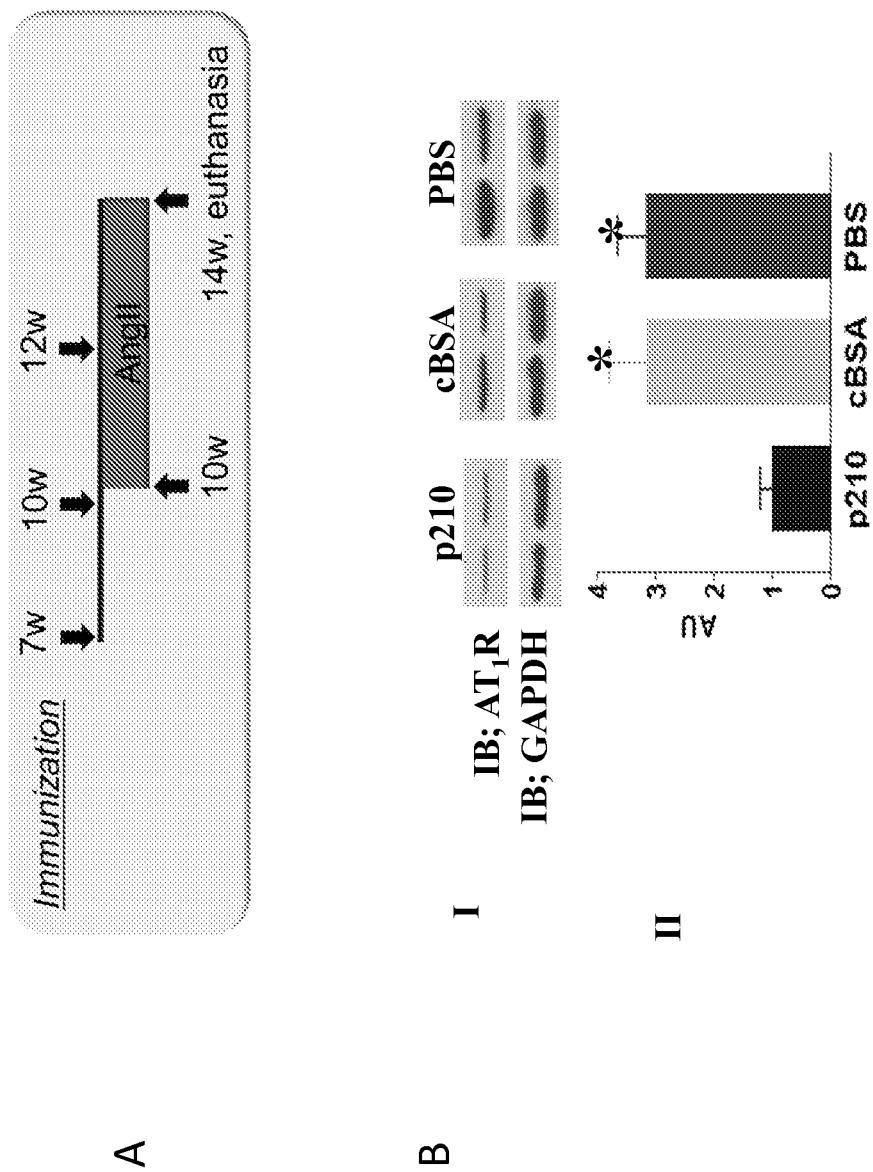
FIG. 1 depicts, in accordance with an embodiment of the invention, (A) a schematic showing the immunization schedule, and (B) that p210 significantly decreased the expression of $AT_1R$ in aorta, as assessed by Western blot analysis (I), from mice immunized with p210, adjuvant/carrier control or PBS after 4-weeks of angiotensin II infusion delivered by a subcutaneously implanted pump; (II) Densitometric analysis. *$p<0.05$ vs. p210 by ANOVA following post-hoc test. N=6 in each group. p210: immunized with p210/cBSA/Alum+AngII; cBSA: immunized with cBSA/Alum+AngII; PBS: immunized with PBS+AngII.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Peptidomimetic" as used herein is a small protein-like chain designed to mimic a peptide. They may be modifications of an existing peptide or newly designed to mimic known peptides. They may be, for example peptoids and/or β-peptides and/or D-peptides.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy.

"Conditions" and "disease conditions," as used herein may include, but are in no way limited to any form of kidney diseases.

"Kidney disease" as used herein refers to renal inflammatory response. In one embodiment, the renal inflammatory response is angiotensin II-induced renal inflammatory response. In various embodiments, kidney disease may be atherosclerosis-related, hypertension-related, diabetes and/or autoimmune diseases-related. Glomerular and renal dysfunction with resultant clinical or subclinical renal dysfunction is included in kidney diseases as used herein.

"Immunogenic fragment", "antigenic fragment" or "immunogenic peptides" as used herein indicates a portion of a polypeptide of any length capable of generating an immune response, such as an antigen. An antigen is a molecule recognized by the immune system. An antigenic fragment of ApoB100 is accordingly a portion of ApoB-100 that presents antigenic properties (e.g. a specific humoral or cellular response). "Immunogenic fragments" also refer to derivatives of any fragment of ApoB100, such as mutated fragments (including fragments with replaced, added or deleted residues), oxidative derivatives and/or peptides treated with MDA or copper, which maintain a detectable antigenic property of the original fragment.

"Immune response" as used herein refers to immunities including but not limited to innate immunity, humoral immunity, cellular immunity, immunity, inflammatory response, acquired (adaptive) immunity, autoimmunity and/or overactive immunity.

"T cells" as used herein refers to T lymphocytes belonging to a group of white blood cells (lymphocytes), and participate in humoral or cell-mediated immunity. T cells can be distinguished from other lymphocyte types, such as B cells and natural killer cells (NK cells) by the presence of specific markers on their cell surface such as T cell receptors (TCR). Additional markers identifying T cell include but are not limited to any one or more of CD1a, CD3, CD4, CD8, or a combination thereof and additional markers possibly associated to a T cell state and/or functionality as will be understood by a person of ordinary skill in the art.

"CD8(+) T cells" or "CD8+ T cells" as used herein refer to T cells expressing the CD8 glycoprotein on their cell surface, wherein the CD8 (cluster of differentiation 8) glycoprotein is a transmembrane glycoprotein that serves as a co-receptor for the T cell receptor (TCR). Similar to the TCR, CD8 binds to a major histocompatibility complex (MHC) molecule, but is specific for the class I MHC protein. Exemplary CD8+ T cells comprise cytotoxic memory CD8+ T cells, regulatory CD8+ T cells, cytotoxic effector CD8+ T-cells and additional cells identifiable by a person of ordinary skill in the art.

The terms "enhancer" and "enhance" as it pertains to a molecule in connection with CD8(+) T cell refers to the ability of a molecule to modify the immune response by promoting the activation of cells of the immune system. The choice of appropriate enhancer can allow control of activation of the immune response. Exemplary enhancers include cytokines such as IL-10, IL-2, IL-12, IL-4 and IL-16. The term "cytokine" as used herein refers cell signaling molecules that act as has immunomodulating agents, and comprise proteins such as interleukins and interferons as would be identifiable to a skilled person. Selection of a suitable cytokine can result under appropriate conditions in the preferential induction of a humoral or cellular immune response.

The terms "activated" and "activation" as used herein refers to the process by which a T cells interact with an antigen presenting cells which presents a specific antigen for a time and under condition resulting in a T cell having a pre-assigned immunological role (e.g. cytotoxicity) within the immune system. The term "antigen-presenting cell" (APC) indicates a cell that displays antigen complex with major histocompatibility complex (MHC) on its surface. T-cells recognize this complex using their T-cell receptor (TCR). Exemplary APCs comprise dendritic cells (DCs) which are known to play an important role in linking innate and acquired immunity (Chyu, K. et al., 2005. *Biochem.*

Biophys. Res. Commun. 338:1982-1989; Fredrikson, G. N., et al., 2003. Arterioscler. Thromb. Vasc. Biol. 23:879-884) and both immune responses participate in atherogenesis (Fredrikson, G. N., L. et al., 2005 Autoimmunity 38:171-179; Fredrikson, G. N., et al. 2008. J. Intern. Med. 1-8). In various embodiments, activated CD8(+) T cells according to the present disclosure are activated with one or more immunogenic fragment of ApoB100 or an immunogenically active portion thereof and are typically specific for the immunogenic fragment or the immunogenically active portion used for the activation.

"Fragment of ApoB100" as used herein refers not only to fragments/peptides of any length from ApoB100, but also peptides produced by genetic recombination or chemical synthesis, comprising sequences from ApoB100.

"Derivative" as used herein with reference to a first peptide (e.g., an immunogenic fragment), indicates a second peptide that is structurally related to the first peptide and is derivable from the first peptide by a modification that introduces a feature that is not present in the first peptide while retaining functional properties of the first peptide. A derivative peptide of an immunogenic fragment or of any portion thereof retains one or more of the immunogenic activities that are herein described in connection with an ApoB100 immunogenic fragment or portion thereof. The antigenic properties can be verified with methods and systems such as the ones already described for the immunogenic fragments and additional methods and systems identifiable to a skilled person. In an embodiment, a derivative of a peptide of ApoB-100 includes immunogenically active fragments of the peptides of ApoB-100 described herein.

"Immunogenically active portion" as used herein refers to any part of a reference antigen that can elicit a specific immune response. Exemplary immunogenically active portions are the epitopes typically formed by 5 or more residues included within an immunogenic fragment. In some embodiments, epitopes within one or more fragments can overlap. Immunogenic fragments can be expressed by recombinant technology, such as a fusion with an affinity or epitope tag, chemical synthesis of an oligopeptide, either free or conjugated to carrier proteins, or any other methods known in the art to express the ApoB-100 peptides.

Exemplary fragments of ApoB100 are peptides each comprising one of the sequences listed in the Sequence Listing as SEQ ID NO: 1 to SEQ ID NO: 302 described in further detail in the Examples section. Methods and systems suitable to identify an immunogenic fragment in the sense of the present are described in WO 02/080954, hereby incorporated by reference. In an embodiment, the one or more immunogenic fragments of ApoB100 suitable to treat, prevent and/or reduce kidney disease are associated to atherosclerosis reduction.

"Mammal" as used herein refers to any member of the class Mammalia, including, without limitation, humans and non-human primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented.

As discussed above, Applicants observe that peptides of ApoB-100 reduce the levels of the $AT_1$ receptor and therefore these peptides serve as therapeutics in kidney diseases.

Peptides of the Invention

Specific immunogenic epitopes of ApoB-100 were characterized and a peptide library including 302 peptides, each about 20 amino acid residues in length, covering the complete 4563 amino acid sequence of human ApoB-100 was produced. The peptides were produced with a 5 amino acid overlap to cover all sequences at break points. Peptides were numbered 1-302 starting at the N-terminal of ApoB-100 as indicated in Table 1 below.

TABLE 1

| Peptide | Sequence | Apolipoprotein B aa | SEQ ID NO |
|---|---|---|---|
| P1: | EEEML ENVSL VCPKD ATRFK | aa 1-20 | SEQ ID NO: 1 |
| P2: | ATRFK HLRKY TYNYE AESSS | aa 16-35 | SEQ ID NO: 2 |
| P3: | AESSS GVPGT ADSRS ATRIN | aa 31-50 | SEQ ID NO: 3 |
| P4: | ATRIN CKVEL EVPQL CSFIL | aa 46-65 | SEQ ID NO: 4 |
| P5: | CSFIL KTSQC TLKEV YGFNP | aa 61-80 | SEQ ID NO: 5 |
| P6: | YGFNP EGKAL LKKTK NSEEF | aa 76-95 | SEQ ID NO: 6 |
| P7: | NSEEF AAAMS RYELK LAIPE | aa 91-110 | SEQ ID NO: 7 |
| P8: | LAIPE GKQVF LYPEK DEPTY | aa 106-125 | SEQ ID NO: 8 |
| P9: | DEPTY ILNIK RGIIS ALLVP | aa 121-140 | SEQ ID NO: 9 |
| P10: | ALLVP PETEE AKQVL FLDTV | aa 136-155 | SEQ ID NO: 10 |
| P11: | FLDTV YGNCS THFTV KTRKG | aa 151-170 | SEQ ID NO: 11 |
| P12: | KTRKG NVATE ISTER DLGQC | aa 166-185 | SEQ ID NO: 12 |

TABLE 1-continued

| Peptide | Sequence | Apolipoprotein B aa | SEQ ID NO |
|---|---|---|---|
| P13: | DLGQC DRFKP IRTGI SPLAL | aa 181-200 | SEQ ID NO: 13 |
| P14: | SPLAL IKGMT RPLST LISSS | aa 196-215 | SEQ ID NO: 14 |
| P15: | LISSS QSCQY TLDAK RKHVA | aa 211-230 | SEQ ID NO: 15 |
| P16: | RKHVA EAICK EQHLF LPFSY | aa 226-245 | SEQ ID NO: 16 |
| P17: | LPFSY NNKYG MVAQV TQTLK | aa 241-260 | SEQ ID NO: 17 |
| P18: | TQTLK LEDTP KINSR FFGEG | aa 256-275 | SEQ ID NO: 18 |
| P19: | FFGEG TKKMG LAFES TKSTS | aa 271-290 | SEQ ID NO: 19 |
| P20: | TKSTS PPKQA EAVLK TLQEL | aa 286-305 | SEQ ID NO: 20 |
| P21: | TLQEL KKLTI SEQNI QRANL | aa 301-320 | SEQ ID NO: 21 |
| P22: | QRANL FNKLV TELRG LSDEA | aa 316-335 | SEQ ID NO: 22 |
| P23: | LSDEA VTSLL PQLIE VSSPI | aa 331-350 | SEQ ID NO: 23 |
| P24: | VSSPI TLQAL VQCGQ PQCST | aa 346-365 | SEQ ID NO: 24 |
| P25: | PQCST HILQW LKRVH ANPLL | aa 361-380 | SEQ ID NO: 25 |
| P26: | ANPLL IDVVT YLVAL IPEPS | aa 376-395 | SEQ ID NO: 26 |
| P27: | IPEPS AQQLR EIFNM ARDQR | aa 391-410 | SEQ ID NO: 27 |
| P28: | ARDQR SRATL YALSH AVNNY | aa 406-425 | SEQ ID NO: 28 |
| P29: | AVNNY HKTNP TGTQE LLDIA | aa 421-440 | SEQ ID NO: 29 |
| P30: | LLDIA NYLME QIQDD CTGDE | aa 436-455 | SEQ ID NO: 30 |
| P31: | CTGDE DYTYL ILRVI GNMGQ | aa 451-470 | SEQ ID NO: 31 |
| P32: | GNMGQ TMEQL TPELK SSILK | aa 466-485 | SEQ ID NO: 32 |
| P33: | SSILK CVQST KPSLM IQKAA | aa 481-500 | SEQ ID NO: 33 |
| P34: | IQKAA IQALR KMEPK DKDQE | aa 496-515 | SEQ ID NO: 34 |
| P35: | DKDQE VLLQT FLDDA SPGDK | aa 511-530 | SEQ ID NO: 35 |
| P36: | SPGDK RLAAY LMLMR SPSQA | aa 526-545 | SEQ ID NO: 36 |
| P37: | SPSQA DINKI VQILP WEQNE | aa 541-560 | SEQ ID NO: 37 |
| P38: | WEQNE QVKNF VASHI ANILN | aa 556-575 | SEQ ID NO: 38 |
| P39: | ANILN SEELD IQDLK KLVKE | aa 571-590 | SEQ ID NO: 39 |
| P40: | KLVKE ALKES QLPTV MDFRK | aa 586-605 | SEQ ID NO: 40 |
| P41: | MDFRK FSRNY QLYKS VSLPS | aa 601-620 | SEQ ID NO: 41 |
| P42: | VSLPS LDPAS AKIEG NLIFD | aa 616-635 | SEQ ID NO: 42 |
| P43: | NLIFD PNNYL PKESM LKTTL | aa 631-650 | SEQ ID NO: 43 |
| P44: | LKTTL TAFGF ASADL IEIGL | aa 646-665 | SEQ ID NO: 44 |
| P45: | IEIGL EGKGF EPTLE ALFGK | aa 661-680 | SEQ ID NO: 45 |
| P46: | ALFGK QGFFP DSVNK ALYWV | aa 676-695 | SEQ ID NO: 46 |
| P47: | ALYWV NGQVP DGVSK VLVDH | aa 691-710 | SEQ ID NO: 47 |
| P48: | VLVDH FGYTK DDKHE QDMVN | aa 706-725 | SEQ ID NO: 48 |
| P49: | QDMVN GIMLS VEKLI KDLKS | aa 721-740 | SEQ ID NO: 49 |
| P50: | KDLKS KEVPE ARAYL RILGE | aa 736-755 | SEQ ID NO: 50 |
| P51: | RILGE ELGFA SLHDL QLLGK | aa 751-770 | SEQ ID NO: 51 |

TABLE 1-continued

| Peptide | Sequence | Apolipoprotein B aa | SEQ ID NO |
|---|---|---|---|
| P52: | QLLGK LLLMG ARTLQ GIPQM | aa 766-785 | SEQ ID NO: 52 |
| P53: | GIPQM IGEVI RKGSK NDFFL | aa 781-800 | SEQ ID NO: 53 |
| P54: | NDFFL HYIFM ENAFE LPTGA | aa 796-815 | SEQ ID NO: 54 |
| P55: | LPTGA GLQLQ ISSSG VIAPG | aa 811-830 | SEQ ID NO: 55 |
| P56: | VIAPG AKAGV KLEVA NMQAE | aa 826-845 | SEQ ID NO: 56 |
| P57: | NMQAE LVAKP SVSVE FVTNM | aa 841-860 | SEQ ID NO: 57 |
| P58: | FVTNM GIIIP DFARS GVQMN | aa 856-875 | SEQ ID NO: 58 |
| P59: | GVQMN TNFFH ESGLE AHVAL | aa 871-890 | SEQ ID NO: 59 |
| P60: | AHVAL KAGKL KFIIP SPKRP | aa 886-905 | SEQ ID NO: 60 |
| P61: | SPKRP VKLLS GGNTL HLVST | aa 901-920 | SEQ ID NO: 61 |
| P62: | HLVST TKTEV IPPLI ENRQS | aa 916-935 | SEQ ID NO: 62 |
| P63: | ENRQS WSVCK QVFPG LNYCT | aa 931-950 | SEQ ID NO: 63 |
| P64: | LNYCT SGAYS NASST DSASY | aa 946-965 | SEQ ID NO: 64 |
| P65: | DSASY YPLTG DTRLE LELRP | aa 961-980 | SEQ ID NO: 65 |
| P66: | LELRP TGEIE QYSVS ATYEL | aa 976-995 | SEQ ID NO: 66 |
| P67: | ATYEL QREDR ALVDT LKFVT | aa 991-1010 | SEQ ID NO: 67 |
| P68: | LKFVT QAEGA KQTEA TMTFK | aa 1006-1025 | SEQ ID NO: 68 |
| P69: | TMTFK YNRQS MTLSS EVQIP | aa 1021-1040 | SEQ ID NO: 69 |
| P70: | EVQIP DFDVD LGTIL RVNDE | aa 1036-1055 | SEQ ID NO: 70 |
| P71: | RVNDE STEGK TSYRL TLDIQ | aa 1051-1070 | SEQ ID NO: 71 |
| P72: | TLDIQ NKKIT EVALM GHLSC | aa 1066-1085 | SEQ ID NO: 72 |
| P73: | GHLSC DTKEE RKIKG VISIP | aa 1081-1100 | SEQ ID NO: 73 |
| P74: | VISIP RLQAE ARSEI LAHWS | aa 1096-1115 | SEQ ID NO: 74 |
| P75: | LAHWS PAKLL LQMDS SATAY | aa 1111-1130 | SEQ ID NO: 75 |
| P76: | SATAY GSTVS KRVAW HYDEE | aa 1126-1145 | SEQ ID NO: 76 |
| P77: | HYDEE KIEFE WNTGT NVDTK | aa 1141-1160 | SEQ ID NO: 77 |
| P78: | NVDTK KMTSN FPVDL SDYPK | aa 1156-1175 | SEQ ID NO: 78 |
| P79: | SDYPK SLHMY ANRLL DHRVP | aa 1171-1190 | SEQ ID NO: 79 |
| P80: | DHRVP ETDMT FRHVG SKLIV | aa 1186-1205 | SEQ ID NO: 80 |
| P81: | SKLIV AMSSW LQKAS GSLPY | aa 1201-1220 | SEQ ID NO: 81 |
| P82: | GSLPY TQTLQ DHLNS LKEFN | aa 1216-1235 | SEQ ID NO: 82 |
| P83: | LKEFN LQNMG LPDFH IPENL | aa 1231-1250 | SEQ ID NO: 83 |
| P84: | IPENL FLKSD GRVKY TLNKN | aa 1246-1260 | SEQ ID NO: 84 |
| P85: | TLNKN SLKIE IPLPF GGKSS | aa 1261-1280 | SEQ ID NO: 85 |
| P86: | GGKSS RDLKM LETVR TPALH | aa 1276-1295 | SEQ ID NO: 86 |
| P87: | TPALH FKSVG FHLPS REFQV | aa 1291-1310 | SEQ ID NO: 87 |
| P88: | REFQV PTFTI PKLYQ LQVPL | aa 1306-1325 | SEQ ID NO: 88 |
| P89: | LQVPL LGVLD LSTNV YSNLY | aa 1321-1340 | SEQ ID NO: 89 |
| P90: | YSNLY NWSAS YSGGN TSTDH | aa 1336-1355 | SEQ ID NO: 90 |

TABLE 1-continued

| Peptide | Sequence | Apolipoprotein B aa | SEQ ID NO |
|---|---|---|---|
| P91: | TSTDH FSLRA RYHMK ADSVV | aa 1351-1370 | SEQ ID NO: 91 |
| P92: | ADSVV DLLSY NVQGS GETTY | aa 1366-1385 | SEQ ID NO: 92 |
| P93: | GETTY DHKNT FTLSC DGSLR | aa 1381-1400 | SEQ ID NO: 93 |
| P94: | DGSLR HKFLD SNIKF SHVEK | aa 1396-1415 | SEQ ID NO: 94 |
| P95: | SHVEK LGNNP VSKGL LIFDA | aa 1411-1430 | SEQ ID NO: 95 |
| P96: | LIFDA SSSWG PQMSA SVHLD | aa 1426-1445 | SEQ ID NO: 96 |
| P97: | SVHLD SKKKQ HLFVK EVKID | aa 1441-1460 | SEQ ID NO: 97 |
| P98: | EVKID GQFRV SSFYA KGTYG | aa 1456-1475 | SEQ ID NO: 98 |
| P99: | KGTYG LSCQR DPNTG RLNGE | aa 1471-1490 | SEQ ID NO: 99 |
| P100: | RLNGE SNLRF NSSYL QGTNQ | aa 1486-1505 | SEQ ID NO: 100 |
| P101: | QGTNQ ITGRY EDGTL SLTST | aa 1501-1520 | SEQ ID NO: 101 |
| P102: | SLTST SDLQS GIIKN TASLK | aa 1516-1535 | SEQ ID NO: 102 |
| P103: | TASLK YENYE LTLKS DTNGK | aa 1531-1550 | SEQ ID NO: 103 |
| P104: | DTNGK YKNFA TSNKM DMTFS | aa 1546-1565 | SEQ ID NO: 104 |
| P105: | DMTFS KQNAL LRSEY QADYE | aa 1561-1580 | SEQ ID NO: 105 |
| P106: | QADYE SLRFF SLLSG SLNSH | aa 1576-1595 | SEQ ID NO: 106 |
| P107: | SLNSH GLELN ADILG TDKIN | aa 1591-1610 | SEQ ID NO: 107 |
| P108: | TDKIN SGAHK ATLRI GQDGI | aa 1606-1625 | SEQ ID NO: 108 |
| P109: | GQDGI STSAT TNLKC SLLVL | aa 1621-1640 | SEQ ID NO: 109 |
| P110: | SLLVL ENELN AELGL SGASM | aa 1636-1655 | SEQ ID NO: 110 |
| P111: | SGASM KLTTN GRFRE HNAKF | aa 1651-1670 | SEQ ID NO: 111 |
| P112: | HNAKF SLDGK AALTE LSLGS | aa 1666-1685 | SEQ ID NO: 112 |
| P113: | LSLGS AYQAM ILGVD SKNIF | aa 1681-1700 | SEQ ID NO: 113 |
| P114: | SKNIF NFKVS QEGLK LSNDM | aa 1696-1715 | SEQ ID NO: 114 |
| P115: | LSNDM MGSYA EMKFD HTNSL | aa 1711-1730 | SEQ ID NO: 115 |
| P116: | HTNSL NIAGL SLDFS SKLDN | aa 1726-1745 | SEQ ID NO: 116 |
| P117: | SKLDN IYSSD KFYKQ TVNLQ | aa 1741-1760 | SEQ ID NO: 117 |
| P118: | TVNLQ LQPYS LVTTL NSDLK | aa 1756-1775 | SEQ ID NO: 118 |
| P119: | NSDLK YNALD LTNNG KLRLE | aa 1771-1790 | SEQ ID NO: 119 |
| P120: | KLRLE PLKLH VAGNL KGAYQ | aa 1786-1805 | SEQ ID NO: 120 |
| P121: | KGAYQ NNEIK HIYAI SSAAL | aa 1801-1820 | SEQ ID NO: 121 |
| P122: | SSAAL SASYK ADTVA KVQGV | aa 1816-1835 | SEQ ID NO: 122 |
| P123: | KVQGV EFSHR LNTDI AGLAS | aa 1831-1850 | SEQ ID NO: 123 |
| P124: | AGLAS AIDMS TNYNS DSLHF | aa 1846-1865 | SEQ ID NO: 124 |
| P125: | DSLHF SNVFR SVMAP FTMTI | aa 1861-1880 | SEQ ID NO: 125 |
| P126: | FTMTI DAHTN GNGKL ALWGE | aa 1876-1895 | SEQ ID NO: 126 |
| P127: | ALWGE HTGQL YSKFL LKAEP | aa 1891-1910 | SEQ ID NO: 127 |
| P128: | LKAEP LAFTF SHDYK GSTSH | aa 1906-1925 | SEQ ID NO: 128 |
| P129: | GSTSH HLVSR KSISA ALEHK | aa 1921-1940 | SEQ ID NO: 129 |

TABLE 1-continued

| Peptide | Sequence | Apolipoprotein B aa | SEQ ID NO |
|---|---|---|---|
| P130: | ALEHK VSALL TPAEQ TGTWK | aa 1936-1955 | SEQ ID NO: 130 |
| P131: | TGTWK LKTQF NNNEY SQDLD | aa 1951-1970 | SEQ ID NO: 131 |
| P132: | SQDLD AYNTK DKIGV ELTGR | aa 1966-1985 | SEQ ID NO: 132 |
| P133: | ELTGR TLADL TLLDS PIKVP | aa 1981-2000 | SEQ ID NO: 133 |
| P134: | PIKVP LLLSE PINII DALEM | aa 1996-2015 | SEQ ID NO: 134 |
| P135: | DALEM RDAVE KPQEF TIVAF | aa 2011-2030 | SEQ ID NO: 135 |
| P136: | TIVAF VKYDK NQDVH SINLP | aa 2026-2045 | SEQ ID NO: 136 |
| P137: | SINLP FFETL QEYFE RNRQT | aa 2041-2060 | SEQ ID NO: 137 |
| P138: | RNRQT IIVVV ENVQR NLKHI | aa 2056-2075 | SEQ ID NO: 138 |
| P139: | NLKHI NIDQF VRKYR AALGK | aa 2071-2090 | SEQ ID NO: 139 |
| P140: | AALGK LPQQA NDYLN SFNWE | aa 2086-2105 | SEQ ID NO: 140 |
| P141: | SFNWE RQVSH AKEKL TALTK | aa 2101-2120 | SEQ ID NO: 141 |
| P142: | TALTK KYRIT ENDIQ IALDD | aa 2116-2135 | SEQ ID NO: 142 |
| P143: | IALDD AKINF NEKLS QLQTY | aa 2131-2150 | SEQ ID NO: 143 |
| P144: | QLQTY MIQFD QYIKD SYDLH | aa 2146-2165 | SEQ ID NO: 144 |
| P145: | SYDLH DLKIA IANII DEIIE | aa 2161-2180 | SEQ ID NO: 145 |
| P146: | DEIIE KLKSL DEHYH IRVNL | aa 2176-2195 | SEQ ID NO: 146 |
| P147: | IRVNL VKTIH DLHLF IENID | aa 2191-2210 | SEQ ID NO: 147 |
| P148: | IENID FNKSG SSTAS WIQNV | aa 2206-2225 | SEQ ID NO: 148 |
| P149: | WIQNV DTKYQ IRIQI QEKLQ | aa 2221-2240 | SEQ ID NO: 149 |
| P150: | QEKLQ QLKRH IQNID IQHLA | aa 2236-2255 | SEQ ID NO: 150 |
| P151: | IQHLA GKLKQ HIEAI DVRVL | aa 2251-2270 | SEQ ID NO: 151 |
| P152: | DVRVL LDQLG TTISF ERIND | aa 2266-2285 | SEQ ID NO: 152 |
| P153: | ERIND VLEHV KHFVI NLIGD | aa 2281-2300 | SEQ ID NO: 153 |
| P154: | NLIGD FEVAE KINAF RAKVH | aa 2296-2315 | SEQ ID NO: 154 |
| P155: | RAKVH ELIER YEVDQ QIQVL | aa 2311-2330 | SEQ ID NO: 155 |
| P156: | QIQVL MDKLV ELTHQ YKLKE | aa 2326-2345 | SEQ ID NO: 156 |
| P157: | YKLKE TIQKL SNVLQ QVKIK | aa 2341-2360 | SEQ ID NO: 157 |
| P158: | QVKIK DYFEK LVGFI DDAVK | aa 2356-2375 | SEQ ID NO: 158 |
| P159: | DDAVK KLNEL SFKTF IEDVN | aa 2371-2390 | SEQ ID NO: 159 |
| P160: | IEDVN KFLDM LIKKL KSFDY | aa 2386-2405 | SEQ ID NO: 160 |
| P161: | KSFDY HQFVD ETNDK IREVT | aa 2401-2420 | SEQ ID NO: 161 |
| P162: | IREVT QRLNG EIQAL ELPQK | aa 2416-2435 | SEQ ID NO: 162 |
| P163: | ELPQK AEALK LFLEE TKATV | aa 2431-2450 | SEQ ID NO: 163 |
| P164: | TKATV AVYLE SLQDT KITLI | aa 2446-2465 | SEQ ID NO: 164 |
| P165: | KITLI INWLQ EALSS ASLAH | aa 2461-2480 | SEQ ID NO: 165 |
| P166: | ASLAH MKAKF RETLE DTRDR | aa 2476-2495 | SEQ ID NO: 166 |
| P167: | DTRDR MYQMD IQQEL QRYLS | aa 2491-2510 | SEQ ID NO: 167 |
| P168: | QRYLS LVGQV YSTLV TYISD | aa 2506-2515 | SEQ ID NO: 168 |

TABLE 1-continued

| Peptide | Sequence | Apolipoprotein B aa | SEQ ID NO |
|---|---|---|---|
| P169: | TYISD WWTLA AKNLT DFAEQ | aa 2521-2540 | SEQ ID NO: 169 |
| P170: | DFAEQ YSIQD WAKRM KALVE | aa 2536-2555 | SEQ ID NO: 170 |
| P171: | KALVE QGFTV PEIKT ILGTM | aa 2551-2570 | SEQ ID NO: 171 |
| P172: | ILGTM PAFEV SLQAL QKATF | aa 2566-2585 | SEQ ID NO: 172 |
| P173: | QKATF QTPDF IVPLT DLRIP | aa 2581-2600 | SEQ ID NO: 173 |
| P174: | DLRIP SVQIN FKDLK NIKIP | aa 2596-2615 | SEQ ID NO: 174 |
| P175: | NIKIP SRFST PEFTI LNTFH | aa 2611-2630 | SEQ ID NO: 175 |
| P176: | LNTFH IPSFT IDFVE MKVKI | aa 2626-2645 | SEQ ID NO: 176 |
| P177: | MKVKI IRTID QMQNS ELQWP | aa 2641-2660 | SEQ ID NO: 177 |
| P178: | ELQWP VPDIY LRDLK VEDIP | aa 2656-2675 | SEQ ID NO: 178 |
| P179: | VEDIP LARIT LPDFR LPEIA | aa 2671-2690 | SEQ ID NO: 179 |
| P180: | LPEIA IPEFI IPTLN LNDFQ | aa 2686-2705 | SEQ ID NO: 180 |
| P181: | LNDFQ VPDLH IPEFQ LPHIS | aa 2701-2720 | SEQ ID NO: 181 |
| P182: | LPHIS HTIEV PTFGK LYSIL | aa 2716-2735 | SEQ ID NO: 182 |
| P183: | LYSIL KIQSP LFTLD ANADI | aa 2731-2750 | SEQ ID NO: 183 |
| P184: | ANADI GNGTT SANEA GIAAS | aa 2746-2765 | SEQ ID NO: 184 |
| P185: | GIAAS ITAKG ESKLE VLNFD | aa 2761-2780 | SEQ ID NO: 185 |
| P186: | VLNFD FQANA QLSNP KINPL | aa 2776-2795 | SEQ ID NO: 186 |
| P187: | KINPL ALKES VKFSS KYLRT | aa 2791-2810 | SEQ ID NO: 187 |
| P188: | KYLRT EHGSE MLFFG NAIEG | aa 2806-2825 | SEQ ID NO: 188 |
| P189: | NAIEG KSNTV ASLHT EKNTL | aa 2821-2840 | SEQ ID NO: 189 |
| P190: | EKNTL ELSNG VIVKI NNQLT | aa 2836-2855 | SEQ ID NO: 190 |
| P191: | NNQLT LDSNT KYFHK LNIPK | aa 2851-2870 | SEQ ID NO: 191 |
| P192: | LNIPK LDFSS QADLR NEIKT | aa 2866-2885 | SEQ ID NO: 192 |
| P193: | NEIKT LLKAG HIAWT SSGKG | aa 2881-2900 | SEQ ID NO: 193 |
| P194: | SSGKG SWKWA CPRFS DEGTH | aa 2896-2915 | SEQ ID NO: 194 |
| P195: | DEGTH ESQIS FTIEG PLTSF | aa 2911-2930 | SEQ ID NO: 195 |
| P196: | PLTSF GLSNK INSKH LRVNQ | aa 2926-2945 | SEQ ID NO: 196 |
| P197: | LRVNQ NLVYE SGSLN FSKLE | aa 2941-2960 | SEQ ID NO: 197 |
| P198: | FSKLE IQSQV DSQHV GHSVL | aa 2956-2975 | SEQ ID NO: 198 |
| P199: | GHSVL TAKGM ALFGE GKAEF | aa 2971-2990 | SEQ ID NO: 199 |
| P200: | GKAEF TGRHD AHLNG KVIGT | aa 2986-3005 | SEQ ID NO: 200 |
| P201: | KVIGT LKNSL FFSAQ PFEIT | aa 3001-3020 | SEQ ID NO: 201 |
| P202: | PFEIT ASTNN EGNLK VRFPL | aa 3016-3035 | SEQ ID NO: 202 |
| P203: | VRFPL RLTGK IDFLN NYALF | aa 3031-3050 | SEQ ID NO: 203 |
| P204: | NYALF LSPSA QQASW QVSAR | aa 3046-3065 | SEQ ID NO: 204 |
| P205: | QVSAR FNQYK YNQNF SAGNN | aa 3061-3080 | SEQ ID NO: 205 |
| P206: | SAGNN ENIME AHVGI NGEAN | aa 3076-3095 | SEQ ID NO: 206 |
| P207: | NGEAN LDFLN IPLTI PEMRL | aa 3091-3110 | SEQ ID NO: 207 |

TABLE 1-continued

| Peptide | Sequence | Apolipoprotein B aa | SEQ ID NO |
|---|---|---|---|
| P208: | PEMRL PYTII TTPPL KDFSL | aa 3106-3125 | SEQ ID NO: 208 |
| P209: | KDFSL WEKTG LKEFL KTTKQ | aa 3121-3140 | SEQ ID NO: 209 |
| P210: | KTTKQ SFDLS VKAQY KKNKH | aa 3136-3155 | SEQ ID NO: 210 |
| P211: | KKNKH RHSIT NPLAV LCEFI | aa 3151-3170 | SEQ ID NO: 211 |
| P212: | LCEFI SQSIK SFDRH FEKNR | aa 3166-3185 | SEQ ID NO: 212 |
| P213: | FEKNR NNALD FVTKS YNETK | aa 3181-3200 | SEQ ID NO: 213 |
| P214: | YNETK IKFDK YKAEK SHDEL | aa 3196-3215 | SEQ ID NO: 214 |
| P215: | SHDEL PRTFQ IPGYT VPVVN | aa 3211-3230 | SEQ ID NO: 215 |
| P216: | VPVVN VEVSP FTIEM SAFGY | aa 3226-3245 | SEQ ID NO: 216 |
| P217: | SAFGY VFPKA VSMPS FSILG | aa 3241-3260 | SEQ ID NO: 217 |
| P218: | FSILG SDVRV PSYTL ILPSL | aa 3256-3275 | SEQ ID NO: 218 |
| P219: | ILPSL ELPVL HVPRN LKLSL | aa 3271-3290 | SEQ ID NO: 219 |
| P220: | LKLSL PHFKE LCTIS HIFIP | aa 3286-3305 | SEQ ID NO: 220 |
| P221: | HIFIP AMGNI TYDFS FKSSV | aa 3301-3320 | SEQ ID NO: 221 |
| P222: | FKSSV ITLNT NAELF NQSDI | aa 3316-3335 | SEQ ID NO: 222 |
| P223: | NQSDI VAHLL SSSSS VIDAL | aa 3331-3350 | SEQ ID NO: 223 |
| P224: | VIDAL QYKLE GTTRL TRKRG | aa 3346-3365 | SEQ ID NO: 224 |
| P225: | TRKRG LKLAT ALSLS NKFVE | aa 3361-3380 | SEQ ID NO: 225 |
| P226: | NKFVE GSHNS TVSLT TKNME | aa 3376-3395 | SEQ ID NO: 226 |
| P227: | TKNME VSVAK TTKAE IPILR | aa 3391-3410 | SEQ ID NO: 227 |
| P228: | IPILR MNFKQ ELNGN TKSKP | aa 3406-3425 | SEQ ID NO: 228 |
| P229: | TKSKP TVSSS MEFKY DFNSS | aa 3421-3440 | SEQ ID NO: 229 |
| P230: | DFNSS MLYST AKGAV DHKLS | aa 3436-3455 | SEQ ID NO: 230 |
| P231: | DHKLS LESLT SYFSI ESSTK | aa 3451-3470 | SEQ ID NO: 231 |
| P232: | ESSTK GDVKG SVLSR EYSGT | aa 3466-3485 | SEQ ID NO: 232 |
| P233: | EYSGT IASEA NTYLN SKSTR | aa 3481-3500 | SEQ ID NO: 233 |
| P234: | SKSTR SSVKL QGTSK IDDIW | aa 3496-3515 | SEQ ID NO: 234 |
| P235: | IDDIW NLEVK ENFAG EATLQ | aa 3511-3530 | SEQ ID NO: 235 |
| P236: | EATLQ RIYSL WEHST KNHLQ | aa 3526-3545 | SEQ ID NO: 236 |
| P237: | KNHLQ LEGLF TNGE HTSKA | aa 3541-3560 | SEQ ID NO: 237 |
| P238: | HTSKA TLELS PWQMS ALVQV | aa 3556-3575 | SEQ ID NO: 238 |
| P239: | ALVQV HASQP SSFHD FPDLG | aa 3571-3590 | SEQ ID NO: 239 |
| P240: | FPDLG QEVAL NANTK NQKIR | aa 3586-3605 | SEQ ID NO: 240 |
| P241: | NQKIR WKNEV RIHSG SFQSQ | aa 3601-3620 | SEQ ID NO: 241 |
| P242: | SFQSQ VELSN DQEKA HLDIA | aa 3616-3635 | SEQ ID NO: 242 |
| P243: | HLDIA GSLEG HLRFL KNIIL | aa 3631-3650 | SEQ ID NO: 243 |
| P244: | KNIIL PVYDK SLWDF LKLDV | aa 3646-3665 | SEQ ID NO: 244 |
| P245: | LKLDV TTSIG RRQHL RVSTA | aa 3661-3680 | SEQ ID NO: 245 |
| P246: | RVSTA FVYTK NPNGY SFSIP | aa 3676-3695 | SEQ ID NO: 246 |

TABLE 1-continued

| Peptide | Sequence | Apolipoprotein B aa | SEQ ID NO |
|---|---|---|---|
| P247: | SFSIP VKVLA DKFIT PGLKL | aa 3691-3710 | SEQ ID NO: 247 |
| P248: | PGLKL NDLNS VLVMP TFHVP | aa 3706-3725 | SEQ ID NO: 248 |
| P249: | TFHVP FTDLQ VPSCK LDFRE | aa 3721-3740 | SEQ ID NO: 249 |
| P250: | LDFRE IQIYK KLRTS SFALN | aa 3736-3755 | SEQ ID NO: 250 |
| P251: | SFALN LPTLP EVKFP EVDVL | aa 3751-3770 | SEQ ID NO: 251 |
| P252: | EVDVL TKYSQ PEDSL IPFFE | aa 3766-3785 | SEQ ID NO: 252 |
| P253: | IPFFE ITVPE SQLTV SQFTL | aa 3781-3800 | SEQ ID NO: 253 |
| P254: | SQFTL PKSVS DGIAA LDLNA | aa 3796-3815 | SEQ ID NO: 254 |
| P255: | LDLNA VANKI ADFEL PTIIV | aa 3811-3830 | SEQ ID NO: 255 |
| P256: | PTIIV PEQTI EIPSI KFSVP | aa 3826-3845 | SEQ ID NO: 256 |
| P257: | KFSVP AGIVI PSFQA LTARF | aa 3841-3860 | SEQ ID NO: 257 |
| P258: | LTARF EVDSP VYNAT WSASL | aa 3856-3875 | SEQ ID NO: 258 |
| P259: | WSASL KNKAD YVETV LDSTC | aa 3871-3890 | SEQ ID NO: 259 |
| P260: | LDSTC SSTVQ FLEYE LNVLG | aa 3886-3905 | SEQ ID NO: 260 |
| P261: | LNVLG THKIE DGTLA SKTKG | aa 3901-3920 | SEQ ID NO: 261 |
| P262: | SKTKG TLAHR DFSAE YEEDG | aa 3916-3935 | SEQ ID NO: 262 |
| P263: | YEEDG KFEGL QEWEG KAHLN | aa 3931-3950 | SEQ ID NO: 263 |
| P264: | KAHLN IKSPA FTDLH LRYQK | aa 3946-3965 | SEQ ID NO: 264 |
| P265: | LRYQK DKKGI STSAA SPAVG | aa 3961-3980 | SEQ ID NO: 265 |
| P266: | SPAVG TVGMD MDEDD DFSKW | aa 3976-3995 | SEQ ID NO: 266 |
| P267: | DFSKW NFYYS PQSSP DKKLT | aa 3991-4010 | SEQ ID NO: 267 |
| P268: | DKKLT IFKTE LRVRE SDEET | aa 4006-4025 | SEQ ID NO: 268 |
| P269: | SDEET QIKVN WEEEA ASGLL | aa 4021-4040 | SEQ ID NO: 269 |
| P270: | ASGLL TSLKD NVPKA TGVLY | aa 4036-4055 | SEQ ID NO: 270 |
| P271: | TGVLY DYVNK YHWEH TGLTL | aa 4051-4070 | SEQ ID NO: 271 |
| P272: | TGLTL REVSS KLRRN LQNNA | aa 4066-4085 | SEQ ID NO: 272 |
| P273: | LQNNA EWVYQ GAIRQ IDDID | aa 4081-4100 | SEQ ID NO: 273 |
| P274: | IDDID VRFQK AASGT TGTYQ | aa 4096-4115 | SEQ ID NO: 274 |
| P275: | TGTYQ EWKDK AQNLY QELLT | aa 4111-4130 | SEQ ID NO: 275 |
| P276: | QELLT QEGQA SFQGL KDNVF | aa 4126-4145 | SEQ ID NO: 276 |
| P277: | KDNVF DGLVR VTQKF HMKVK | aa 4141-4160 | SEQ ID NO: 277 |
| P278: | HMKVK HLIDS LIDFL NFPRF | aa 4156-4175 | SEQ ID NO: 278 |
| P279: | NFPRF QFPGK PGIYT REELC | aa 4171-4190 | SEQ ID NO: 279 |
| P280: | REELC TMFIR EVGTV LSQVY | aa 4186-4205 | SEQ ID NO: 280 |
| P281: | LSQVY SKVHN GSEIL FSYFQ | aa 4201-4220 | SEQ ID NO: 281 |
| P282: | FSYFQ DLVIT LPFEL RKHKL | aa 4216-4235 | SEQ ID NO: 282 |
| P283: | RKHKL IDVIS MYREL LKDLS | aa 4231-4250 | SEQ ID NO: 283 |
| P284: | LKDLS KEAQE VFKAI QSLKT | aa 4246-4265 | SEQ ID NO: 284 |
| P285: | QSLKT TEVLR NLQDL LQFIF | aa 4261-4280 | SEQ ID NO: 285 |

TABLE 1-continued

| Peptide | Sequence | Apolipoprotein B aa | SEQ ID NO |
|---------|----------|---------------------|-----------|
| P286: | LQFIF QLIED NIKQL KEMKF | aa 4276-4295 | SEQ ID NO: 286 |
| P287: | KEMKF TYLIN YIQDE INTIF | aa 4291-4310 | SEQ ID NO: 287 |
| P288: | INTIF NDYIP YVFKL LKENL | aa 4306-4325 | SEQ ID NO: 288 |
| P289: | LKENL CLNLH KFNEF IQNEL | aa 4321-4340 | SEQ ID NO: 289 |
| P290: | IQNEL QEASQ ELQQI HQYIM | aa 4336-4355 | SEQ ID NO: 290 |
| P291: | HQYIM ALREE YFDPS IVGWT | aa 4351-4370 | SEQ ID NO: 291 |
| P292: | IVGWT VKYYE LEEKI VSLIK | aa 4366-4385 | SEQ ID NO: 292 |
| P293: | VSLIK NLLVA LKDFH SEYIV | aa 4381-4400 | SEQ ID NO: 293 |
| P294: | SEYIV SASNF TSQLS SQVEQ | aa 4396-4415 | SEQ ID NO: 294 |
| P295: | SQVEQ FLHRN IQEYL SILTD | aa 4411-4430 | SEQ ID NO: 295 |
| P296: | SILTD PDGKG KEKIA ELSAT | aa 4426-4445 | SEQ ID NO: 296 |
| P297: | ELSAT AQEII KSQAI ATKKI | aa 4441-4460 | SEQ ID NO: 297 |
| P298: | TKKII SDYHQ QFRYK LQDFS | aa 4457-4476 | SEQ ID NO: 298 |
| P299: | LQDFS DQLSD YYEKF IAESK | aa 4472-4491 | SEQ ID NO: 299 |
| P300: | IAESK RLIDL SIQNY HTFLI | aa 4487-4506 | SEQ ID NO: 300 |
| P301: | HTFLI YITEL LKKLQ STTVM | aa 4502-4521 | SEQ ID NO: 301 |
| P302: | STTVM NPYMK LAPGE LTIIL | aa 4517-4536 | SEQ ID NO: 302 |

The invention provides compositions comprising one or more peptides of ApoB-100 and/or derivatives, peptidomimetics, pharmaceutical equivalents and/or analogs thereof. In one embodiment, the compositions elicit an immune response and comprise one or more peptides of ApoB-100 and/or derivatives, peptidomimetics, pharmaceutical equivalents and/or analogs thereof and a pharmaceutically acceptable carrier. In another embodiment, the composition is for immunization and comprises one or more peptides of ApoB-100 and/or derivatives, peptidomimetics, pharmaceutical equivalents and/or analogs thereof and a pharmaceutically acceptable carrier that induces and/or enhances an immune response. In a further embodiment, the compositions for eliciting an immune response include one or more peptides of ApoB-100 and/or derivatives, peptidomimetics, pharmaceutical equivalents and/or an analogs thereof and CD8(+) T cells. The CD8+ T cells (such as autologous CD8+ T cells) are activated by one or more immunogenic peptides of ApoB-100. In an embodiment, the peptide of ApoB-100 is any one or more of peptides P1 to P302 as set forth in Table 1. In a further embodiment, one or more of the peptides of ApoB-100 are immunogenic peptides of ApoB-100. In an additional embodiment, the compositions for immunization include one or more peptides of ApoB-100 and/or derivatives, peptidomimetics, pharmaceutical equivalents and/or an analogs thereof and CD8(+) T cells. The CD8+ T cells (such as autologous CD8+ T cells) are activated by one or more immunogenic peptides of ApoB-100. In an embodiment, the peptide of ApoB-100 is any one or more of peptides P1 to P302 as set forth in Table 1. In a further embodiment, one or more of the peptides of ApoB-100 are immunogenic peptides of ApoB-100.

The compositions for eliciting an immune response and/or for immunizations/vaccinations comprising one or more of the immunogenic peptides of ApoB-100 described herein may be used to treat, inhibit, prevent and/or promotes prophylaxis of kidney diseases in subjects. The compositions eliciting an immune response and/or for immunizations/vaccinations comprising one or more of the immunogenic peptides of ApoB-100 described herein may also be used to mitigate the effects of kidney diseases, reduce the severity of kidney diseases, reduce the likelihood of developing kidney disease and/or slow the progression of kidney disease.

In some embodiments, a percentage of kidney disease reduction after administration of the compositions described herein is at least about 20%, at least about 30%, from about 40% to about 60% and/or about 50% to about 80%. In a further embodiment, the expected improvement in kidney disease after immunizations with a composition comprising one or more immunogenic peptides of ApoB-100 and/or administration with of activated CD8+ T cells is at least about 20% and/or about 20-80% relative to control subjects. In an embodiment, administration of the compositions described herein reduces mortality due to kidney disease, and/or reduce incidence of kidney disease.

Peptide Compositions for Vaccination

The invention provides composition comprising one or more peptides of ApoB-100 and/or derivatives, peptidomimetics, pharmaceutical equivalents and/or analogs thereof. In one embodiment, the composition elicits an immune response and comprises one or more peptides of ApoB-100 and/or derivatives, peptidomimetics, pharmaceutical equivalents and/or analogs thereof and a pharmaceutically acceptable carrier. In another embodiment, the composition is a vaccine and comprises one or more peptides of ApoB-100 and/or derivatives, peptidomimetics, pharmaceutical equivalents and/or analogs thereof and a pharmaceutically acceptable carrier that induces and/or enhances an immune response.

In some embodiments, the compositions (for eliciting an immune response and/or for vaccination) comprising fragments of ApoB-100, such as the immunogenic fragments of ApoB-100 associated with treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease, include at least one or more of peptides p1 (SEQ ID NO: 1), p2 (SEQ ID NO: 2), p10 (SEQ ID NO: 10), p11 (SEQ ID NO:11), p25 (SEQ ID NO:25), p30-p34 (SEQ ID NOs:30-34), p40 (SEQ ID NO:40), p40 (SEQ ID NO:40), p45 (SEQ ID NO:45), p68 (SEQ ID NO:68), p74 (SEQ ID NO:74), p94 (SEQ ID NO:94), p99 (SEQ ID NO:99), p100 (SEQ ID NO:100), p102 (SEQ ID NO:102), p103 (SEQ ID NO: 103), p105 (SEQ ID NO:105), p107 (SEQ ID NO:107), p111 (SEQ ID NO:111), p129 (SEQ ID NO:129), p143 (SEQ ID NO:143), p148 (SEQ ID NO:148), p149 (SEQ ID NO:149), p154 (SEQ ID NO:154), p162 (SEQ ID NO:162), p169 (SEQ ID NO:169), p177 (SEQ ID NO:177), p199 (SEQ ID NO:199), p210 (SEQ ID NO:210), p222 (SEQ ID NO:222), p236 (SEQ ID NO:236), p252 (SEQ ID NO:252), or p301 (SEQ ID NO:301), or immunologically active fragments thereof and/or combinations thereof.

In further embodiments, the compositions (for eliciting an immune response and/or for vaccination) comprising the fragments of ApoB-100, such as the immunogenic fragments of ApoB-100 associated with treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease, include one or more of peptides p2 (SEQ ID NO:2), p11 (SEQ ID NO:11), p32 (SEQ ID NO:32), p45 (SEQ ID NO: 45), p74 (SEQ ID NO: 74), p102 (SEQ ID NO: 102), p148 (SEQ ID NO:148), p162 (SEQ ID NO:162), or p210 (SEQ ID NO:210), or immunologically active fragments thereof and/or combinations thereof.

In additional embodiments, the compositions (for eliciting an immune response and/or for vaccination) comprising the fragments of ApoB-100 such as the immunogenic fragments of ApoB-100 associated with treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease, include one or more of peptides p2 (SEQ ID NO:2), p45 (SEQ ID NO: 45), p74 (SEQ ID NO: 74), p102 (SEQ ID NO: 102) and/or p210 (SEQ ID NO:210) or immunologically active fragments thereof and/or combinations thereof.

In a further embodiment, the compositions (for eliciting an immune response and/or for vaccination) comprising the fragment of ApoB-100 associated with treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease includes amino acids 3136-3155 of human ApoB-100 (P210; SEQ ID NO: 210) or an immunogenically active portion thereof.

T Cells and Peptide Compositions for Vaccination

The composition for eliciting an immune response and/or for vaccination to treat kidney disease, inhibit kidney disease, prevent kidney disease, promote prophylaxis of kidney disease, mitigate the effects of kidney disease, reduce the severity of kidney disease, reduce the likelihood of developing kidney disease and/or slow the progression of kidney disease, comprise activated CD8+ T cells (for example, autologous T cells) wherein the CD8+ T cells are activated by contacting CD8+ T cells with one or more immunogenic fragments of ApoB100. In an embodiment, activated CD8+ T cells specific for an immunogenic fragment of ApoB100 may be obtained by contacting a CD8+ T cells (for example, autologous CD8+ T cells) with any one or more of peptides p1 to p302 of ApoB-100 or an immunogenically active portion thereof for a time and under condition to activate the CD8+ T cell.

In some embodiments, activated CD8+ T cells specific for an immunogenic fragment of ApoB100 may be obtained by contacting a CD8+ T cells (for example, autologous CD8+ T cells) with any one or more of peptides p1 (SEQ ID NO: 1), p2 (SEQ ID NO: 2), p10 (SEQ ID NO: 10), p11 (SEQ ID NO:11), p25 (SEQ ID NO:25), p30-p34 (SEQ ID NOs:30-34), p40 (SEQ ID NO:40), p40 (SEQ ID NO:40), p45 (SEQ ID NO:45), p68 (SEQ ID NO:68), p74 (SEQ ID NO:74), p94 (SEQ ID NO:94), p99 (SEQ ID NO:99), p100 (SEQ ID NO:100), p102 (SEQ ID NO:102), p103 (SEQ ID NO: 103), p105 (SEQ ID NO:105), p107 (SEQ ID NO:107), p111 (SEQ ID NO:111), p129 (SEQ ID NO:129), p143 (SEQ ID NO:143), p148 (SEQ ID NO:148), p149 (SEQ ID NO:149), p154 (SEQ ID NO:154), p162 (SEQ ID NO:162), p169 (SEQ ID NO:169), p177 (SEQ ID NO:177), p199 (SEQ ID NO:199), p210 (SEQ ID NO:210), p222 (SEQ ID NO:222), p236 (SEQ ID NO:236), p252 (SEQ ID NO:252), or p301 (SEQ ID NO:301), or immunologically active fragments thereof and/or combinations thereof. In various embodiments, the above activated CD8+ T cells are administered as immunizations and/or to elicit an immune response.

In further embodiments, activated CD8+ T cells specific for an immunogenic fragment of ApoB100 may be obtained by contacting a CD8+ T cells (for example, autologous CD8+ T cells) with any one or more of peptides p2 (SEQ ID NO:2), p11 (SEQ ID NO:11), p32 (SEQ ID NO:32), p45 (SEQ ID NO: 45), p74 (SEQ ID NO: 74), p102 (SEQ ID NO: 102), p148 (SEQ ID NO:148), p162 (SEQ ID NO:162), or p210 (SEQ ID NO:210), or immunologically active fragments thereof and/or combinations thereof. In various embodiments, the above activated CD8+ T cells are administered as immunizations and/or to elicit an immune response.

In additional embodiments, activated CD8+ T cells specific for an immunogenic fragment of ApoB100 may be obtained by contacting a CD8+ T cells (for example, autologous CD8+ T cells) with any one or more of peptides SEQ ID NO:2, SEQ ID NO: 45, SEQ ID NO: 74, SEQ ID NO: 102, SEQ ID NO:210, or immunologically active fragments thereof and/or combinations thereof. In various embodiments, the above activated CD8+ T cells are administered as immunizations and/or to elicit an immune response.

In a further embodiment, activated CD8(+) T cells specific for an immunogenic fragment of ApoB100 may be obtained by contacting a CD8(+) T cells (for example, autologous CD8+ T cells) with an immunogenic fragment which includes the amino acids 3136-3155 of human ApoB-100 (for example P210; SEQ ID NO: 210) or an immunogenically active portion thereof. In various embodiments, the above activated CD8+ T cells are administered as immunizations and/or to elicit an immune response.

In general, the same combination of immunogenic fragments proven or expected to be associated with treatment and/or prevention of kidney disease in an individual are also expected to be able to activate CD8(+) T cells to be used in treatment and/or prevention of kidney disease in the individual. In particular, T cell activation can be performed using any of the molecules herein described administered in vivo in an amount suitable to be used with the methods of the invention (for example, to treat or prevent kidney disease). Activation of T cell can also be performed in vitro using methods and procedures such as the ones described in (R. Wu, et al., 1996 *Scand. J. Immunol.* 43, 381-384) as well as additional procedures identifiable by a skilled person.

In some embodiments, compositions comprising peptides of ApoB-100 (such as immunogenic peptides of ApoB-100) and CD8(+) T cells (for example, activated CD8+ T cells and/or autologous CD8+ T cells) further include an enhancer of CD8(+) T cell activation.

In an embodiment, the enhancer can be interleukin 2 (IL2), interleukin 10 (IL10), Interleukin 15 (IL-15), TGF-beta (TGF-β), IL2-antiIL-2 antibody complex and/or additional enhancer identifiable by a skilled person upon reading of the present disclosure. Reference is made to the references Mitchell et al 2010 (*J Immunol.* 2010 Jun. 15; 184(12):6719-30. Epub 2010 May 14), Perret et al 2008 (*Eur J Immunol.* 2008 October; 38(10):2886-95) and Kamimura et al 2007 (*J Exp Med.* 2007 Aug. 6; 204(8):1803-12. Epub 2007 Jul. 30). In some embodiments, the enhancing is performed by reducing CD86 expression and/or IL12 secretion by dendritic cells in the individual.

As disclosed herein, the immunogenic fragments of ApoB-100 or immunogenically active portion thereof, CD8 (+) T cell, and enhancers described herein can be provided as a part of systems to treat and/or prevent kidney disease or of a condition associated thereto. In an embodiment, the system comprises CD8(+) T cell activated with at least two ApoB-100 fragments or immunogenically active portions thereof, and one or more cytokine able to enhance the activated CD8 (+) T cell.

In an embodiment, the system comprises at least two or more immunogenic fragments of ApoB-100 or immunogenically active portion thereof and one or more of an activated CD8(+) T cell specific for an immunogenic fragment of ApoB-100.

Methods of the Invention

The invention provides methods for treating or inhibiting kidney disease in a subject in need thereof. The method comprises providing a composition comprising one or more peptides of ApoB-100 and/or derivatives, peptidomimetics, pharmaceutical equivalents and/or analogs thereof and administering an effective amount of the composition to the subject so as to treat or inhibit kidney disease in the subject.

In one embodiment, the composition for treating or inhibiting kidney diseases includes one or more peptides of ApoB-100 and/or derivatives, peptidomimetics, pharmaceutical equivalents and/or analogs thereof and a pharmaceutically acceptable carrier that may induce and/or enhance an immune response.

In another embodiment, the composition for treating or inhibiting kidney diseases includes one or more peptides of ApoB-100 and/or derivatives, peptidomimetics, pharmaceutical equivalents and/or an analogs thereof and CD8(+) T cells, wherein the CD8+ T cells are activated by one or more immunogenic peptides of ApoB-100. The CD8+ T cells may be autologous. The composition may further comprise enhancers.

In a further embodiment, the compositions for treating or inhibiting kidney diseases include a first composition comprising one or more peptides of ApoB-100 and/or derivatives, peptidomimetics, pharmaceutical equivalents and/or analogs thereof and a pharmaceutically acceptable carrier, and a second composition comprising activated CD8+ T cells and optionally, enhancers. In one embodiment, the first and second compositions are administered concurrently. In another embodiment, the first and second compositions are administered sequentially.

In some embodiments, the peptide of ApoB-100 in the compositions for treating or inhibiting kidney diseases is any one or more of peptides P1 to P302 as set forth in Table 1, or immunologically active fragments thereof and/or a combination thereof. In a further embodiment, the peptide of ApoB-100 is any one or more of peptides p2 (SEQ ID NO:2), p11 (SEQ ID NO:11), p32 (SEQ ID NO:32), p45 (SEQ ID NO: 45), p74 (SEQ ID NO: 74), p102 (SEQ ID NO: 102), p148 (SEQ ID NO:148), p162 (SEQ ID NO:162), or p210 (SEQ ID NO:210), or immunologically active fragments thereof and/or a combination thereof. In an embodiment, the peptide is p210 (SEQ ID NO:210).

The invention further provides methods for preventing kidney diseases or promoting prophylaxis of kidney diseases in a subject in need thereof. The method comprises providing a composition comprising one or more peptides of ApoB-100 and/or immunogenically active portions, derivatives, peptidomimetics, pharmaceutical equivalents and/or an analogs thereof and administering an effective amount of the composition to the subject so as to prevent or promote prophylaxis of kidney disease in the subject.

In one embodiment, the composition for preventing kidney diseases or promoting prophylaxis of kidney diseases includes one or more peptides of ApoB-100 and/or derivatives, peptidomimetics, pharmaceutical equivalents and/or analogs thereof and a pharmaceutically acceptable carrier that may induce and/or enhance an immune response.

In another embodiment, the composition for preventing kidney diseases or promoting prophylaxis of kidney diseases includes one or more peptides of ApoB-100 and/or derivatives, peptidomimetics, pharmaceutical equivalents and/or an analogs thereof and CD8(+) T cells, wherein the CD8+ T cells are activated by one or more immunogenic peptides of ApoB-100. The CD8+ T cells may be autologous. The composition may further comprise enhancers.

In a further embodiment, the compositions for preventing kidney diseases or promoting prophylaxis of kidney diseases include a first composition comprising one or more peptides of ApoB-100 and/or derivatives, peptidomimetics, pharmaceutical equivalents and/or analogs thereof and a pharmaceutically acceptable carrier, and a second composition comprising activated CD8+ T cells and optionally, enhancers. In one embodiment, the first and second compositions are administered concurrently. In another embodiment, the first and second compositions are administered sequentially.

In some embodiments, the peptide of ApoB-100 in the composition for preventing kidney diseases or promoting prophylaxis of kidney diseases is any one or more of peptides P1 to P302 as set forth in Table 1 or immunologically active fragments thereof and/or a combination thereof. In a further embodiment, the peptide of ApoB-100 is any one or more of peptides p2 (SEQ ID NO:2), p11 (SEQ ID NO:11), p32 (SEQ ID NO:32), p45 (SEQ ID NO: 45), p74 (SEQ ID NO: 74), p102 (SEQ ID NO: 102), p148 (SEQ ID NO:148), p162 (SEQ ID NO:162), or p210 (SEQ ID NO:210), or immunologically active fragments thereof and/or a combination thereof. In an embodiment, the peptide is p210 (SEQ ID NO:210).

The invention also provides methods for mitigating the effects of kidney disease, reducing the severity of kidney disease, reducing the likelihood of developing kidney disease and/or slowing the progression of kidney disease in a subject in need thereof. The methods comprise providing a composition comprising one or more peptides of ApoB-100 and/or immunogenically active portions, derivatives, peptidomimetics, pharmaceutical equivalents and/or an analogs thereof and administering an effective amount of the composition to the subject so as to mitigate the effects of kidney disease, reduce the severity of kidney disease, reduce the likelihood of developing kidney disease and/or slow the progression of kidney disease in the subject.

In one embodiment, the composition for mitigating the effects of kidney disease, reducing the severity of kidney disease, reducing the likelihood of developing kidney disease and/or slowing the progression of kidney disease includes one or more peptides of ApoB-100 and/or derivatives, peptidomimetics, pharmaceutical equivalents and/or analogs thereof and a pharmaceutically acceptable carrier that may induce and/or enhance an immune response.

In another embodiment, the composition for mitigating the effects of kidney disease, reducing the severity of kidney disease, reducing the likelihood of developing kidney disease and/or slowing the progression of kidney disease includes one or more peptides of ApoB-100 and/or derivatives, peptidomimetics, pharmaceutical equivalents and/or an analogs thereof and CD8(+) T cells, wherein the CD8+ T cells are activated by one or more immunogenic peptides of ApoB-100. The CD8+ T cells may be autologous. The composition may further comprise enhancers.

In a further embodiment, the compositions mitigating the effects of kidney disease, reducing the severity of kidney disease, reducing the likelihood of developing kidney disease and/or slowing the progression of kidney disease include a first composition comprising one or more peptides of ApoB-100 and/or derivatives, peptidomimetics, pharmaceutical equivalents and/or analogs thereof and a pharmaceutically acceptable carrier, and a second composition comprising activated CD8+ T cells and optionally, enhancers. In one embodiment, the first and second compositions are administered concurrently. In another embodiment, the first and second compositions are administered sequentially.

In some embodiments, the peptide of ApoB-100 in composition for mitigating the effects of kidney disease, reducing the severity of kidney disease, reducing the likelihood of developing kidney disease and/or slowing the progression of kidney disease is any one or more of peptides P1 to P302 as set forth in Table 1 or immunologically active fragments thereof and/or a combination thereof. In a further embodiment, the peptide of ApoB-100 is any one or more of peptides p2 (SEQ ID NO:2), p11 (SEQ ID NO:11), p32 (SEQ ID NO:32), p45 (SEQ ID NO: 45), p74 (SEQ ID NO: 74), p102 (SEQ ID NO: 102), p148 (SEQ ID NO:148), p162 (SEQ ID NO:162), or p210 (SEQ ID NO:210), or immunologically active fragments thereof and/or a combination thereof. In an embodiment, the peptide is p210 (SEQ ID NO:210).

The invention also provides methods for decreasing the expression of Angiotensin II type I receptor ($AT_1R$) in a subject in need thereof. The methods comprise providing a composition comprising one or more peptides of ApoB-100 and/or immunogenically active portions, derivatives, peptidomimetics, pharmaceutical equivalents and/or an analogs thereof and administering an effective amount of the composition to the subject so as to decrease the expression of AT1R.

In one embodiment, the composition for reducing the expression of AT1R includes one or more peptides of ApoB-100 and/or derivatives, peptidomimetics, pharmaceutical equivalents and/or analogs thereof and a pharmaceutically acceptable carrier that may induce and/or enhance an immune response.

In another embodiment, the composition for reducing the expression of AT1R includes one or more peptides of ApoB-100 and/or derivatives, peptidomimetics, pharmaceutical equivalents and/or an analogs thereof and CD8(+) T cells, wherein the CD8+ T cells are activated by one or more immunogenic peptides of ApoB-100. The CD8+ T cells may be autologous. The composition may further comprise enhancers.

In a further embodiment, the compositions for reducing the expression of AT1R include a first composition comprising one or more peptides of ApoB-100 and/or derivatives, peptidomimetics, pharmaceutical equivalents and/or analogs thereof and a pharmaceutically acceptable carrier, and a second composition comprising activated CD8+ T cells and optionally, enhancers. In one embodiment, the first and second compositions are administered concurrently. In another embodiment, the first and second compositions are administered sequentially.

In some embodiments, the peptide of ApoB-100 in composition for reducing the expression of $AT_1R$ is any one or more of peptides P1 to P302 as set forth in Table 1 or immunologically active fragments thereof and/or a combination thereof. In a further embodiment, the peptide of ApoB-100 is any one or more of peptides p2 (SEQ ID NO:2), p11 (SEQ ID NO:11), p32 (SEQ ID NO:32), p45 (SEQ ID NO: 45), p74 (SEQ ID NO: 74), p102 (SEQ ID NO: 102), p148 (SEQ ID NO:148), p162 (SEQ ID NO:162), or p210 (SEQ ID NO:210), or immunologically active fragments thereof and/or a combination thereof. In an embodiment, the peptide is p210 (SEQ ID NO:210).

In one embodiment, kidney disease may be atherosclerosis-related. In another embodiment, the kidney disease may be hypertension-related. In a further embodiment, the kidney disease may be diabetes. In an additional embodiment, the kidney disease may be autoimmune diseases-related.

In an embodiment, the effective amount of activated CD8 (+) T cells is about 500,000 to about 2,000,000 cells, about 500,000 to about 1,500,000 cells, about 500,000 to about 1,000,000 cells, about 750,000 to about 2,000,000 cells, about 750,000 to about 1,500,000 cells, or about 750,000 to about 1,000,000 cells. In an embodiment, administration of about 1,000,000 activated CD8(+) T cells is expected to result in both treatment and prevention of kidney diseases.

Administration is expected to be performed in accordance with dosages and schedules which will be identified based on the condition of the subject to be treated and the desired effect. For example if administration directed to prevention, administering an effective amount of activated CD8(+) T cell can performed by performing either a single administration, or a plurality of administrations (e.g. 3 administrations or more, 6 administrations or more) of activated CD8(+) T cell herein described in intervals to obtain a desired immunization based on the condition of the individual. In particular, a plurality of administrations can be performed whenever a prolonged immunizing effect is desired.

Administration of CD8(+) T cell herein described can be performed according to methods to immunize an individual identifiable to a skilled person. In an embodiment, administration can be performed by parenteral administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion. The activated CD8(+) T cells may be administered one time, or multiple times, depending on the desired duration of the immunization effect.

Dosages of the Invention

In some embodiments of the invention, the effective amount of one or more peptide of ApoB-100 and/or derivatives, peptidomimetics, pharmaceutical equivalents and/or analogs thereof in the compositions for eliciting an immune response and/or for immunization for treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease can be in the range of about 0.01-0.05 mg/day, 0.05-0.1 mg/day, 0.1-0.5 mg/day, 0.5-1 mg/day, 1-5 mg/day, 5-10 mg/day, 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day or 2900-3000 mg/day. The ApoB-100 peptides may be any one or more of peptides P1 to P302 as set forth in Table 1, or immunologically active fragments thereof and/or combinations thereof. In some embodiments, the compositions comprising the ApoB-100 peptides or immunologically active fragments thereof and/or combinations thereof comprise peptides in the above dosage ranges. In other embodiments, compositions comprising the ApoB-100 peptides or immunologically active fragments thereof and/or combinations thereof and activated CD8+ T cells comprise peptides in the above dosage ranges.

In other embodiments of the invention, the effective amount of one or more peptide of ApoB-100 and/or derivatives, peptidomimetics, pharmaceutical equivalents and/or analogs thereof in the compositions for eliciting an immune response and/or for immunization for treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease can be in the range of about 0.01-0.05 mg/immunization, 0.05-0.1 mg/immunization, 0.1-0.5 mg/immunization, 0.5-1 mg/immunization, 1-5 mg/immunization, 5-10 mg/immunization, 10-50 mg/immunization, 50-100 mg/immunization, 100-150 mg/immunization, 150-200 mg/immunization, 100-200 mg/immunization, 200-300 mg/immunization, 300-400 mg/immunization, 400-500 mg/immunization, 500-600 mg/immunization, 600-700 mg/immunization, 700-800 mg/immunization, 800-900 mg/immunization, 900-1000 mg/immunization, 1000-1100 mg/immunization, 1100-1200 mg/immunization, 1200-1300 mg/immunization, 1300-1400 mg/immunization, 1400-1500 mg/immunization, 1500-1600 mg/immunization, 1600-1700 mg/immunization, 1700-1800 mg/immunization, 1800-1900 mg/immunization, 1900-2000 mg/immunization, 2000-2100 mg/immunization, 2100-2200 mg/immunization, 2200-2300 mg/immunization, 2300-2400 mg/immunization, 2400-2500 mg/immunization, 2500-2600 mg/immunization, 2600-2700 mg/immunization, 2700-2800 mg/immunization, 2800-2900 mg/immunization or 2900-3000 mg/immunization. The ApoB-100 peptides may be any one or more of peptides P1 to P302 as set forth in Table 1. The ApoB-100 peptides may be any one or more of peptides P1 to P302 as set forth in Table 1, or immunologically active fragments thereof and/or combinations thereof. In some embodiments, the compositions comprising the ApoB-100 peptides or immunologically active fragments thereof and/or combinations thereof comprise peptides in the above dosage ranges. In other embodiments, compositions comprising the ApoB-100 peptides or immunologically active fragments thereof and/or combinations thereof and activated CD8+ T cells comprise peptides in the above dosage ranges. In an additional embodiment, an effective amount of p210 is about 100 μg of p210/immunization. In an alternative embodiment, an effective amount of p210 is about 250 μg to about 500 μg.

In further embodiments of the invention, the effective amount of one or more peptide of ApoB-100 and/or derivatives, peptidomimetics, pharmaceutical equivalents and/or analogs thereof in the compositions for eliciting an immune response and/or for immunization for treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease can be in the range of about 0.01-0.05 mg/kg, 0.05-0.1 mg/kg, 0.1-0.5 mg/kg, 0.5-1 mg/kg, 1-5 mg/kg, 5-10 mg/kg, 10-50 mg/kg, 50-100 mg/kg, 100-150 mg/kg, 150-200 mg/kg, 100-200 mg/kg, 200-300 mg/kg, 300-400 mg/kg, 400-500 mg/kg, 500-600 mg/kg, 600-700 mg/kg, 700-800 mg/kg, 800-900 mg/kg, 900-1000 mg/kg, 1000-1100 mg/kg, 1100-1200 mg/kg, 1200-1300 mg/kg, 1300-1400 mg/kg, 1400-1500 mg/kg, 1500-1600 mg/kg, 1600-1700 mg/kg, 1700-1800 mg/kg, 1800-1900 mg/kg, 1900-2000 mg/kg, 2000-2100 mg/kg, 2100-2200 mg/kg, 2200-2300 mg/kg, 2300-2400 mg/kg, 2400-2500 mg/kg, 2500-2600 mg/kg, 2600-2700 mg/kg, 2700-2800 mg/kg, 2800-2900 mg/kg or 2900-3000 mg/kg. The ApoB-100 peptides may be any one or more of peptides P1 to P302 as set forth in Table 1, or immunologically active fragments thereof and/or combinations thereof. In some embodiments, the compositions comprising the ApoB-100 peptides or immunologically active fragments thereof and/or combinations thereof comprise peptides in the above dosage ranges. In other embodiments, compositions comprising the ApoB-100 peptides or immunologically active fragments thereof and/or combinations thereof and activated CD8+ T cells comprise peptides in the above dosage ranges.

In an embodiment, the effective amount of immunogenic peptide of ApoB-100 may vary depending on the number and combination of peptides utilized for each immunization, and specific characteristic and conditions of the individual treated (e.g. immune system, diet and general health and additional factors identifiable by a skilled person). Additionally, lower or higher amounts within the defined range are expected to be effective in an individual depending on factors such as weight, age, gender of the individual as well as additional factors identifiable by a skilled person.

In some embodiments, the immunogenic peptides herein described or related immunogenically active portions can be administered in combination with an adjuvant or other carrier suitable to affect and in particular increase immunogenicity of the peptide o active portion thereof. In some embodiments, the immunogenic peptide or active portion thereof can be conjugated to the adjuvant or carrier according to procedures identifiable to a skilled person. Suitable carriers comprise BSA, and in particular, cationized BSA, Human Serum Albumin (HSA) and in particular cationized HSA, aluminum salts such as aluminum phosphate and aluminum hydroxide and additional carriers identifiable by a skilled person.

In an embodiment, the administering is performed according to a schedule of administration to be determined in view of the desired effect. In particular, administration is expected to be performed in accordance with dosages and schedule which will be identified based on the condition of the individual to be treated and the desired effect. For example, administration can be performed by performing either a single administration, or a plurality of administrations (e.g. 2 administrations or more, in particular up to 6 administrations) of immunogenic fragments or immunogenically active portion thereof herein described in intervals to obtain a desired immunization based on the condition of the individual.

The route of immunization can vary depending on the purposes of immunization described herein. Successful prevention and treatment of kidney diseases in mice occurred by subcutaneous osmotic pump injections. The type of immune response triggered is largely determined by the route of immunization. Various routes can be used comprising subcutaneous, parenteral, and systemic among the others. In particular, the mucosal linings of airways and intestines contain lymphatic tissue that, when exposed to antigen, elicits anti-inflammatory, immunosuppressive responses. Distinct immunological features of the respiratory and intestinal mucosa lead to partly different types of protective immunity upon antigen exposure by the nasal or oral route.

As described above, administering an effective amount of CD8+ T cells activated with any one or more of peptides (for example immunogenic peptides) of ApoB-100 is associated with treating kidney disease, inhibiting kidney disease, preventing kidney disease, promoting prophylaxis of kidney disease, mitigating the effects of kidney disease, reducing the severity of kidney disease, reducing the likelihood of developing kidney disease and/or slowing the progression of kidney disease. In an embodiment the effective amount of activated CD8+ T cells may be between about 500,000 and 2,000,000 cells. In another embodiment the effective amount of activated CD8+ T cells may be between about 750,000 and about 1,500,000 cells. In an additional embodiment, the effective amount of activated CD8+ T cells may be about 1,000,000 cells.

Typical dosages of an effective amount of one or more peptide of ApoB-100 and/or derivatives, peptidomimetics, pharmaceutical equivalents and/or analogs thereof in the composition can be in the ranges recommended by the manufacturer where known therapeutic compounds are used, and also as indicated to the skilled artisan by the in vitro responses or responses in animal models. The same or similar dosing can be used in accordance with various embodiments of the present invention, or an alternate dosage may be used in connection with alternate embodiments of the invention. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

In one embodiment, administration of activated CD8+ T cell herein described can be performed according to methods used in the art to immunize an individual. In another embodiment, the administering can be performed by parenteral administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion. In an embodiment the administering can be performed by intravenous administration.

The invention also provides that the activated CD8+ T cells, obtained by contacting a CD8+ T cells (for example, autologous CD8+ T cells) with any one or more of peptides P1 to P302 as set forth in Table 1, may be administered alone or in combination with an effective amount of any one or more peptides (for example immunogenic peptides) P1 to P302 of ApoB-100 or immunogenic portions thereof.

In an embodiment, compositions comprising peptides of ApoB-100 including peptides P1 to P302 and/or immunogenic fragments thereof may be administered once daily or multiple times daily. Similarly, activated CD8+ T cells, obtained by contacting a CD8+ T cells (for example, autologous CD8+ T cells) with any one or more of peptides P1 to P302 as set forth in Table 1, may be administered once daily or multiple times daily depending on the desired duration of the immunization effect.

In some embodiments, administering of an immunogenic fragment and/or a CD8(+) T cell can be performed in combination with an enhancer of CD8(+) T cell activation including but not limited to Interleukin 2 (IL2), Interleukin 15 (IL-15), TGFbeta(TGF-β), IL2-antiIL-2 antibody complex and/or additional enhancer identifiable by a skilled person upon reading of the present disclosure. Reference is made to the references Mitchell et al (*J Immunol.* 2010 Jun. 15; 184(12): 6719-30. Epub 2010 May 14), Perret et al (*Eur J Immunol.* 2008 October; 38(10):2886-95) and Kamimura et al (*J Exp Med.* 2007 Aug. 6; 204(8):1803-12. Epub 2007 Jul. 30), each incorporated by reference in its entirety, which describe exemplary use of enhancer in connection with T cell activation. In additional embodiments, the enhancing is performed by reducing CD86 expression and/or IL12 secretion by dendritic cells in the individual.

The subjects in the claimed invention may be any one or more of human, non-human primate, monkey, ape, dog, cat, cow, horse, rabbit, mouse and rat.

Pharmaceutical Compositions and Kits

As described above, the invention provides compositions (for eliciting an immune response and/or for immunizations) comprising one or more peptides of ApoB-100 and/or derivatives, peptidomimetics, pharmaceutical equivalents and/or analogs thereof. In one embodiment, the composition comprises one or more peptides of ApoB-100 and/or derivatives, peptidomimetics, pharmaceutical equivalents and/or analogs thereof and a pharmaceutically acceptable carrier that induces and/or enhances an immune response. In another embodiment, the composition includes one or more peptides of ApoB-100 and/or derivatives, peptidomimetics, pharmaceutical equivalents and/or an analogs thereof and CD8(+) T cells. The CD8+ T cells are activated by one or more immunogenic peptides of ApoB-100. In an embodiment, the peptide of ApoB-100 is any one or more of peptides P1 to P302 as set forth in Table 1. In a further embodiment, one or more of the peptides of ApoB-100 are immunogenic peptides of ApoB-100.

The compositions (for eliciting an immune response and/or for immunizations) can be formulated as freeze-dried or liquid preparations according to any means suitable in the art. Non-limiting examples of liquid form preparations include solutions, suspensions, syrups, slurries, and emulsions. Suitable liquid carriers include any suitable organic or inorganic solvent, for example, water, alcohol, saline solution, buffered saline solution, physiological saline solution, dextrose solution, water propylene glycol solutions, and the like, preferably in sterile form.

The compositions (for eliciting an immune response and/or for immunizations) can be formulated in either neutral or salt forms. Pharmaceutically acceptable salts include the acid addition salts (formed with the free amino groups of the active polypeptides) and which are formed with inorganic acids such as, for example, hydrochloric or phosphoric acids, or organic acids such as acetic, oxalic, tartaric, mandelic, and the like. Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In various embodiments, the compositions are administered intradermally, subcutaneously, intramuscularly, or intravenously. The compositions may be formulated for inoculation or injection into the subject. For injection, the compositions of the invention can be formulated in aqueous solutions such as water or alcohol, or in physiologically compatible buffers such as Hanks's solution, Ringer's solution, or physiological saline buffer. The solution can contain formulatory agents such as suspending, preserving, stabilizing and/or dispersing agents. Injection formulations can also be prepared as solid form preparations which are intended to be converted, shortly before use, to liquid form preparations suitable for injection, for example, by constitution with a suitable vehicle, such as sterile water, saline solution, or alcohol, before use.

The compositions (for eliciting an immune response and/or for immunizations) can also be formulated in sustained release vehicles or depot preparations. Such long acting formulations can be administered by inoculation or implantation (for example subcutaneously or intramuscularly) or by injection. Thus, for example, the vaccine compositions can be formulated with suitable polymeric or hydrophobic materials (for example, as an emulsion in acceptable oil) or ion exchange resins, or as sparingly soluble derivatives, for example, as a sparingly soluble salt. Liposomes and emulsions are well-known examples of delivery vehicles suitable for use as carriers.

The compositions (for eliciting an immune response and/or for immunizations) can comprise agents that enhance the efficacy of the composition, such as adjuvants. Adjuvants include any compound or compounds that act to increase an immune response to the ApoB100 peptides or immunogenically active portions thereof, thereby reducing the quantity of antigen necessary in the vaccine, and/or the frequency of administration necessary to generate a protective immune response. Adjuvants can include for example, emulsifiers, muramyl dipeptides, pyridine, aqueous adjuvants such as aluminum hydroxide, chitosan-based adjuvants, and any of the various saponins, oils, and other substances known in the art, such as Amphigen, LPS, bacterial cell wall extracts, bacterial DNA, CpG sequences, synthetic oligonucleotides and combinations thereof (Schijns et al. (2000) Curr. Opin. Immunol. 12:456), *Mycobacterialphlei* (*M. phlei*) cell wall extract (MCWE) (U.S. Pat. No. 4,744,984), *M. phlei* DNA (M-DNA), and M-DNA-*M. phlei* cell wall complex (MCC).

Compounds which can serve as emulsifiers include natural and synthetic emulsifying agents, as well as anionic, cationic and nonionic compounds. Among the synthetic compounds, anionic emulsifying agents include, for example, the potassium, sodium and ammonium salts of lauric and oleic acid, the calcium, magnesium and aluminum salts of fatty acids, and organic sulfonates such as sodium lauryl sulfate. Synthetic cationic agents include, for example, cetyltrhethylammonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan monopalmitate). Natural emulsifying agents include acacia, gelatin, lecithin and cholesterol.

Other suitable adjuvants can be formed with an oil component, such as single oil, a mixture of oils, a water-in-oil emulsion, or an oil-in-water emulsion. The oil can be a mineral oil, a vegetable oil, or animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils include, for example, canola oil, almond oil, cottonseed oil, corn oil, olive oil, peanut oil, safflower oil, sesame oil, soybean oil, and the like. Freund's Complete Adjuvant (FCA) and Freund's Incomplete Adjuvant (FIA) are two common adjuvants that are commonly used in vaccine preparations, and are also suitable for use in the present invention. Both FCA and FIA are water-in-mineral oil emulsions; however, FCA also contains a killed *Mycobacterium* sp.

Immunomodulatory cytokines can also be used in the compositions to enhance the efficacy of the composition, for example, as an adjuvant. Non-limiting examples of such cytokines include interferon alpha (IFN-α), interleukin-2 (IL-2), and granulocyte macrophage-colony stimulating factor (GM-CSF), or combinations thereof. GM-CSF is highly preferred.

Compositions comprising ApoB100 peptides or immunogenically active portions and further comprising adjuvants can be prepared using techniques well known to those skilled in the art including, but not limited to, mixing, sonication and microfluidation. The adjuvant can comprise from about 10% to about 50% (v/v) of the vaccine composition, about 20% to about 40% (v/v), about 20% to about 30% (v/v), or any integer within these ranges.

Administration of the compositions can be by infusion or injection (e.g., intravenously, intramuscularly, intracutaneously, subcutaneously, intrathecal, intraduodenally, intraperitoneally, and the like). The vaccine compositions can also be administered intranasally, vaginally, rectally, orally, or transdermally. Additionally, vaccine compositions can be administered by "needle-free" delivery systems. In an embodiment, the compositions are administered by intradermal injection. Administration can be at the direction of a physician or physician assistant.

The injections can be split into multiple injections, with such split inoculations administered preferably substantially concurrently. When administered as a split inoculation, in an embodiment, the dose of the immunogen may be proportioned equally in each separate injection. If an adjuvant is present in the vaccine composition, the dose of the adjuvant may be proportioned equally in each separate injection. The separate injections for the split inoculation may be administered substantially proximal to each other on the subject's body. In some aspects, the injections are administered at least about 1 cm apart from each other on the body, at least about 2.5 cm apart from each other on the body, at least about 5 cm apart from each other on the body, at least about 10 cm apart from each other on the body or more than 10 cm apart from each other on the body, for example, at least about 12.5, 15, 17.5, 20, or more cm apart from each other on the body. Primary immunization injections and booster injections can be administered as a split inoculation.

Various alternative pharmaceutical delivery systems can be employed. Non-limiting examples of such systems include liposomes and emulsions. Certain organic solvents such as dimethylsulfoxide also can be employed. Additionally, the vaccine compositions can be delivered using a sustained-release system, such as semipermeable matrices of solid polymers containing the therapeutic agent. The various sustained-release materials available are well known by those skilled in the art. Sustained-release capsules can, depending on their chemical nature, release the vaccine compositions over a range of several days to several weeks to several months.

Effective amounts of an immunogenic fragment to treat and/or prevent kidney disease will depend on the individual wherein the activation is performed and will be identifiable by a skilled person. For example in an embodiment the T cell activation can be performed with an effective amount of from about 1 to about 100 μg immunogenic fragment or immunogenically active portion thereof. In an embodiment, treatment and/or prevention of kidney disease can be performed with an effective amount of from about 1 to about 100 mg ApoB fragment or immunogenically active portion thereof. Additional effective amounts are identifiable by a skilled person in view of the individual where activation is performed and the desired activation. In an embodiment, an effective amount for the treatment or prevention can be about 100 μg or more. A greater concentration can be used in some embodiments depending on the desired effect as illustrated in the present disclosure. For example, in embodiments wherein treatment of kidney disease is expected to be performed with an effective amount of 250 μg or more. In another example, wherein the kidney disease is less severe an effective amount to treat the kidney disease is expected to be 25 μg or 50 μg.

The effective amount of the composition can be dependent on any number of variables, including without limitation, the species, breed, size, height, weight, age, overall health of the patient, the type of formulation, the mode or manner or administration, or the presence or absence of risk factors that significantly increase the likelihood that kidney disease may occur. The effective amount is also expected to vary depending on the number and combination of peptides utilized for each particular composition, and specific characteristic and conditions of the individual treated (e.g. immune system diet and general health and additional factors identifiable by a skilled person).

Toxicity and therapeutic efficacy of the compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. Data obtained from cell culture assays and animal studies can be used in formulating a range of dosage for use in patients. The dosage of such compositions lies preferably within a range of circulating concentrations that include the ED50 with little or no toxicity. The dosage can vary within this range depending upon the dosage form employed and the route of administration utilized.

Toxicity information can be used to more accurately determine useful doses in a specified subject such as a human. The treating physician can terminate, interrupt, or adjust administration due to toxicity, or to organ dysfunctions, and can adjust treatment as necessary if the clinical response is not adequate, to improve the response. The magnitude of an administrated dose in the prevention of recurrent kidney disease will vary with the severity of the patient's condition, relative risk for recurrence, or the route of administration, among other factors. The severity of the patient's condition can, for example, be evaluated, in part, by standard prognostic evaluation methods.

The compositions can be administered to a patient on any schedule appropriate to induce and/or sustain protective immunity against kidney disease relapse and more specifically to induce and/or sustain a cytotoxic T lymphocyte response to ApoB fragment or immunogenically active portion thereof. For example, patients can be administered a composition as a primary immunization as described and exemplified herein, followed by administration of a booster to bolster and/or maintain the protective immunity.

In some aspects, patients can be administered the vaccine compositions 1, 2 or more times per month. In an embodiment, once per month for six consecutive months may establish the protective immune response, particularly with respect to the primary immunization schedule. In some aspects, boosters can be administered at regular intervals such as every 6 or more months after completion of the primary immunization schedule. In an embodiment, administration of the booster is every 6 months. Boosters can also be administered on an as-needed basis.

The administration schedule for the composition including primary immunization and booster administration can continue as long as needed for the patient, for example, over the course of several years, to over the lifetime of the patient. In some aspects, the vaccine schedule includes more frequent administration at the beginning of the vaccine regimen, and includes less frequent administration (e.g., boosters) over time to maintain the protective immunity.

The composition can be administered at lower doses at the beginning of the regimen, with higher doses administered over time. The composition can also be administered at higher doses at the beginning of the regimen, with lower doses administered over time. The frequency of primary administration and booster administration and dose of ApoB fragments or immunogenically active portions thereof administered can be tailored and/or adjusted to meet the particular needs of individual patients, as determined by the administering physician according to any means suitable in the art.

The present invention is also directed to kits to treat, inhibit, reduce severity of, mitigate the effects of and/or promote prophylaxis of kidney disease in a subject in need thereof. The kit comprises ApoB-100 peptides or immunogenic fragments thereof, for example peptides set forth in Table 1 or a derivative, variant, pharmaceutical equivalent, peptidomimetic and/or analog thereof. Alternatively, the kits comprise CD8+ T cells (for example, activated CD8+ T cells) and pharmaceutically acceptable carriers. The kits may also comprise ApoB-100 peptides or immunogenically active fragments thereof and activated CD8+ T cells. The kit is an assemblage of materials or components, including at least one of the inventive compositions. Additional components of the kit may include enhancer molecules.

The exact nature of the components configured in the inventive kit depends on its intended purpose. In one embodiment, the kit is configured particularly for human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to treat, prevent, inhibit, prevent metastasis of and/or promote prophylaxis of cancer (for example leukemia) in a subject. Optionally, the kit also contains other useful components, such as, measuring tools, diluents, buffers, pharmaceutically acceptable carriers, syringes or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. Thus, for example, a package can be a bottle used to contain suitable quantities of the compositions of the invention. The packaging material generally has an external label which indicates the contents and/or purpose of the kit and/or its components.

EXAMPLES

The following example is provided to better illustrate the claimed invention and is not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

The inventors assessed the effect of p210 immunization on AngII-induced renal inflammatory responses in apoE (−/−) male mice. For the experiments described herein, native p210 peptide (KTTKQ SFDLS VKAQY KKNKH) was conjugated to cationic bovine serum albumin (cBSA) as carrier. Alum was used as an adjuvant. At 7, 10, and 12 weeks of age, male apoE (−/−) mice were subcutaneously injected with 100 μg of p210/cBSA/Alum. As immunization controls, 100 μg of cBSA/Alum, or PBS were injected. At 10 weeks of age after first immunization booster, 1000 ng/Kg/min of AngII was delivered by subcutaneously implanted osmotic pump for 4 weeks (FIG. 1A).

As shown in FIG. 1B, administration of p210, an immunogenic peptide of ApoB-100 reduces the levels of the $AT_1$ receptor. p210 immunization significantly decreased the expression of Angiotensin II type 1 receptor (AT1R) in aorta.

Serum creatinine (Cr.) (an indicator of renal function) level at 14 weeks of age was assessed by commercially available creatinine assay kit following the manufacture's instruction. As shown in Table 2, p210 immunization protected against AngII-induced renal damage. Serum creatinine level was significantly lower in p210 group. *p<0.05 vs. p210. N: p210=12, cBSA=11, PBS=9.

TABLE 2

|  | P210 | cBSA | PBS |
| --- | --- | --- | --- |
| Serum Cr. (mg/dl) | 0.6 ± 0.1 | 1.1 ± 0.2* | 1.3 ± 0.1* |

Figure 2:
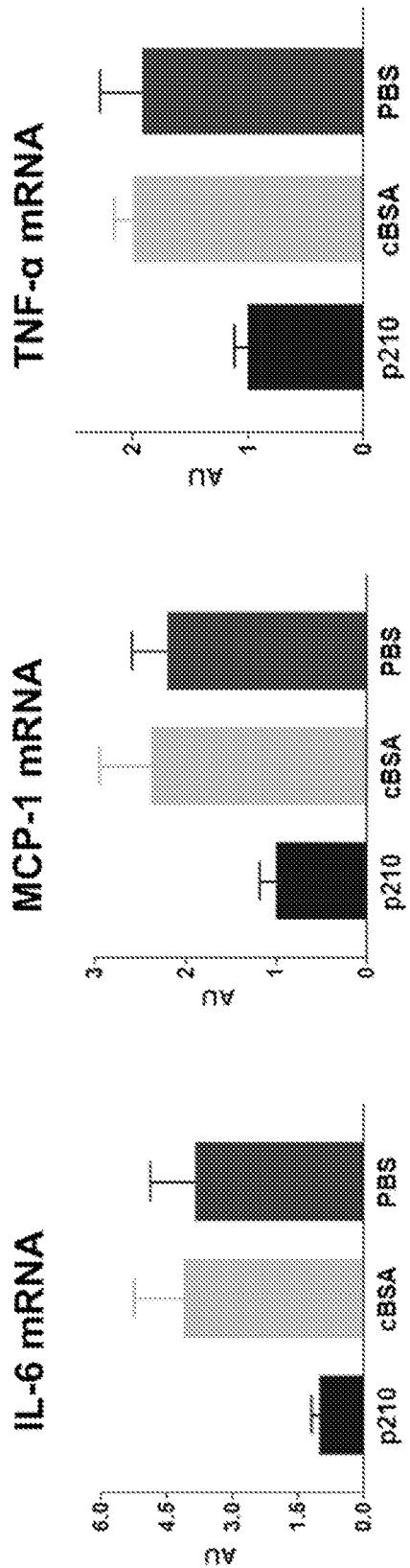
FIG. 2 depicts, in accordance with an embodiment of the invention that the p210 vaccine significantly reduced IL-6 (N=8 each), MCP-1 (N=8 each), and TNF-α (N=10 each) mRNA expression in kidney. *p<0.05 vs. p210. p210: immunized with p210/cB SA/Alum+AngII; cBSA: immunized with cBSA/Alum+AngII; PBS: immunized with PBS+AngII.

At euthanasia, kidney was harvested for quantitative PCR analysis or histological analysis. Data are presented as mean±SEM. Data were analyzed by ANOVA following post-hoc test for multiple group comparison. Immunization with p210 vaccine significantly attenuated AngII-induced renal damage. As shown in FIG. 2, the p210 immunization downregulated pro-inflammatory gene expressions (IL-6, MCP-1, and TNF-α) in kidney.

Figure 3:
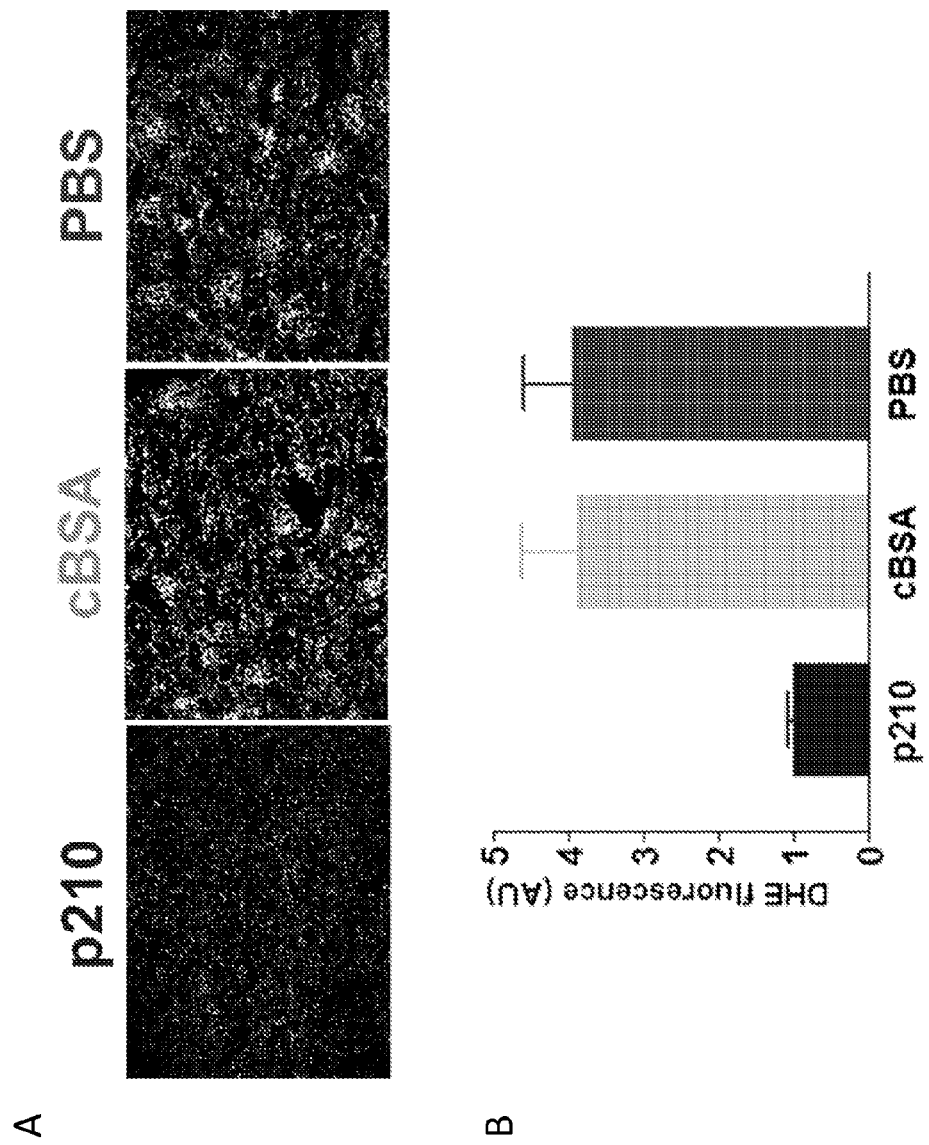
FIG. 3 depicts, in accordance with an embodiment of the invention that the p210 vaccine significantly reduced glomerular ROS production. (A) Representative figure of in situ DHE labeling. (B) Densitometric analysis of DHE fluorescence. *p<0.05 vs. p210. N=4 each. p210: immunized with p210/cBSA/Alum+AngII; cBSA: immunized with cBSA/Alum+AngII; PBS: immunized with PBS+AngII.

Superoxide production in kidney was measured by in situ dihydroethidium (DHE) methods with freshly cut frozen sections. As shown in FIG. 3, the p210 immunization significantly reduced glomerular ROS production.

Figure 4:
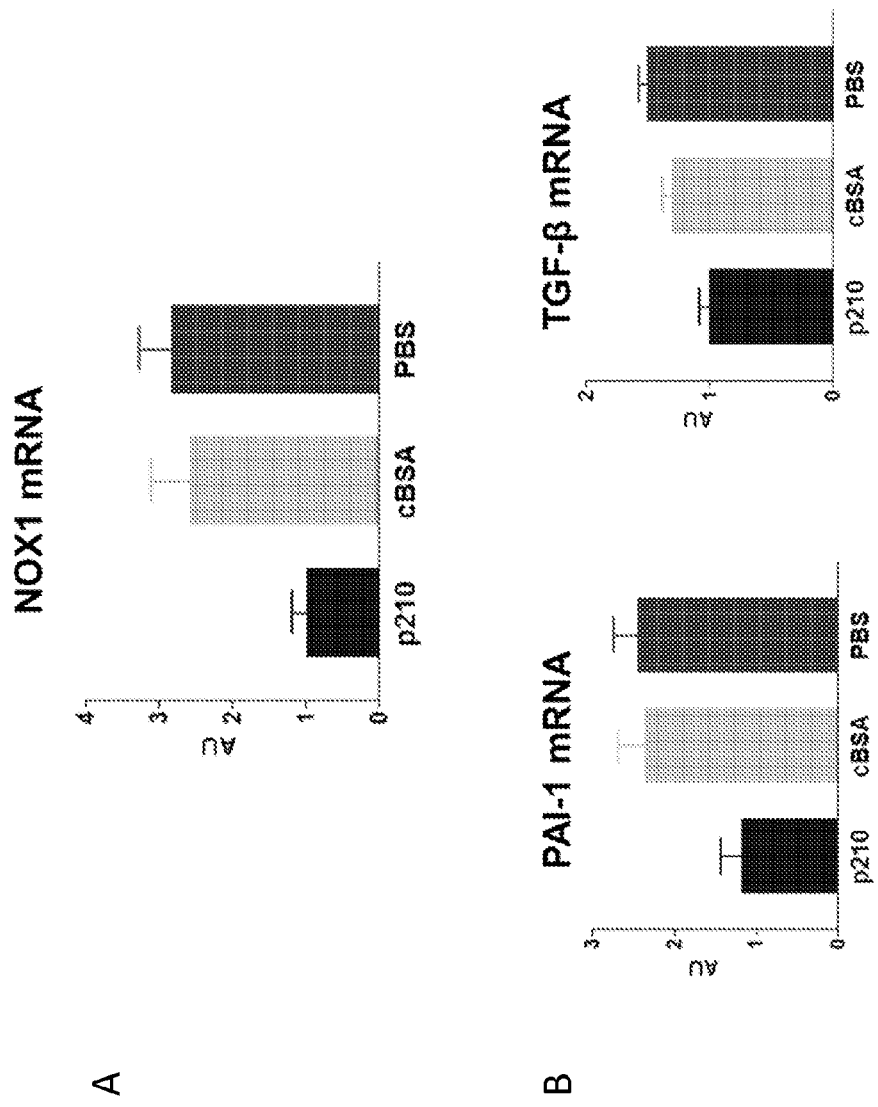
FIG. 4 depicts, in accordance with an embodiment of the invention that (A) p210 vaccine significantly reduced NOX1, a component of NADPH oxidase, expression in kidney. *p<0.05 vs. p210. N=8 each, and (B) p210 vaccine significantly reduced PAI-1 and TGF-β mRNA expression in kidney. (Left): PAI-1. N=5 each, (Right): TGF-β. N=9 each. *p<0.05 vs. p210. p210: immunized with p210/cBSA/Alum+AngII; cBSA: immunized with cBSA/Alum+AngII; PBS: immunized with PBS+AngII.

As shown in FIG. 4A, p210 immunization significantly reduced NOX1, a component of NADPH oxidase. As shown in FIG. 4B, the p210 vaccine significantly downregulated profibrotic gene expression (PAI-1 and TGF-β) in kidney. These anti-hypertensive and renal protective effects are associated with significant reduction of inflammatory cytokines and chemokine gene expression, ROS production mediated by NADPH oxidase, and profibrotic gene expression in kidney. Accordingly, in an exemplary embodiment, immunogenic peptide p210 and/or immunogenic fragments thereof may be good therapeutic agents for Angiotensin associated or related diseases such as kidney diseases and kidney malfunction.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* $3^{rd}$ ed., J. Wiley & Sons (New York, N.Y. 2001); March, *Advanced Organic Chemistry Reactions, Mechanisms and Structure* $5^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

The invention claimed is:

1. A method of treating kidney disease in a subject in need thereof, wherein the subject has been diagnosed with kidney disease, comprising:
   (a) providing a composition comprising one or more peptides of ApoB-100 or immunogenically active portions of said peptides, wherein the one or more peptides of ApoB-100 is any one or more of peptides p1 (SEQ ID NO: 1), p2 (SEQ ID NO: 2), p10 (SEQ ID NO: 10), p11 (SEQ ID NO: 11), p25 (SEQ ID NO: 25), p30-p34 (SEQ ID NOs: 30-34), p40 (SEQ ID NO: 40), p45 (SEQ ID NO: 45), p68 (SEQ ID NO: 68), p74 (SEQ ID NO: 74), p94 (SEQ ID NO: 94), p99 (SEQ ID NO: 99), p100 (SEQ ID NO: 100), p102 (SEQ ID NO: 102), p103 (SEQ ID NO: 103), p105 (SEQ ID NO: 105), p107 (SE ID NO: 107), p111 (SEQ ID NO: 111), p129 (SEQ ID NO: 129), p143 (SEQ ID NO: 143), p148 (SEQ ID NO: 148), p149 (SEQ ID NO: 149), p154 (SEQ ID NO: 154), p162 (SEQ ID NO: 162), p169 (SEQ ID NO: 169), p177 (SEQ ID NO: 177), p199 (SEQ ID NO: 199), p210 (SEQ ID NO: 210), p222 (SEQ ID NO: 222), p236 (SEQ ID NO: 236), p252 (SEQ ID NO: 252), or p301 (SEQ ID NO: 301), or a combination thereof; and
   (b) administering an effective amount of the composition to the subject, so as to treat kidney disease in the subject.

2. The method of claim 1, wherein the peptide of ApoB-100 is any one or more of peptides p2 (SEQ ID NO: 2), p11 (SEQ ID NO: 11), p32 (SEQ ID NO: 32), p45 (SEQ ID NO: 45), p74 (SEQ ID NO: 74), p102 (SEQ ID NO: 102), p148 (SEQ ID NO: 148), p162 (SEQ ID NO: 162), or p210 (SEQ ID NO: 210), or a combination thereof.

3. The method of claim 1, wherein the peptide of ApoB-100 is any one or more of peptides p2 (SEQ ID NO: 2), p45 (SEQ ID NO: 45), p74 (SEQ ID NO: 74), p102 (SEQ ID NO: 102), p210 (SEQ ID NO: 210), or a combination thereof.

4. The method of claim 1, wherein the peptide of ApoB-100 is p210 (SEQ ID NO: 210).

5. The method of claim 1, wherein the effective amount is about 100 to about 500 μg.

6. The method of claim 1, wherein the kidney disease is atherosclerosis-related kidney disease, hypertension-related kidney disease or diabetes.

7. A method of treating kidney disease in a subject in need thereof comprising:
   (a) providing a composition comprising CD8+T cells activated with one or more peptides of ApoB-100 or immunogenically active portions of said peptides, wherein the one or more peptides of ApoB-100 is any one or more of peptides p1 (SEQ ID NO: 1), p2 (SEQ ID NO: 2), p10 (SEQ ID NO: 10), p11 (SEQ ID NO: 11), p25 (SEQ ID NO: 25), p30-34 (SEQ ID NOs: 30-34), p40 (SEQ ID NO: 40), p45 (SEQ ID NO: 45), p68 (SEQ ID NO: 68), p74 (SEQ ID NO: 74), p94 (SEQ ID NO: 94), p99 (SEQ ID NO: 99), p100 (SEQ ID NO: 100), p102 (SEQ ID NO: 102), p103 (SEQ ID NO: 103), p105 (SEQ ID NO: 105), p107 (SEQ ID NO: 107), p111 (SEQ ID NO: 111), p129 (SEQ ID NO: 129), p143 (SEQ ID NO: 143), p148 (SEQ ID NO: 148), p149 (SEQ ID NO: 149), p154 (SEQ ID NO: 154), p162 (SEQ ID NO: 162), p169 (SEQ ID NO: 169), p177 (SEQ ID NO: 177), p199 (SEQ ID NO: 199), p210 (SEQ ID NO: 210), p222 (SEQ ID NO: 222), p236 (SEQ ID NO: 236), p252 (SEQ ID NO: 252), or p301 (SEQ ID NO: 301), or a combination thereof; and
   (b) administering an effective amount of the composition to the subject so as to treat kidney disease in the subject.

8. The method of claim 7, wherein the peptide of ApoB-100 is any one or more of peptides p2 (SEQ ID NO: 2), p11 (SEQ ID NO: 11), p32 (SEQ ID NO: 32), p45 (SEQ ID NO: 45), p74 (SEQ ID NO: 74), p102 (SEQ ID NO: 102), p148 (SEQ ID NO: 148), p162 (SEQ ID NO: 162), or p210 (SEQ ID NO: 210), or a combination thereof.

9. The method of claim 7, wherein the peptide of ApoB-100 is any one or more of peptides p2 (SEQ ID NO: 2), p45 (SEQ ID NO: 45), p74 (SEQ ID NO: 74), p102 (SEQ ID NO: 102), p210 (SEQ ID NO: 210), or a combination thereof.

10. The method of claim 7, wherein the peptide of ApoB-100 is p210 (SEQ ID NO: 210).

11. The method of claim 7, wherein the effective amount is between about 500,000 and about 2,000,000 activated CD8+ T cells.

12. The method of claim 7, wherein the effective amount is about 1,000,000 activated CD8+ T cells.

13. The method of claim 7, wherein the method further comprises administering an effective amount of one or more enhancers.

14. The method of claim 7, further comprising administering a composition comprising an immunogenic peptide of ApoB-100 or an immunogenically active portion thereof.

15. The method of claim 14, wherein the composition comprising activated CD8+ T cells and the composition comprising an immunogenic peptide of ApoB-100 or an immunogenically active portion thereof, are administered sequentially or concurrently.

* * * * *

```
                              SEQUENCE LISTING

<160> NUMBER OF SEQ ID NOS: 302

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Glu Glu Glu Met Leu Glu Asn Val Ser Leu Val Cys Pro Lys Asp Ala
1               5                   10                  15

Thr Arg Phe Lys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Ala Thr Arg Phe Lys His Leu Arg Lys Tyr Thr Tyr Asn Tyr Glu Ala
1               5                   10                  15

Glu Ser Ser Ser
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Ala Glu Ser Ser Ser Gly Val Pro Gly Thr Ala Asp Ser Arg Ser Ala
1               5                   10                  15

Thr Arg Ile Asn
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Ala Thr Arg Ile Asn Cys Lys Val Glu Leu Glu Val Pro Gln Leu Cys
1               5                   10                  15

Ser Phe Ile Leu
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 5

Cys Ser Phe Ile Leu Lys Thr Ser Gln Cys Thr Leu Lys Glu Val Tyr
1               5                   10                  15

Gly Phe Asn Pro
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Tyr Gly Phe Asn Pro Glu Gly Lys Ala Leu Leu Lys Lys Thr Lys Asn
1               5                   10                  15

Ser Glu Glu Phe
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Asn Ser Glu Glu Phe Ala Ala Ala Met Ser Arg Tyr Glu Leu Lys Leu
1               5                   10                  15

Ala Ile Pro Glu
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Leu Ala Ile Pro Glu Gly Lys Gln Val Phe Leu Tyr Pro Glu Lys Asp
1               5                   10                  15

Glu Pro Thr Tyr
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Asp Glu Pro Thr Tyr Ile Leu Asn Ile Lys Arg Gly Ile Ile Ser Ala
1               5                   10                  15

Leu Leu Val Pro
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 10

Ala Leu Leu Val Pro Pro Glu Thr Glu Glu Ala Lys Gln Val Leu Phe
1               5                   10                  15

Leu Asp Thr Val
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Phe Leu Asp Thr Val Tyr Gly Asn Cys Ser Thr His Phe Thr Val Lys
1               5                   10                  15

Thr Arg Lys Gly
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Lys Thr Arg Lys Gly Asn Val Ala Thr Glu Ile Ser Thr Glu Arg Asp
1               5                   10                  15

Leu Gly Gln Cys
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

Asp Leu Gly Gln Cys Asp Arg Phe Lys Pro Ile Arg Thr Gly Ile Ser
1               5                   10                  15

Pro Leu Ala Leu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide

<400> SEQUENCE: 14

Ser Pro Leu Ala Leu Ile Lys Gly Met Thr Arg Pro Leu Ser Thr Leu
1               5                   10                  15

Ile Ser Ser Ser
            20

<210> SEQ ID NO 15
<211> LENGTH: 20
<212> TYPE: PRT
<213> ORGANISM: Artificial Sequence
<220> FEATURE:
```

```
<223> OTHER INFORMATION: Synthetic peptide

<400> SEQUENCE: 15

Leu Ile Ser Ser Ser Gln Ser Cys Gln Tyr Thr Leu Asp Ala Lys Arg
1               5                   10                  15

Lys His Val Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Arg Lys His Val Ala Glu Ala Ile Cys Lys Glu Gln His Leu Phe Leu
1               5                   10                  15

Pro Phe Ser Tyr
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

Leu Pro Phe Ser Tyr Asn Asn Lys Tyr Gly Met Val Ala Gln Val Thr
1               5                   10                  15

Gln Thr Leu Lys
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide

<400> SEQUENCE: 18

Thr Gln Thr Leu Lys Leu Glu Asp Thr Pro Lys Ile Asn Ser Arg Phe
1               5                   10                  15

Phe Gly Glu Gly
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide

<400> SEQUENCE: 19

Phe Phe Gly Glu Gly Thr Lys Lys Met Gly Leu Ala Phe Glu Ser Thr
1               5                   10                  15

Lys Ser Thr Ser
            20

<210> SEQ ID NO 20
<211> LENGTH: 20
<212> TYPE: PRT
<213> ORGANISM: Artificial Sequence
```

<220> FEATURE:
<223> OTHER INFORMATION: Synthetic peptide

<400> SEQUENCE: 20

Thr Lys Ser Thr Ser Pro Pro Lys Gln Ala Glu Ala Val Leu Lys Thr
1               5                   10                  15

Leu Gln Glu Leu
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

Thr Leu Gln Glu Leu Lys Lys Leu Thr Ile Ser Glu Gln Asn Ile Gln
1               5                   10                  15

Arg Ala Asn Leu
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Gln Arg Ala Asn Leu Phe Asn Lys Leu Val Thr Glu Leu Arg Gly Leu
1               5                   10                  15

Ser Asp Glu Ala
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Leu Ser Asp Glu Ala Val Thr Ser Leu Leu Pro Gln Leu Ile Glu Val
1               5                   10                  15

Ser Ser Pro Ile
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

Val Ser Ser Pro Ile Thr Leu Gln Ala Leu Val Gln Cys Gly Gln Pro
1               5                   10                  15

Gln Cys Ser Thr
            20

<210> SEQ ID NO 25
<211> LENGTH: 20
<212> TYPE: PRT

```
<213> ORGANISM: Artificial Sequence
<220> FEATURE:
<223> OTHER INFORMATION: Synthetic peptide

<400> SEQUENCE: 25

Pro Gln Cys Ser Thr His Ile Leu Gln Trp Leu Lys Arg Val His Ala
1               5                   10                  15

Asn Pro Leu Leu
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Ala Asn Pro Leu Leu Ile Asp Val Val Thr Tyr Leu Val Ala Leu Ile
1               5                   10                  15

Pro Glu Pro Ser
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Ile Pro Glu Pro Ser Ala Gln Gln Leu Arg Glu Ile Phe Asn Met Ala
1               5                   10                  15

Arg Asp Gln Arg
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide

<400> SEQUENCE: 28

Ala Arg Asp Gln Arg Ser Arg Ala Thr Leu Tyr Ala Leu Ser His Ala
1               5                   10                  15

Val Asn Asn Tyr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Ala Val Asn Asn Tyr His Lys Thr Asn Pro Thr Gly Thr Gln Glu Leu
1               5                   10                  15

Leu Asp Ile Ala
            20

<210> SEQ ID NO 30
<211> LENGTH: 20
```

```
<212> TYPE: PRT
<213> ORGANISM: Artificial Sequence
<220> FEATURE:
<223> OTHER INFORMATION: Synthetic peptide

<400> SEQUENCE: 30

Leu Leu Asp Ile Ala Asn Tyr Leu Met Glu Gln Ile Gln Asp Cys
1               5                   10                  15

Thr Gly Asp Glu
            20

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide

<400> SEQUENCE: 31

Cys Thr Gly Asp Glu Asp Tyr Thr Tyr Leu Ile Leu Arg Val Ile Gly
1               5                   10                  15

Asn Met Gly Gln
            20

<210> SEQ ID NO 32
<211> LENGTH: 20
<212> TYPE: PRT
<213> ORGANISM: Artificial Sequence
<220> FEATURE:
<223> OTHER INFORMATION: Synthetic peptide

<400> SEQUENCE: 32

Gly Asn Met Gly Gln Thr Met Glu Gln Leu Thr Pro Glu Leu Lys Ser
1               5                   10                  15

Ser Ile Leu Lys
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

Ser Ser Ile Leu Lys Cys Val Gln Ser Thr Lys Pro Ser Leu Met Ile
1               5                   10                  15

Gln Lys Ala Ala
            20

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Ile Gln Lys Ala Ala Ile Gln Ala Leu Arg Lys Met Glu Pro Lys Asp
1               5                   10                  15

Lys Asp Gln Glu
            20

<210> SEQ ID NO 35
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Asp Lys Asp Gln Glu Val Leu Leu Gln Thr Phe Leu Asp Asp Ala Ser
1               5                   10                  15

Pro Gly Asp Lys
            20

<210> SEQ ID NO 36
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Ser Pro Gly Asp Lys Arg Leu Ala Ala Tyr Leu Met Leu Met Arg Ser
1               5                   10                  15

Pro Ser Gln Ala
            20

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide

<400> SEQUENCE: 37

Ser Pro Ser Gln Ala Asp Ile Asn Lys Ile Val Gln Ile Leu Pro Trp
1               5                   10                  15

Glu Gln Asn Glu
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide

<400> SEQUENCE: 38

Trp Glu Gln Asn Glu Gln Val Lys Asn Phe Val Ala Ser His Ile Ala
1               5                   10                  15

Asn Ile Leu Asn
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic peptide

<400> SEQUENCE: 39

Ala Asn Ile Leu Asn Ser Glu Glu Leu Asp Ile Gln Asp Leu Lys Lys
1               5                   10                  15

Leu Val Lys Glu
            20
```

```
<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40

Lys Leu Val Lys Glu Ala Leu Lys Glu Ser Gln Leu Pro Thr Val Met
1               5                   10                  15

Asp Phe Arg Lys
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide

<400> SEQUENCE: 41

Met Asp Phe Arg Lys Phe Ser Arg Asn Tyr Gln Leu Tyr Lys Ser Val
1               5                   10                  15

Ser Leu Pro Ser
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide

<400> SEQUENCE: 42

Val Ser Leu Pro Ser Leu Asp Pro Ala Ser Ala Lys Ile Glu Gly Asn
1               5                   10                  15

Leu Ile Phe Asp
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic peptide

<400> SEQUENCE: 43

Asn Leu Ile Phe Asp Pro Asn Asn Tyr Leu Pro Lys Glu Ser Met Leu
1               5                   10                  15

Lys Thr Thr Leu
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic peptide

<400> SEQUENCE: 44

Leu Lys Thr Thr Leu Thr Ala Phe Gly Phe Ala Ser Ala Asp Leu Ile
1               5                   10                  15

Glu Ile Gly Leu
            20
```

```
<210> SEQ ID NO 45
<211> LENGTH: 20
<212> TYPE: PRT
<213> ORGANISM: Artificial Sequence
<220> FEATURE:
<223> OTHER INFORMATION: Synthetic peptide

<400> SEQUENCE: 45

Ile Glu Ile Gly Leu Glu Gly Lys Gly Phe Glu Pro Thr Leu Glu Ala
1               5                   10                  15

Leu Phe Gly Lys
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Ala Leu Phe Gly Lys Gln Gly Phe Phe Pro Asp Ser Val Asn Lys Ala
1               5                   10                  15

Leu Tyr Trp Val
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic peptide

<400> SEQUENCE: 47

Ala Leu Tyr Trp Val Asn Gly Gln Val Pro Asp Gly Val Ser Lys Val
1               5                   10                  15

Leu Val Asp His
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

Val Leu Val Asp His Phe Gly Tyr Thr Lys Asp Lys His Glu Gln
1               5                   10                  15

Asp Met Val Asn
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic peptide

<400> SEQUENCE: 49

Gln Asp Met Val Asn Gly Ile Met Leu Ser Val Glu Lys Leu Ile Lys
1               5                   10                  15

Asp Leu Lys Ser
            20
```

```
<210> SEQ ID NO 50
<211> LENGTH: 20
<212> TYPE: PRT
<213> ORGANISM: Artificial Sequence
<220> FEATURE:
<223> OTHER INFORMATION: Synthetic peptide

<400> SEQUENCE: 50

Lys Asp Leu Lys Ser Lys Glu Val Pro Glu Ala Arg Ala Tyr Leu Arg
1               5                   10                  15

Ile Leu Gly Glu
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic peptide

<400> SEQUENCE: 51

Arg Ile Leu Gly Glu Glu Leu Gly Phe Ala Ser Leu His Asp Leu Gln
1               5                   10                  15

Leu Leu Gly Lys
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Gln Leu Leu Gly Lys Leu Leu Leu Met Gly Ala Arg Thr Leu Gln Gly
1               5                   10                  15

Ile Pro Gln Met
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic peptide

<400> SEQUENCE: 53

Gly Ile Pro Gln Met Ile Gly Glu Val Ile Arg Lys Gly Ser Lys Asn
1               5                   10                  15

Asp Phe Phe Leu
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic peptide

<400> SEQUENCE: 54

Asn Asp Phe Phe Leu His Tyr Ile Phe Met Glu Asn Ala Phe Glu Leu
1               5                   10                  15

Pro Thr Gly Ala
```

20

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Leu Pro Thr Gly Ala Gly Leu Gln Leu Gln Ile Ser Ser Ser Gly Val
1               5                   10                  15

Ile Ala Pro Gly
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Val Ile Ala Pro Gly Ala Lys Ala Gly Val Lys Leu Glu Val Ala Asn
1               5                   10                  15

Met Gln Ala Glu
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic peptide

<400> SEQUENCE: 57

Asn Met Gln Ala Glu Leu Val Ala Lys Pro Ser Val Ser Val Glu Phe
1               5                   10                  15

Val Thr Asn Met
            20

<210> SEQ ID NO 58
<211> LENGTH: 20
<212> TYPE: PRT
<213> ORGANISM: Artificial Sequence
<220> FEATURE:
<223> OTHER INFORMATION: Synthetic peptide

<400> SEQUENCE: 58

Phe Val Thr Asn Met Gly Ile Ile Ile Pro Asp Phe Ala Arg Ser Gly
1               5                   10                  15

Val Gln Met Asn
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide

<400> SEQUENCE: 59

Gly Val Gln Met Asn Thr Asn Phe Phe His Glu Ser Gly Leu Glu Ala
1               5                   10                  15

His Val Ala Leu
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic peptide

<400> SEQUENCE: 60

Ala His Val Ala Leu Lys Ala Gly Lys Leu Lys Phe Ile Ile Pro Ser
1               5                   10                  15

Pro Lys Arg Pro
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic peptide

<400> SEQUENCE: 61

Ser Pro Lys Arg Pro Val Lys Leu Leu Ser Gly Gly Asn Thr Leu His
1               5                   10                  15

Leu Val Ser Thr
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic peptide

<400> SEQUENCE: 62

His Leu Val Ser Thr Thr Lys Thr Glu Val Ile Pro Pro Leu Ile Glu
1               5                   10                  15

Asn Arg Gln Ser
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic peptide

<400> SEQUENCE: 63

Glu Asn Arg Gln Ser Trp Ser Val Cys Lys Gln Val Phe Pro Gly Leu
1               5                   10                  15

Asn Tyr Cys Thr
            20

<210> SEQ ID NO 64
<211> LENGTH: 20
<212> TYPE: PRT
<213> ORGANISM: Artificial Sequence
<220> FEATURE:
<223> OTHER INFORMATION: Synthetic peptide

<400> SEQUENCE: 64

Leu Asn Tyr Cys Thr Ser Gly Ala Tyr Ser Asn Ala Ser Ser Thr Asp
1               5                   10                  15

```
Ser Ala Ser Tyr
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic peptide

<400> SEQUENCE: 65

Asp Ser Ala Ser Tyr Tyr Pro Leu Thr Gly Asp Thr Arg Leu Glu Leu
1               5                   10                  15

Glu Leu Arg Pro
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide

<400> SEQUENCE: 66

Leu Glu Leu Arg Pro Thr Gly Glu Ile Glu Gln Tyr Ser Val Ser Ala
1               5                   10                  15

Thr Tyr Glu Leu
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic peptide

<400> SEQUENCE: 67

Ala Thr Tyr Glu Leu Gln Arg Glu Asp Arg Ala Leu Val Asp Thr Leu
1               5                   10                  15

Lys Phe Val Thr
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic peptide

<400> SEQUENCE: 68

Leu Lys Phe Val Thr Gln Ala Glu Gly Ala Lys Gln Thr Glu Ala Thr
1               5                   10                  15

Met Thr Phe Lys
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide

<400> SEQUENCE: 69

Thr Met Thr Phe Lys Tyr Asn Arg Gln Ser Met Thr Leu Ser Ser Glu
```

```
                1               5                  10                  15
Val Gln Ile Pro
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic peptide

<400> SEQUENCE: 70

Glu Val Gln Ile Pro Asp Phe Asp Val Asp Leu Gly Thr Ile Leu Arg
1               5                  10                  15

Val Asn Asp Glu
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide

<400> SEQUENCE: 71

Arg Val Asn Asp Glu Ser Thr Glu Gly Lys Thr Ser Tyr Arg Leu Thr
1               5                  10                  15

Leu Asp Ile Gln
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic peptide

<400> SEQUENCE: 72

Thr Leu Asp Ile Gln Asn Lys Lys Ile Thr Glu Val Ala Leu Met Gly
1               5                  10                  15

His Leu Ser Cys
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic peptide

<400> SEQUENCE: 73

Gly His Leu Ser Cys Asp Thr Lys Glu Glu Arg Lys Ile Lys Gly Val
1               5                  10                  15

Ile Ser Ile Pro
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic peptide

<400> SEQUENCE: 74
```

```
Val Ile Ser Ile Pro Arg Leu Gln Ala Glu Ala Arg Ser Glu Ile Leu
1               5                   10                  15

Ala His Trp Ser
            20
```

<210> SEQ ID NO 75
<211> LENGTH: 20
<212> TYPE: PRT
<213> ORGANISM: Artificial Sequence
<220> FEATURE:
<223> OTHER INFORMATION: Synthetic peptide

<400> SEQUENCE: 75

```
Leu Ala His Trp Ser Pro Ala Lys Leu Leu Leu Gln Met Asp Ser Ser
1               5                   10                  15

Ala Thr Ala Tyr
            20
```

<210> SEQ ID NO 76
<211> LENGTH: 20
<212> TYPE: PRT
<213> ORGANISM: Artificial Sequence
<220> FEATURE:
<223> OTHER INFORMATION: Synthetic peptide

<400> SEQUENCE: 76

```
Ser Ala Thr Ala Tyr Gly Ser Thr Val Ser Lys Arg Val Ala Trp His
1               5                   10                  15

Tyr Asp Glu Glu
            20
```

<210> SEQ ID NO 77
<211> LENGTH: 20
<212> TYPE: PRT
<213> ORGANISM: Artificial Sequence
<220> FEATURE:
<223> OTHER INFORMATION: Synthetic peptide

<400> SEQUENCE: 77

```
His Tyr Asp Glu Glu Lys Ile Glu Phe Glu Trp Asn Thr Gly Thr Asn
1               5                   10                  15

Val Asp Thr Lys
            20
```

<210> SEQ ID NO 78
<211> LENGTH: 20
<212> TYPE: PRT
<213> ORGANISM: Artificial Sequence
<220> FEATURE:
<223> OTHER INFORMATION: Synthetic peptide

<400> SEQUENCE: 78

```
Asn Val Asp Thr Lys Lys Met Thr Ser Asn Phe Pro Val Asp Leu Ser
1               5                   10                  15

Asp Tyr Pro Lys
            20
```

<210> SEQ ID NO 79
<211> LENGTH: 20
<212> TYPE: PRT
<213> ORGANISM: Artificial Sequence
<220> FEATURE:
<223> OTHER INFORMATION: Synthetic peptide

<400> SEQUENCE: 79

```
Ser Asp Tyr Pro Lys Ser Leu His Met Tyr Ala Asn Arg Leu Leu Asp
1               5                   10                  15

His Arg Val Pro
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic peptide

<400> SEQUENCE: 80

Asp His Arg Val Pro Glu Thr Asp Met Thr Phe Arg His Val Gly Ser
1               5                   10                  15

Lys Leu Ile Val
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic peptide

<400> SEQUENCE: 81

Ser Lys Leu Ile Val Ala Met Ser Ser Trp Leu Gln Lys Ala Ser Gly
1               5                   10                  15

Ser Leu Pro Tyr
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic peptide

<400> SEQUENCE: 82

Gly Ser Leu Pro Tyr Thr Gln Thr Leu Gln Asp His Leu Asn Ser Leu
1               5                   10                  15

Lys Glu Phe Asn
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic peptide

<400> SEQUENCE: 83

Leu Lys Glu Phe Asn Leu Gln Asn Met Gly Leu Pro Asp Phe His Ile
1               5                   10                  15

Pro Glu Asn Leu
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic peptide
```

-continued

```
<400> SEQUENCE: 84

Ile Pro Glu Asn Leu Phe Leu Lys Ser Asp Gly Arg Val Lys Tyr Thr
1               5                   10                  15

Leu Asn Lys Asn
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic peptide

<400> SEQUENCE: 85

Thr Leu Asn Lys Asn Ser Leu Lys Ile Glu Ile Pro Leu Pro Phe Gly
1               5                   10                  15

Gly Lys Ser Ser
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic peptide

<400> SEQUENCE: 86

Gly Gly Lys Ser Ser Arg Asp Leu Lys Met Leu Glu Thr Val Arg Thr
1               5                   10                  15

Pro Ala Leu His
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic peptide

<400> SEQUENCE: 87

Thr Pro Ala Leu His Phe Lys Ser Val Gly Phe His Leu Pro Ser Arg
1               5                   10                  15

Glu Phe Gln Val
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic peptide

<400> SEQUENCE: 88

Arg Glu Phe Gln Val Pro Thr Phe Thr Ile Pro Lys Leu Tyr Gln Leu
1               5                   10                  15

Gln Val Pro Leu
            20

<210> SEQ ID NO 89
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 89

Leu Gln Val Pro Leu Leu Gly Val Leu Asp Leu Ser Thr Asn Val Tyr
1               5                   10                  15

Ser Asn Leu Tyr
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic peptide

<400> SEQUENCE: 90

Tyr Ser Asn Leu Tyr Asn Trp Ser Ala Ser Tyr Ser Gly Gly Asn Thr
1               5                   10                  15

Ser Thr Asp His
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic peptide

<400> SEQUENCE: 91

Thr Ser Thr Asp His Phe Ser Leu Arg Ala Arg Tyr His Met Lys Ala
1               5                   10                  15

Asp Ser Val Val
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic peptide

<400> SEQUENCE: 92

Ala Asp Ser Val Val Asp Leu Leu Ser Tyr Asn Val Gln Gly Ser Gly
1               5                   10                  15

Glu Thr Thr Tyr
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic peptide

<400> SEQUENCE: 93

Gly Glu Thr Thr Tyr Asp His Lys Asn Thr Phe Thr Leu Ser Cys Asp
1               5                   10                  15

Gly Ser Leu Arg
            20

<210> SEQ ID NO 94
<211> LENGTH: 20
<212> TYPE: PRT
<213> ORGANISM: Artificial Sequence
<220> FEATURE:

<223> OTHER INFORMATION: Synthetic peptide

<400> SEQUENCE: 94

Asp Gly Ser Leu Arg His Lys Phe Leu Asp Ser Asn Ile Lys Phe Ser
1               5                   10                  15

His Val Glu Lys
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic peptide

<400> SEQUENCE: 95

Ser His Val Glu Lys Leu Gly Asn Asn Pro Val Ser Lys Gly Leu Leu
1               5                   10                  15

Ile Phe Asp Ala
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic peptide

<400> SEQUENCE: 96

Leu Ile Phe Asp Ala Ser Ser Ser Trp Gly Pro Gln Met Ser Ala Ser
1               5                   10                  15

Val His Leu Asp
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic peptide

<400> SEQUENCE: 97

Ser Val His Leu Asp Ser Lys Lys Lys Gln His Leu Phe Val Lys Glu
1               5                   10                  15

Val Lys Ile Asp
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic peptide

<400> SEQUENCE: 98

Glu Val Lys Ile Asp Gly Gln Phe Arg Val Ser Ser Phe Tyr Ala Lys
1               5                   10                  15

Gly Thr Tyr Gly
            20

<210> SEQ ID NO 99
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 99

Lys Gly Thr Tyr Gly Leu Ser Cys Gln Arg Asp Pro Asn Thr Gly Arg
1               5                   10                  15

Leu Asn Gly Glu
            20

<210> SEQ ID NO 100
<211> LENGTH: 20
<212> TYPE: PRT
<213> ORGANISM: Artificial Sequence
<220> FEATURE:
<223> OTHER INFORMATION: Synthetic peptide

<400> SEQUENCE: 100

Arg Leu Asn Gly Glu Ser Asn Leu Arg Phe Asn Ser Ser Tyr Leu Gln
1               5                   10                  15

Gly Thr Asn Gln
            20

<210> SEQ ID NO 101
<211> LENGTH: 20
<212> TYPE: PRT
<213> ORGANISM: Artificial Sequence
<220> FEATURE:
<223> OTHER INFORMATION: Synthetic peptide

<400> SEQUENCE: 101

Gln Gly Thr Asn Gln Ile Thr Gly Arg Tyr Glu Asp Gly Thr Leu Ser
1               5                   10                  15

Leu Thr Ser Thr
            20

<210> SEQ ID NO 102
<211> LENGTH: 20
<212> TYPE: PRT
<213> ORGANISM: Artificial Sequence
<220> FEATURE:
<223> OTHER INFORMATION: Synthetic peptide

<400> SEQUENCE: 102

Ser Leu Thr Ser Thr Ser Asp Leu Gln Ser Gly Ile Ile Lys Asn Thr
1               5                   10                  15

Ala Ser Leu Lys
            20

<210> SEQ ID NO 103
<211> LENGTH: 20
<212> TYPE: PRT
<213> ORGANISM: Artificial Sequence
<220> FEATURE:
<223> OTHER INFORMATION: Synthetic peptide

<400> SEQUENCE: 103

Thr Ala Ser Leu Lys Tyr Glu Asn Tyr Glu Leu Thr Leu Lys Ser Asp
1               5                   10                  15

Thr Asn Gly Lys
            20

<210> SEQ ID NO 104
<211> LENGTH: 20
<212> TYPE: PRT
```

<213> ORGANISM: Artificial Sequence
<220> FEATURE:
<223> OTHER INFORMATION: Synthetic peptide

<400> SEQUENCE: 104

Asp Thr Asn Gly Lys Tyr Lys Asn Phe Ala Thr Ser Asn Lys Met Asp
1               5                   10                  15

Met Thr Phe Ser
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic peptide

<400> SEQUENCE: 105

Asp Met Thr Phe Ser Lys Gln Asn Ala Leu Leu Arg Ser Glu Tyr Gln
1               5                   10                  15

Ala Asp Tyr Glu
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic peptide

<400> SEQUENCE: 106

Gln Ala Asp Tyr Glu Ser Leu Arg Phe Phe Ser Leu Leu Ser Gly Ser
1               5                   10                  15

Leu Asn Ser His
            20

<210> SEQ ID NO 107
<211> LENGTH: 20
<212> TYPE: PRT
<213> ORGANISM: Artificial Sequence
<220> FEATURE:
<223> OTHER INFORMATION: Synthetic peptide

<400> SEQUENCE: 107

Ser Leu Asn Ser His Gly Leu Glu Leu Asn Ala Asp Ile Leu Gly Thr
1               5                   10                  15

Asp Lys Ile Asn
            20

<210> SEQ ID NO 108
<211> LENGTH: 20
<212> TYPE: PRT
<213> ORGANISM: Artificial Sequence
<220> FEATURE:
<223> OTHER INFORMATION: Synthetic peptide

<400> SEQUENCE: 108

Thr Asp Lys Ile Asn Ser Gly Ala His Lys Ala Thr Leu Arg Ile Gly
1               5                   10                  15

Gln Asp Gly Ile
            20

<210> SEQ ID NO 109
<211> LENGTH: 20

```
<212> TYPE: PRT
<213> ORGANISM: Artificial Sequence
<220> FEATURE:
<223> OTHER INFORMATION: Synthetic peptide

<400> SEQUENCE: 109

Gly Gln Asp Gly Ile Ser Thr Ser Ala Thr Thr Asn Leu Lys Cys Ser
1               5                   10                  15

Leu Leu Val Leu
            20

<210> SEQ ID NO 110
<211> LENGTH: 20
<212> TYPE: PRT
<213> ORGANISM: Artificial Sequence
<220> FEATURE:
<223> OTHER INFORMATION: Synthetic peptide

<400> SEQUENCE: 110

Ser Leu Leu Val Leu Glu Asn Glu Leu Asn Ala Glu Leu Gly Leu Ser
1               5                   10                  15

Gly Ala Ser Met
            20

<210> SEQ ID NO 111
<211> LENGTH: 20
<212> TYPE: PRT
<213> ORGANISM: Artificial Sequence
<220> FEATURE:
<223> OTHER INFORMATION: Synthetic peptide

<400> SEQUENCE: 111

Ser Gly Ala Ser Met Lys Leu Thr Thr Asn Gly Arg Phe Arg Glu His
1               5                   10                  15

Asn Ala Lys Phe
            20

<210> SEQ ID NO 112
<211> LENGTH: 20
<212> TYPE: PRT
<213> ORGANISM: Artificial Sequence
<220> FEATURE:
<223> OTHER INFORMATION: Synthetic peptide

<400> SEQUENCE: 112

His Asn Ala Lys Phe Ser Leu Asp Gly Lys Ala Ala Leu Thr Glu Leu
1               5                   10                  15

Ser Leu Gly Ser
            20

<210> SEQ ID NO 113
<211> LENGTH: 20
<212> TYPE: PRT
<213> ORGANISM: Artificial Sequence
<220> FEATURE:
<223> OTHER INFORMATION: Synthetic peptide

<400> SEQUENCE: 113

Leu Ser Leu Gly Ser Ala Tyr Gln Ala Met Ile Leu Gly Val Asp Ser
1               5                   10                  15

Lys Asn Ile Phe
            20

<210> SEQ ID NO 114
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 114

Ser Lys Asn Ile Phe Asn Phe Lys Val Ser Gln Glu Gly Leu Lys Leu
1               5                   10                  15

Ser Asn Asp Met
            20

<210> SEQ ID NO 115
<211> LENGTH: 20
<212> TYPE: PRT
<213> ORGANISM: Artificial Sequence
<220> FEATURE:
<223> OTHER INFORMATION: Synthetic peptide

<400> SEQUENCE: 115

Leu Ser Asn Asp Met Met Gly Ser Tyr Ala Glu Met Lys Phe Asp His
1               5                   10                  15

Thr Asn Ser Leu
            20

<210> SEQ ID NO 116
<211> LENGTH: 20
<212> TYPE: PRT
<213> ORGANISM: Artificial Sequence
<220> FEATURE:
<223> OTHER INFORMATION: Synthetic peptide

<400> SEQUENCE: 116

His Thr Asn Ser Leu Asn Ile Ala Gly Leu Ser Leu Asp Phe Ser Ser
1               5                   10                  15

Lys Leu Asp Asn
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic peptide

<400> SEQUENCE: 117

Ser Lys Leu Asp Asn Ile Tyr Ser Ser Asp Lys Phe Tyr Lys Gln Thr
1               5                   10                  15

Val Asn Leu Gln
            20

<210> SEQ ID NO 118
<211> LENGTH: 20
<212> TYPE: PRT
<213> ORGANISM: Artificial Sequence
<220> FEATURE:
<223> OTHER INFORMATION: Synthetic peptide

<400> SEQUENCE: 118

Thr Val Asn Leu Gln Leu Gln Pro Tyr Ser Leu Val Thr Thr Leu Asn
1               5                   10                  15

Ser Asp Leu Lys
            20
```

```
<210> SEQ ID NO 119
<211> LENGTH: 20
<212> TYPE: PRT
<213> ORGANISM: Artificial Sequence
<220> FEATURE:
<223> OTHER INFORMATION: Synthetic peptide

<400> SEQUENCE: 119

Asn Ser Asp Leu Lys Tyr Asn Ala Leu Asp Leu Thr Asn Asn Gly Lys
1               5                   10                  15

Leu Arg Leu Glu
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic peptide

<400> SEQUENCE: 120

Lys Leu Arg Leu Glu Pro Leu Lys Leu His Val Ala Gly Asn Leu Lys
1               5                   10                  15

Gly Ala Tyr Gln
            20

<210> SEQ ID NO 121
<211> LENGTH: 20
<212> TYPE: PRT
<213> ORGANISM: Artificial Sequence
<220> FEATURE:
<223> OTHER INFORMATION: Synthetic peptide

<400> SEQUENCE: 121

Lys Gly Ala Tyr Gln Asn Asn Glu Ile Lys His Ile Tyr Ala Ile Ser
1               5                   10                  15

Ser Ala Ala Leu
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic peptide

<400> SEQUENCE: 122

Ser Ser Ala Ala Leu Ser Ala Ser Tyr Lys Ala Asp Thr Val Ala Lys
1               5                   10                  15

Val Gln Gly Val
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic peptide

<400> SEQUENCE: 123

Lys Val Gln Gly Val Glu Phe Ser His Arg Leu Asn Thr Asp Ile Ala
1               5                   10                  15

Gly Leu Ala Ser
            20
```

<210> SEQ ID NO 124
<211> LENGTH: 20
<212> TYPE: PRT
<213> ORGANISM: Artificial Sequence
<220> FEATURE:
<223> OTHER INFORMATION: Synthetic peptide

<400> SEQUENCE: 124

Ala Gly Leu Ala Ser Ala Ile Asp Met Ser Thr Asn Tyr Asn Ser Asp
1               5                   10                  15

Ser Leu His Phe
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic peptide

<400> SEQUENCE: 125

Asp Ser Leu His Phe Ser Asn Val Phe Arg Ser Val Met Ala Pro Phe
1               5                   10                  15

Thr Met Thr Ile
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic peptide

<400> SEQUENCE: 126

Phe Thr Met Thr Ile Asp Ala His Thr Asn Gly Asn Gly Lys Leu Ala
1               5                   10                  15

Leu Trp Gly Glu
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic peptide

<400> SEQUENCE: 127

Ala Leu Trp Gly Glu His Thr Gly Gln Leu Tyr Ser Lys Phe Leu Leu
1               5                   10                  15

Lys Ala Glu Pro
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic peptide

<400> SEQUENCE: 128

Leu Lys Ala Glu Pro Leu Ala Phe Thr Phe Ser His Asp Tyr Lys Gly
1               5                   10                  15

Ser Thr Ser His
            20

```
<210> SEQ ID NO 129
<211> LENGTH: 20
<212> TYPE: PRT
<213> ORGANISM: Artificial Sequence
<220> FEATURE:
<223> OTHER INFORMATION: Synthetic peptide

<400> SEQUENCE: 129

Gly Ser Thr Ser His His Leu Val Ser Arg Lys Ser Ile Ser Ala Ala
1               5                   10                  15

Leu Glu His Lys
            20

<210> SEQ ID NO 130
<211> LENGTH: 20
<212> TYPE: PRT
<213> ORGANISM: Artificial Sequence
<220> FEATURE:
<223> OTHER INFORMATION: Synthetic peptide

<400> SEQUENCE: 130

Ala Leu Glu His Lys Val Ser Ala Leu Leu Thr Pro Ala Glu Gln Thr
1               5                   10                  15

Gly Thr Trp Lys
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic peptide

<400> SEQUENCE: 131

Thr Gly Thr Trp Lys Leu Lys Thr Gln Phe Asn Asn Asn Glu Tyr Ser
1               5                   10                  15

Gln Asp Leu Asp
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide

<400> SEQUENCE: 132

Ser Gln Asp Leu Asp Ala Tyr Asn Thr Lys Asp Lys Ile Gly Val Glu
1               5                   10                  15

Leu Thr Gly Arg
            20

<210> SEQ ID NO 133
<211> LENGTH: 20
<212> TYPE: PRT
<213> ORGANISM: Artificial Sequence
<220> FEATURE:
<223> OTHER INFORMATION: Synthetic peptide

<400> SEQUENCE: 133

Glu Leu Thr Gly Arg Thr Leu Ala Asp Leu Thr Leu Leu Asp Ser Pro
1               5                   10                  15

Ile Lys Val Pro
```

```
<210> SEQ ID NO 134
<211> LENGTH: 20
<212> TYPE: PRT
<213> ORGANISM: Artificial Sequence
<220> FEATURE:
<223> OTHER INFORMATION: Synthetic peptide

<400> SEQUENCE: 134

Pro Ile Lys Val Pro Leu Leu Leu Ser Glu Pro Ile Asn Ile Ile Asp
1               5                   10                  15

Ala Leu Glu Met
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic peptide

<400> SEQUENCE: 135

Asp Ala Leu Glu Met Arg Asp Ala Val Glu Lys Pro Gln Glu Phe Thr
1               5                   10                  15

Ile Val Ala Phe
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic peptide

<400> SEQUENCE: 136

Thr Ile Val Ala Phe Val Lys Tyr Asp Lys Asn Gln Asp Val His Ser
1               5                   10                  15

Ile Asn Leu Pro
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic peptide

<400> SEQUENCE: 137

Ser Ile Asn Leu Pro Phe Phe Glu Thr Leu Gln Glu Tyr Phe Glu Arg
1               5                   10                  15

Asn Arg Gln Thr
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic peptide

<400> SEQUENCE: 138

Arg Asn Arg Gln Thr Ile Ile Val Val Val Glu Asn Val Gln Arg Asn
1               5                   10                  15
```

Leu Lys His Ile
            20

<210> SEQ ID NO 139
<211> LENGTH: 20
<212> TYPE: PRT
<213> ORGANISM: Artificial Sequence
<220> FEATURE:
<223> OTHER INFORMATION: Synthetic peptide

<400> SEQUENCE: 139

Asn Leu Lys His Ile Asn Ile Asp Gln Phe Val Arg Lys Tyr Arg Ala
1               5                   10                  15

Ala Leu Gly Lys
            20

<210> SEQ ID NO 140
<211> LENGTH: 20
<212> TYPE: PRT
<213> ORGANISM: Artificial Sequence
<220> FEATURE:
<223> OTHER INFORMATION: Synthetic peptide

<400> SEQUENCE: 140

Ala Ala Leu Gly Lys Leu Pro Gln Gln Ala Asn Asp Tyr Leu Asn Ser
1               5                   10                  15

Phe Asn Trp Glu
            20

<210> SEQ ID NO 141
<211> LENGTH: 20
<212> TYPE: PRT
<213> ORGANISM: Artificial Sequence
<220> FEATURE:
<223> OTHER INFORMATION: Synthetic peptide

<400> SEQUENCE: 141

Ser Phe Asn Trp Glu Arg Gln Val Ser His Ala Lys Glu Lys Leu Thr
1               5                   10                  15

Ala Leu Thr Lys
            20

<210> SEQ ID NO 142
<211> LENGTH: 20
<212> TYPE: PRT
<213> ORGANISM: Artificial Sequence
<220> FEATURE:
<223> OTHER INFORMATION: Synthetic peptide

<400> SEQUENCE: 142

Thr Ala Leu Thr Lys Lys Tyr Arg Ile Thr Glu Asn Asp Ile Gln Ile
1               5                   10                  15

Ala Leu Asp Asp
            20

<210> SEQ ID NO 143
<211> LENGTH: 20
<212> TYPE: PRT
<213> ORGANISM: Artificial Sequence
<220> FEATURE:
<223> OTHER INFORMATION: Synthetic peptide

<400> SEQUENCE: 143

Ile Ala Leu Asp Asp Ala Lys Ile Asn Phe Asn Glu Lys Leu Ser Gln
1               5                   10                  15

```
Leu Gln Thr Tyr
            20

<210> SEQ ID NO 144
<211> LENGTH: 20
<212> TYPE: PRT
<213> ORGANISM: Artificial Sequence
<220> FEATURE:
<223> OTHER INFORMATION: Synthetic peptide

<400> SEQUENCE: 144

Gln Leu Gln Thr Tyr Met Ile Gln Phe Asp Gln Tyr Ile Lys Asp Ser
1               5                   10                  15

Tyr Asp Leu His
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic peptide

<400> SEQUENCE: 145

Ser Tyr Asp Leu His Asp Leu Lys Ile Ala Ile Ala Asn Ile Ile Asp
1               5                   10                  15

Glu Ile Ile Glu
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic peptide

<400> SEQUENCE: 146

Asp Glu Ile Ile Glu Lys Leu Lys Ser Leu Asp Glu His Tyr His Ile
1               5                   10                  15

Arg Val Asn Leu
            20

<210> SEQ ID NO 147
<211> LENGTH: 20
<212> TYPE: PRT
<213> ORGANISM: Artificial Sequence
<220> FEATURE:
<223> OTHER INFORMATION: Synthetic peptide

<400> SEQUENCE: 147

Ile Arg Val Asn Leu Val Lys Thr Ile His Asp Leu His Leu Phe Ile
1               5                   10                  15

Glu Asn Ile Asp
            20

<210> SEQ ID NO 148
<211> LENGTH: 20
<212> TYPE: PRT
<213> ORGANISM: Artificial Sequence
<220> FEATURE:
<223> OTHER INFORMATION: Synthetic peptide

<400> SEQUENCE: 148

Ile Glu Asn Ile Asp Phe Asn Lys Ser Gly Ser Ser Thr Ala Ser Trp
```

```
1               5                   10                  15

Ile Gln Asn Val
            20

<210> SEQ ID NO 149
<211> LENGTH: 20
<212> TYPE: PRT
<213> ORGANISM: Artificial Sequence
<220> FEATURE:
<223> OTHER INFORMATION: Synthetic peptide

<400> SEQUENCE: 149

Trp Ile Gln Asn Val Asp Thr Lys Tyr Gln Ile Arg Ile Gln Ile Gln
1               5                   10                  15

Glu Lys Leu Gln
            20

<210> SEQ ID NO 150
<211> LENGTH: 20
<212> TYPE: PRT
<213> ORGANISM: Artificial Sequence
<220> FEATURE:
<223> OTHER INFORMATION: Synthetic peptide

<400> SEQUENCE: 150

Gln Glu Lys Leu Gln Gln Leu Lys Arg His Ile Gln Asn Ile Asp Ile
1               5                   10                  15

Gln His Leu Ala
            20

<210> SEQ ID NO 151
<211> LENGTH: 20
<212> TYPE: PRT
<213> ORGANISM: Artificial Sequence
<220> FEATURE:
<223> OTHER INFORMATION: Synthetic peptide

<400> SEQUENCE: 151

Ile Gln His Leu Ala Gly Lys Leu Lys Gln His Ile Glu Ala Ile Asp
1               5                   10                  15

Val Arg Val Leu
            20

<210> SEQ ID NO 152
<211> LENGTH: 20
<212> TYPE: PRT
<213> ORGANISM: Artificial Sequence
<220> FEATURE:
<223> OTHER INFORMATION: Synthetic peptide

<400> SEQUENCE: 152

Asp Val Arg Val Leu Leu Asp Gln Leu Gly Thr Thr Ile Ser Phe Glu
1               5                   10                  15

Arg Ile Asn Asp
            20

<210> SEQ ID NO 153
<211> LENGTH: 20
<212> TYPE: PRT
<213> ORGANISM: Artificial Sequence
<220> FEATURE:
<223> OTHER INFORMATION: Synthetic peptide

<400> SEQUENCE: 153
```

```
Glu Arg Ile Asn Asp Val Leu Glu His Val Lys His Phe Val Ile Asn
1               5                   10                  15

Leu Ile Gly Asp
            20
```

<210> SEQ ID NO 154
<211> LENGTH: 20
<212> TYPE: PRT
<213> ORGANISM: Artificial Sequence
<220> FEATURE:
<223> OTHER INFORMATION: Synthetic peptide

<400> SEQUENCE: 154

```
Asn Leu Ile Gly Asp Phe Glu Val Ala Glu Lys Ile Asn Ala Phe Arg
1               5                   10                  15

Ala Lys Val His
            20
```

<210> SEQ ID NO 155
<211> LENGTH: 20
<212> TYPE: PRT
<213> ORGANISM: Artificial Sequence
<220> FEATURE:
<223> OTHER INFORMATION: Synthetic peptide

<400> SEQUENCE: 155

```
Arg Ala Lys Val His Glu Leu Ile Glu Arg Tyr Glu Val Asp Gln Gln
1               5                   10                  15

Ile Gln Val Leu
            20
```

<210> SEQ ID NO 156
<211> LENGTH: 20
<212> TYPE: PRT
<213> ORGANISM: Artificial Sequence
<220> FEATURE:
<223> OTHER INFORMATION: Synthetic peptide

<400> SEQUENCE: 156

```
Gln Ile Gln Val Leu Met Asp Lys Leu Val Glu Leu Thr His Gln Tyr
1               5                   10                  15

Lys Leu Lys Glu
            20
```

<210> SEQ ID NO 157
<211> LENGTH: 20
<212> TYPE: PRT
<213> ORGANISM: Artificial Sequence
<220> FEATURE:
<223> OTHER INFORMATION: Synthetic peptide

<400> SEQUENCE: 157

```
Tyr Lys Leu Lys Glu Thr Ile Gln Lys Leu Ser Asn Val Leu Gln Gln
1               5                   10                  15

Val Lys Ile Lys
            20
```

<210> SEQ ID NO 158
<211> LENGTH: 20
<212> TYPE: PRT
<213> ORGANISM: Artificial Sequence
<220> FEATURE:
<223> OTHER INFORMATION: Synthetic peptide

<400> SEQUENCE: 158

Gln Val Lys Ile Lys Asp Tyr Phe Glu Lys Leu Val Gly Phe Ile Asp
1               5                   10                  15

Asp Ala Val Lys
            20

<210> SEQ ID NO 159
<211> LENGTH: 20
<212> TYPE: PRT
<213> ORGANISM: Artificial Sequence
<220> FEATURE:
<223> OTHER INFORMATION: Synthetic peptide

<400> SEQUENCE: 159

Asp Asp Ala Val Lys Lys Leu Asn Glu Leu Ser Phe Lys Thr Phe Ile
1               5                   10                  15

Glu Asp Val Asn
            20

<210> SEQ ID NO 160
<211> LENGTH: 20
<212> TYPE: PRT
<213> ORGANISM: Artificial Sequence
<220> FEATURE:
<223> OTHER INFORMATION: Synthetic peptide

<400> SEQUENCE: 160

Ile Glu Asp Val Asn Lys Phe Leu Asp Met Leu Ile Lys Lys Leu Lys
1               5                   10                  15

Ser Phe Asp Tyr
            20

<210> SEQ ID NO 161
<211> LENGTH: 20
<212> TYPE: PRT
<213> ORGANISM: Artificial Sequence
<220> FEATURE:
<223> OTHER INFORMATION: Synthetic peptide

<400> SEQUENCE: 161

Lys Ser Phe Asp Tyr His Gln Phe Val Asp Glu Thr Asn Asp Lys Ile
1               5                   10                  15

Arg Glu Val Thr
            20

<210> SEQ ID NO 162
<211> LENGTH: 20
<212> TYPE: PRT
<213> ORGANISM: Artificial Sequence
<220> FEATURE:
<223> OTHER INFORMATION: Synthetic peptide

<400> SEQUENCE: 162

Ile Arg Glu Val Thr Gln Arg Leu Asn Gly Glu Ile Gln Ala Leu Glu
1               5                   10                  15

Leu Pro Gln Lys
            20

<210> SEQ ID NO 163
<211> LENGTH: 20
<212> TYPE: PRT
<213> ORGANISM: Artificial Sequence
<220> FEATURE:
<223> OTHER INFORMATION: Synthetic peptide

<400> SEQUENCE: 163

Glu Leu Pro Gln Lys Ala Glu Ala Leu Lys Leu Phe Leu Glu Glu Thr
1               5                   10                  15

Lys Ala Thr Val
            20

<210> SEQ ID NO 164
<211> LENGTH: 20
<212> TYPE: PRT
<213> ORGANISM: Artificial Sequence
<220> FEATURE:
<223> OTHER INFORMATION: Synthetic peptide

<400> SEQUENCE: 164

Thr Lys Ala Thr Val Ala Val Tyr Leu Glu Ser Leu Gln Asp Thr Lys
1               5                   10                  15

Ile Thr Leu Ile
            20

<210> SEQ ID NO 165
<211> LENGTH: 20
<212> TYPE: PRT
<213> ORGANISM: Artificial Sequence
<220> FEATURE:
<223> OTHER INFORMATION: Synthetic peptide

<400> SEQUENCE: 165

Lys Ile Thr Leu Ile Ile Asn Trp Leu Gln Glu Ala Leu Ser Ser Ala
1               5                   10                  15

Ser Leu Ala His
            20

<210> SEQ ID NO 166
<211> LENGTH: 20
<212> TYPE: PRT
<213> ORGANISM: Artificial Sequence
<220> FEATURE:
<223> OTHER INFORMATION: Synthetic peptide

<400> SEQUENCE: 166

Ala Ser Leu Ala His Met Lys Ala Lys Phe Arg Glu Thr Leu Glu Asp
1               5                   10                  15

Thr Arg Asp Arg
            20

<210> SEQ ID NO 167
<211> LENGTH: 20
<212> TYPE: PRT
<213> ORGANISM: Artificial Sequence
<220> FEATURE:
<223> OTHER INFORMATION: Synthetic peptide

<400> SEQUENCE: 167

Asp Thr Arg Asp Arg Met Tyr Gln Met Asp Ile Gln Gln Glu Leu Gln
1               5                   10                  15

Arg Tyr Leu Ser
            20

<210> SEQ ID NO 168
<211> LENGTH: 20
<212> TYPE: PRT
<213> ORGANISM: Artificial Sequence
<220> FEATURE:
<223> OTHER INFORMATION: Synthetic peptide

<400> SEQUENCE: 168

Gln Arg Tyr Leu Ser Leu Val Gly Gln Val Tyr Ser Thr Leu Val Thr
1               5                   10                  15

Tyr Ile Ser Asp
            20

<210> SEQ ID NO 169
<211> LENGTH: 20
<212> TYPE: PRT
<213> ORGANISM: Artificial Sequence
<220> FEATURE:
<223> OTHER INFORMATION: Synthetic peptide

<400> SEQUENCE: 169

Thr Tyr Ile Ser Asp Trp Trp Thr Leu Ala Ala Lys Asn Leu Thr Asp
1               5                   10                  15

Phe Ala Glu Gln
            20

<210> SEQ ID NO 170
<211> LENGTH: 20
<212> TYPE: PRT
<213> ORGANISM: Artificial Sequence
<220> FEATURE:
<223> OTHER INFORMATION: Synthetic peptide

<400> SEQUENCE: 170

Asp Phe Ala Glu Gln Tyr Ser Ile Gln Asp Trp Ala Lys Arg Met Lys
1               5                   10                  15

Ala Leu Val Glu
            20

<210> SEQ ID NO 171
<211> LENGTH: 20
<212> TYPE: PRT
<213> ORGANISM: Artificial Sequence
<220> FEATURE:
<223> OTHER INFORMATION: Synthetic peptide

<400> SEQUENCE: 171

Lys Ala Leu Val Glu Gln Gly Phe Thr Val Pro Glu Ile Lys Thr Ile
1               5                   10                  15

Leu Gly Thr Met
            20

<210> SEQ ID NO 172
<211> LENGTH: 20
<212> TYPE: PRT
<213> ORGANISM: Artificial Sequence
<220> FEATURE:
<223> OTHER INFORMATION: Synthetic peptide

<400> SEQUENCE: 172

Ile Leu Gly Thr Met Pro Ala Phe Glu Val Ser Leu Gln Ala Leu Gln
1               5                   10                  15

Lys Ala Thr Phe
            20

<210> SEQ ID NO 173
<211> LENGTH: 20
<212> TYPE: PRT
<213> ORGANISM: Artificial Sequence
<220> FEATURE:

<223> OTHER INFORMATION: Synthetic peptide

<400> SEQUENCE: 173

Gln Lys Ala Thr Phe Gln Thr Pro Asp Phe Ile Val Pro Leu Thr Asp
1               5                   10                  15

Leu Arg Ile Pro
            20

<210> SEQ ID NO 174
<211> LENGTH: 20
<212> TYPE: PRT
<213> ORGANISM: Artificial Sequence
<220> FEATURE:
<223> OTHER INFORMATION: Synthetic peptide

<400> SEQUENCE: 174

Asp Leu Arg Ile Pro Ser Val Gln Ile Asn Phe Lys Asp Leu Lys Asn
1               5                   10                  15

Ile Lys Ile Pro
            20

<210> SEQ ID NO 175
<211> LENGTH: 20
<212> TYPE: PRT
<213> ORGANISM: Artificial Sequence
<220> FEATURE:
<223> OTHER INFORMATION: Synthetic peptide

<400> SEQUENCE: 175

Asn Ile Lys Ile Pro Ser Arg Phe Ser Thr Pro Glu Phe Thr Ile Leu
1               5                   10                  15

Asn Thr Phe His
            20

<210> SEQ ID NO 176
<211> LENGTH: 20
<212> TYPE: PRT
<213> ORGANISM: Artificial Sequence
<220> FEATURE:
<223> OTHER INFORMATION: Synthetic peptide

<400> SEQUENCE: 176

Leu Asn Thr Phe His Ile Pro Ser Phe Thr Ile Asp Phe Val Glu Met
1               5                   10                  15

Lys Val Lys Ile
            20

<210> SEQ ID NO 177
<211> LENGTH: 20
<212> TYPE: PRT
<213> ORGANISM: Artificial Sequence
<220> FEATURE:
<223> OTHER INFORMATION: Synthetic peptide

<400> SEQUENCE: 177

Met Lys Val Lys Ile Ile Arg Thr Ile Asp Gln Met Gln Asn Ser Glu
1               5                   10                  15

Leu Gln Trp Pro
            20

<210> SEQ ID NO 178
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 178

Glu Leu Gln Trp Pro Val Pro Asp Ile Tyr Leu Arg Asp Leu Lys Val
1               5                   10                  15

Glu Asp Ile Pro
            20

<210> SEQ ID NO 179
<211> LENGTH: 20
<212> TYPE: PRT
<213> ORGANISM: Artificial Sequence
<220> FEATURE:
<223> OTHER INFORMATION: Synthetic peptide

<400> SEQUENCE: 179

Val Glu Asp Ile Pro Leu Ala Arg Ile Thr Leu Pro Asp Phe Arg Leu
1               5                   10                  15

Pro Glu Ile Ala
            20

<210> SEQ ID NO 180
<211> LENGTH: 20
<212> TYPE: PRT
<213> ORGANISM: Artificial Sequence
<220> FEATURE:
<223> OTHER INFORMATION: Synthetic peptide

<400> SEQUENCE: 180

Leu Pro Glu Ile Ala Ile Pro Glu Phe Ile Ile Pro Thr Leu Asn Leu
1               5                   10                  15

Asn Asp Phe Gln
            20

<210> SEQ ID NO 181
<211> LENGTH: 20
<212> TYPE: PRT
<213> ORGANISM: Artificial Sequence
<220> FEATURE:
<223> OTHER INFORMATION: Synthetic peptide

<400> SEQUENCE: 181

Leu Asn Asp Phe Gln Val Pro Asp Leu His Ile Pro Glu Phe Gln Leu
1               5                   10                  15

Pro His Ile Ser
            20

<210> SEQ ID NO 182
<211> LENGTH: 20
<212> TYPE: PRT
<213> ORGANISM: Artificial Sequence
<220> FEATURE:
<223> OTHER INFORMATION: Synthetic peptide

<400> SEQUENCE: 182

Leu Pro His Ile Ser His Thr Ile Glu Val Pro Thr Phe Gly Lys Leu
1               5                   10                  15

Tyr Ser Ile Leu
            20

<210> SEQ ID NO 183
<211> LENGTH: 20
<212> TYPE: PRT
```

<210> SEQ ID NO 183
<211> LENGTH: 20
<212> TYPE: PRT
<213> ORGANISM: Artificial Sequence
<220> FEATURE:
<223> OTHER INFORMATION: Synthetic peptide

<400> SEQUENCE: 183

Leu Tyr Ser Ile Leu Lys Ile Gln Ser Pro Leu Phe Thr Leu Asp Ala
1               5                   10                  15

Asn Ala Asp Ile
            20

<210> SEQ ID NO 184
<211> LENGTH: 20
<212> TYPE: PRT
<213> ORGANISM: Artificial Sequence
<220> FEATURE:
<223> OTHER INFORMATION: Synthetic peptide

<400> SEQUENCE: 184

Ala Asn Ala Asp Ile Gly Asn Gly Thr Thr Ser Ala Asn Glu Ala Gly
1               5                   10                  15

Ile Ala Ala Ser
            20

<210> SEQ ID NO 185
<211> LENGTH: 20
<212> TYPE: PRT
<213> ORGANISM: Artificial Sequence
<220> FEATURE:
<223> OTHER INFORMATION: Synthetic peptide

<400> SEQUENCE: 185

Gly Ile Ala Ala Ser Ile Thr Ala Lys Gly Glu Ser Lys Leu Glu Val
1               5                   10                  15

Leu Asn Phe Asp
            20

<210> SEQ ID NO 186
<211> LENGTH: 20
<212> TYPE: PRT
<213> ORGANISM: Artificial Sequence
<220> FEATURE:
<223> OTHER INFORMATION: Synthetic peptide

<400> SEQUENCE: 186

Val Leu Asn Phe Asp Phe Gln Ala Asn Ala Gln Leu Ser Asn Pro Lys
1               5                   10                  15

Ile Asn Pro Leu
            20

<210> SEQ ID NO 187
<211> LENGTH: 20
<212> TYPE: PRT
<213> ORGANISM: Artificial Sequence
<220> FEATURE:
<223> OTHER INFORMATION: Synthetic peptide

<400> SEQUENCE: 187

Lys Ile Asn Pro Leu Ala Leu Lys Glu Ser Val Lys Phe Ser Ser Lys
1               5                   10                  15

Tyr Leu Arg Thr
            20

<210> SEQ ID NO 188
<211> LENGTH: 20

```
<212> TYPE: PRT
<213> ORGANISM: Artificial Sequence
<220> FEATURE:
<223> OTHER INFORMATION: Synthetic peptide

<400> SEQUENCE: 188

Lys Tyr Leu Arg Thr Glu His Gly Ser Glu Met Leu Phe Phe Gly Asn
1               5                   10                  15

Ala Ile Glu Gly
            20

<210> SEQ ID NO 189
<211> LENGTH: 20
<212> TYPE: PRT
<213> ORGANISM: Artificial Sequence
<220> FEATURE:
<223> OTHER INFORMATION: Synthetic peptide

<400> SEQUENCE: 189

Asn Ala Ile Glu Gly Lys Ser Asn Thr Val Ala Ser Leu His Thr Glu
1               5                   10                  15

Lys Asn Thr Leu
            20

<210> SEQ ID NO 190
<211> LENGTH: 20
<212> TYPE: PRT
<213> ORGANISM: Artificial Sequence
<220> FEATURE:
<223> OTHER INFORMATION: Synthetic peptide

<400> SEQUENCE: 190

Glu Lys Asn Thr Leu Glu Leu Ser Asn Gly Val Ile Val Lys Ile Asn
1               5                   10                  15

Asn Gln Leu Thr
            20

<210> SEQ ID NO 191
<211> LENGTH: 20
<212> TYPE: PRT
<213> ORGANISM: Artificial Sequence
<220> FEATURE:
<223> OTHER INFORMATION: Synthetic peptide

<400> SEQUENCE: 191

Asn Asn Gln Leu Thr Leu Asp Ser Asn Thr Lys Tyr Phe His Lys Leu
1               5                   10                  15

Asn Ile Pro Lys
            20

<210> SEQ ID NO 192
<211> LENGTH: 20
<212> TYPE: PRT
<213> ORGANISM: Artificial Sequence
<220> FEATURE:
<223> OTHER INFORMATION: Synthetic peptide

<400> SEQUENCE: 192

Leu Asn Ile Pro Lys Leu Asp Phe Ser Ser Gln Ala Asp Leu Arg Asn
1               5                   10                  15

Glu Ile Lys Thr
            20

<210> SEQ ID NO 193
```

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 193

Asn Glu Ile Lys Thr Leu Leu Lys Ala Gly His Ile Ala Trp Thr Ser
1               5                   10                  15

Ser Gly Lys Gly
            20

<210> SEQ ID NO 194
<211> LENGTH: 20
<212> TYPE: PRT
<213> ORGANISM: Artificial Sequence
<220> FEATURE:
<223> OTHER INFORMATION: Synthetic peptide

<400> SEQUENCE: 194

Ser Ser Gly Lys Gly Ser Trp Lys Trp Ala Cys Pro Arg Phe Ser Asp
1               5                   10                  15

Glu Gly Thr His
            20

<210> SEQ ID NO 195
<211> LENGTH: 20
<212> TYPE: PRT
<213> ORGANISM: Artificial Sequence
<220> FEATURE:
<223> OTHER INFORMATION: Synthetic peptide

<400> SEQUENCE: 195

Asp Glu Gly Thr His Glu Ser Gln Ile Ser Phe Thr Ile Glu Gly Pro
1               5                   10                  15

Leu Thr Ser Phe
            20

<210> SEQ ID NO 196
<211> LENGTH: 20
<212> TYPE: PRT
<213> ORGANISM: Artificial Sequence
<220> FEATURE:
<223> OTHER INFORMATION: Synthetic peptide

<400> SEQUENCE: 196

Pro Leu Thr Ser Phe Gly Leu Ser Asn Lys Ile Asn Ser Lys His Leu
1               5                   10                  15

Arg Val Asn Gln
            20

<210> SEQ ID NO 197
<211> LENGTH: 20
<212> TYPE: PRT
<213> ORGANISM: Artificial Sequence
<220> FEATURE:
<223> OTHER INFORMATION: Synthetic peptide

<400> SEQUENCE: 197

Leu Arg Val Asn Gln Asn Leu Val Tyr Glu Ser Gly Ser Leu Asn Phe
1               5                   10                  15

Ser Lys Leu Glu
            20
```

```
<210> SEQ ID NO 198
<211> LENGTH: 20
<212> TYPE: PRT
<213> ORGANISM: Artificial Sequence
<220> FEATURE:
<223> OTHER INFORMATION: Synthetic peptide

<400> SEQUENCE: 198

Phe Ser Lys Leu Glu Ile Gln Ser Gln Val Asp Ser Gln His Val Gly
1               5                   10                  15

His Ser Val Leu
            20

<210> SEQ ID NO 199
<211> LENGTH: 20
<212> TYPE: PRT
<213> ORGANISM: Artificial Sequence
<220> FEATURE:
<223> OTHER INFORMATION: Synthetic peptide

<400> SEQUENCE: 199

Gly His Ser Val Leu Thr Ala Lys Gly Met Ala Leu Phe Gly Glu Gly
1               5                   10                  15

Lys Ala Glu Phe
            20

<210> SEQ ID NO 200
<211> LENGTH: 20
<212> TYPE: PRT
<213> ORGANISM: Artificial Sequence
<220> FEATURE:
<223> OTHER INFORMATION: Synthetic peptide

<400> SEQUENCE: 200

Gly Lys Ala Glu Phe Thr Gly Arg His Asp Ala His Leu Asn Gly Lys
1               5                   10                  15

Val Ile Gly Thr
            20

<210> SEQ ID NO 201
<211> LENGTH: 20
<212> TYPE: PRT
<213> ORGANISM: Artificial Sequence
<220> FEATURE:
<223> OTHER INFORMATION: Synthetic peptide

<400> SEQUENCE: 201

Lys Val Ile Gly Thr Leu Lys Asn Ser Leu Phe Phe Ser Ala Gln Pro
1               5                   10                  15

Phe Glu Ile Thr
            20

<210> SEQ ID NO 202
<211> LENGTH: 20
<212> TYPE: PRT
<213> ORGANISM: Artificial Sequence
<220> FEATURE:
<223> OTHER INFORMATION: Synthetic peptide

<400> SEQUENCE: 202

Pro Phe Glu Ile Thr Ala Ser Thr Asn Asn Glu Gly Asn Leu Lys Val
1               5                   10                  15

Arg Phe Pro Leu
            20
```

```
<210> SEQ ID NO 203
<211> LENGTH: 20
<212> TYPE: PRT
<213> ORGANISM: Artificial Sequence
<220> FEATURE:
<223> OTHER INFORMATION: Synthetic peptide

<400> SEQUENCE: 203

Val Arg Phe Pro Leu Arg Leu Thr Gly Lys Ile Asp Phe Leu Asn Asn
1               5                   10                  15

Tyr Ala Leu Phe
            20

<210> SEQ ID NO 204
<211> LENGTH: 20
<212> TYPE: PRT
<213> ORGANISM: Artificial Sequence
<220> FEATURE:
<223> OTHER INFORMATION: Synthetic peptide

<400> SEQUENCE: 204

Asn Tyr Ala Leu Phe Leu Ser Pro Ser Ala Gln Gln Ala Ser Trp Gln
1               5                   10                  15

Val Ser Ala Arg
            20

<210> SEQ ID NO 205
<211> LENGTH: 20
<212> TYPE: PRT
<213> ORGANISM: Artificial Sequence
<220> FEATURE:
<223> OTHER INFORMATION: Synthetic peptide

<400> SEQUENCE: 205

Gln Val Ser Ala Arg Phe Asn Gln Tyr Lys Tyr Asn Gln Asn Phe Ser
1               5                   10                  15

Ala Gly Asn Asn
            20

<210> SEQ ID NO 206
<211> LENGTH: 20
<212> TYPE: PRT
<213> ORGANISM: Artificial Sequence
<220> FEATURE:
<223> OTHER INFORMATION: Synthetic peptide

<400> SEQUENCE: 206

Ser Ala Gly Asn Asn Glu Asn Ile Met Glu Ala His Val Gly Ile Asn
1               5                   10                  15

Gly Glu Ala Asn
            20

<210> SEQ ID NO 207
<211> LENGTH: 20
<212> TYPE: PRT
<213> ORGANISM: Artificial Sequence
<220> FEATURE:
<223> OTHER INFORMATION: Synthetic peptide

<400> SEQUENCE: 207

Asn Gly Glu Ala Asn Leu Asp Phe Leu Asn Ile Pro Leu Thr Ile Pro
1               5                   10                  15

Glu Met Arg Leu
            20
```

```
<210> SEQ ID NO 208
<211> LENGTH: 20
<212> TYPE: PRT
<213> ORGANISM: Artificial Sequence
<220> FEATURE:
<223> OTHER INFORMATION: Synthetic peptide

<400> SEQUENCE: 208

Pro Glu Met Arg Leu Pro Tyr Thr Ile Ile Thr Thr Pro Pro Leu Lys
1               5                   10                  15

Asp Phe Ser Leu
            20

<210> SEQ ID NO 209
<211> LENGTH: 20
<212> TYPE: PRT
<213> ORGANISM: Artificial Sequence
<220> FEATURE:
<223> OTHER INFORMATION: Synthetic peptide

<400> SEQUENCE: 209

Lys Asp Phe Ser Leu Trp Glu Lys Thr Gly Leu Lys Glu Phe Leu Lys
1               5                   10                  15

Thr Thr Lys Gln
            20

<210> SEQ ID NO 210
<211> LENGTH: 20
<212> TYPE: PRT
<213> ORGANISM: Artificial Sequence
<220> FEATURE:
<223> OTHER INFORMATION: Synthetic peptide

<400> SEQUENCE: 210

Lys Thr Thr Lys Gln Ser Phe Asp Leu Ser Val Lys Ala Gln Tyr Lys
1               5                   10                  15

Lys Asn Lys His
            20

<210> SEQ ID NO 211
<211> LENGTH: 20
<212> TYPE: PRT
<213> ORGANISM: Artificial Sequence
<220> FEATURE:
<223> OTHER INFORMATION: Synthetic peptide

<400> SEQUENCE: 211

Lys Lys Asn Lys His Arg His Ser Ile Thr Asn Pro Leu Ala Val Leu
1               5                   10                  15

Cys Glu Phe Ile
            20

<210> SEQ ID NO 212
<211> LENGTH: 20
<212> TYPE: PRT
<213> ORGANISM: Artificial Sequence
<220> FEATURE:
<223> OTHER INFORMATION: Synthetic peptide

<400> SEQUENCE: 212

Leu Cys Glu Phe Ile Ser Gln Ser Ile Lys Ser Phe Asp Arg His Phe
1               5                   10                  15

Glu Lys Asn Arg
```

```
<210> SEQ ID NO 213
<211> LENGTH: 20
<212> TYPE: PRT
<213> ORGANISM: Artificial Sequence
<220> FEATURE:
<223> OTHER INFORMATION: Synthetic peptide

<400> SEQUENCE: 213

Phe Glu Lys Asn Arg Asn Asn Ala Leu Asp Phe Val Thr Lys Ser Tyr
1               5                   10                  15

Asn Glu Thr Lys
            20

<210> SEQ ID NO 214
<211> LENGTH: 20
<212> TYPE: PRT
<213> ORGANISM: Artificial Sequence
<220> FEATURE:
<223> OTHER INFORMATION: Synthetic peptide

<400> SEQUENCE: 214

Tyr Asn Glu Thr Lys Ile Lys Phe Asp Lys Tyr Lys Ala Glu Lys Ser
1               5                   10                  15

His Asp Glu Leu
            20

<210> SEQ ID NO 215
<211> LENGTH: 20
<212> TYPE: PRT
<213> ORGANISM: Artificial Sequence
<220> FEATURE:
<223> OTHER INFORMATION: Synthetic peptide

<400> SEQUENCE: 215

Ser His Asp Glu Leu Pro Arg Thr Phe Gln Ile Pro Gly Tyr Thr Val
1               5                   10                  15

Pro Val Val Asn
            20

<210> SEQ ID NO 216
<211> LENGTH: 20
<212> TYPE: PRT
<213> ORGANISM: Artificial Sequence
<220> FEATURE:
<223> OTHER INFORMATION: Synthetic peptide

<400> SEQUENCE: 216

Val Pro Val Val Asn Val Glu Val Ser Pro Phe Thr Ile Glu Met Ser
1               5                   10                  15

Ala Phe Gly Tyr
            20

<210> SEQ ID NO 217
<211> LENGTH: 20
<212> TYPE: PRT
<213> ORGANISM: Artificial Sequence
<220> FEATURE:
<223> OTHER INFORMATION: Synthetic peptide

<400> SEQUENCE: 217

Ser Ala Phe Gly Tyr Val Phe Pro Lys Ala Val Ser Met Pro Ser Phe
1               5                   10                  15
```

Ser Ile Leu Gly
            20

<210> SEQ ID NO 218
<211> LENGTH: 20
<212> TYPE: PRT
<213> ORGANISM: Artificial Sequence
<220> FEATURE:
<223> OTHER INFORMATION: Synthetic peptide

<400> SEQUENCE: 218

Phe Ser Ile Leu Gly Ser Asp Val Arg Val Pro Ser Tyr Thr Leu Ile
1               5                   10                  15

Leu Pro Ser Leu
            20

<210> SEQ ID NO 219
<211> LENGTH: 20
<212> TYPE: PRT
<213> ORGANISM: Artificial Sequence
<220> FEATURE:
<223> OTHER INFORMATION: Synthetic peptide

<400> SEQUENCE: 219

Ile Leu Pro Ser Leu Glu Leu Pro Val Leu His Val Pro Arg Asn Leu
1               5                   10                  15

Lys Leu Ser Leu
            20

<210> SEQ ID NO 220
<211> LENGTH: 20
<212> TYPE: PRT
<213> ORGANISM: Artificial Sequence
<220> FEATURE:
<223> OTHER INFORMATION: Synthetic peptide

<400> SEQUENCE: 220

Leu Lys Leu Ser Leu Pro His Phe Lys Glu Leu Cys Thr Ile Ser His
1               5                   10                  15

Ile Phe Ile Pro
            20

<210> SEQ ID NO 221
<211> LENGTH: 20
<212> TYPE: PRT
<213> ORGANISM: Artificial Sequence
<220> FEATURE:
<223> OTHER INFORMATION: Synthetic peptide

<400> SEQUENCE: 221

His Ile Phe Ile Pro Ala Met Gly Asn Ile Thr Tyr Asp Phe Ser Phe
1               5                   10                  15

Lys Ser Ser Val
            20

<210> SEQ ID NO 222
<211> LENGTH: 20
<212> TYPE: PRT
<213> ORGANISM: Artificial Sequence
<220> FEATURE:
<223> OTHER INFORMATION: Synthetic peptide

<400> SEQUENCE: 222

Phe Lys Ser Ser Val Ile Thr Leu Asn Thr Asn Ala Glu Leu Phe Asn
1               5                   10                  15

```
Gln Ser Asp Ile
            20

<210> SEQ ID NO 223
<211> LENGTH: 20
<212> TYPE: PRT
<213> ORGANISM: Artificial Sequence
<220> FEATURE:
<223> OTHER INFORMATION: Synthetic peptide

<400> SEQUENCE: 223

Asn Gln Ser Asp Ile Val Ala His Leu Leu Ser Ser Ser Ser Ser Val
1               5                   10                  15

Ile Asp Ala Leu
            20

<210> SEQ ID NO 224
<211> LENGTH: 20
<212> TYPE: PRT
<213> ORGANISM: Artificial Sequence
<220> FEATURE:
<223> OTHER INFORMATION: Synthetic peptide

<400> SEQUENCE: 224

Val Ile Asp Ala Leu Gln Tyr Lys Leu Glu Gly Thr Thr Arg Leu Thr
1               5                   10                  15

Arg Lys Arg Gly
            20

<210> SEQ ID NO 225
<211> LENGTH: 20
<212> TYPE: PRT
<213> ORGANISM: Artificial Sequence
<220> FEATURE:
<223> OTHER INFORMATION: Synthetic peptide

<400> SEQUENCE: 225

Thr Arg Lys Arg Gly Leu Lys Leu Ala Thr Ala Leu Ser Leu Ser Asn
1               5                   10                  15

Lys Phe Val Glu
            20

<210> SEQ ID NO 226
<211> LENGTH: 20
<212> TYPE: PRT
<213> ORGANISM: Artificial Sequence
<220> FEATURE:
<223> OTHER INFORMATION: Synthetic peptide

<400> SEQUENCE: 226

Asn Lys Phe Val Glu Gly Ser His Asn Ser Thr Val Ser Leu Thr Thr
1               5                   10                  15

Lys Asn Met Glu
            20

<210> SEQ ID NO 227
<211> LENGTH: 20
<212> TYPE: PRT
<213> ORGANISM: Artificial Sequence
<220> FEATURE:
<223> OTHER INFORMATION: Synthetic peptide

<400> SEQUENCE: 227

Thr Lys Asn Met Glu Val Ser Val Ala Lys Thr Thr Lys Ala Glu Ile
```

```
                1               5                  10                 15
Pro Ile Leu Arg
            20

<210> SEQ ID NO 228
<211> LENGTH: 20
<212> TYPE: PRT
<213> ORGANISM: Artificial Sequence
<220> FEATURE:
<223> OTHER INFORMATION: Synthetic peptide

<400> SEQUENCE: 228

Ile Pro Ile Leu Arg Met Asn Phe Lys Gln Glu Leu Asn Gly Asn Thr
1               5                  10                  15
Lys Ser Lys Pro
            20

<210> SEQ ID NO 229
<211> LENGTH: 20
<212> TYPE: PRT
<213> ORGANISM: Artificial Sequence
<220> FEATURE:
<223> OTHER INFORMATION: Synthetic peptide

<400> SEQUENCE: 229

Thr Lys Ser Lys Pro Thr Val Ser Ser Ser Met Glu Phe Lys Tyr Asp
1               5                  10                  15
Phe Asn Ser Ser
            20

<210> SEQ ID NO 230
<211> LENGTH: 20
<212> TYPE: PRT
<213> ORGANISM: Artificial Sequence
<220> FEATURE:
<223> OTHER INFORMATION: Synthetic peptide

<400> SEQUENCE: 230

Asp Phe Asn Ser Ser Met Leu Tyr Ser Thr Ala Lys Gly Ala Val Asp
1               5                  10                  15
His Lys Leu Ser
            20

<210> SEQ ID NO 231
<211> LENGTH: 20
<212> TYPE: PRT
<213> ORGANISM: Artificial Sequence
<220> FEATURE:
<223> OTHER INFORMATION: Synthetic peptide

<400> SEQUENCE: 231

Asp His Lys Leu Ser Leu Glu Ser Leu Thr Ser Tyr Phe Ser Ile Glu
1               5                  10                  15
Ser Ser Thr Lys
            20

<210> SEQ ID NO 232
<211> LENGTH: 20
<212> TYPE: PRT
<213> ORGANISM: Artificial Sequence
<220> FEATURE:
<223> OTHER INFORMATION: Synthetic peptide

<400> SEQUENCE: 232
```

Glu Ser Ser Thr Lys Gly Asp Val Lys Gly Ser Val Leu Ser Arg Glu
1               5                   10                  15

Tyr Ser Gly Thr
            20

<210> SEQ ID NO 233
<211> LENGTH: 20
<212> TYPE: PRT
<213> ORGANISM: Artificial Sequence
<220> FEATURE:
<223> OTHER INFORMATION: Synthetic peptide

<400> SEQUENCE: 233

Glu Tyr Ser Gly Thr Ile Ala Ser Glu Ala Asn Thr Tyr Leu Asn Ser
1               5                   10                  15

Lys Ser Thr Arg
            20

<210> SEQ ID NO 234
<211> LENGTH: 20
<212> TYPE: PRT
<213> ORGANISM: Artificial Sequence
<220> FEATURE:
<223> OTHER INFORMATION: Synthetic peptide

<400> SEQUENCE: 234

Ser Lys Ser Thr Arg Ser Ser Val Lys Leu Gln Gly Thr Ser Lys Ile
1               5                   10                  15

Asp Asp Ile Trp
            20

<210> SEQ ID NO 235
<211> LENGTH: 20
<212> TYPE: PRT
<213> ORGANISM: Artificial Sequence
<220> FEATURE:
<223> OTHER INFORMATION: Synthetic peptide

<400> SEQUENCE: 235

Ile Asp Asp Ile Trp Asn Leu Glu Val Lys Glu Asn Phe Ala Gly Glu
1               5                   10                  15

Ala Thr Leu Gln
            20

<210> SEQ ID NO 236
<211> LENGTH: 20
<212> TYPE: PRT
<213> ORGANISM: Artificial Sequence
<220> FEATURE:
<223> OTHER INFORMATION: Synthetic peptide

<400> SEQUENCE: 236

Glu Ala Thr Leu Gln Arg Ile Tyr Ser Leu Trp Glu His Ser Thr Lys
1               5                   10                  15

Asn His Leu Gln
            20

<210> SEQ ID NO 237
<211> LENGTH: 20
<212> TYPE: PRT
<213> ORGANISM: Artificial Sequence
<220> FEATURE:
<223> OTHER INFORMATION: Synthetic peptide

<400> SEQUENCE: 237

```
Lys Asn His Leu Gln Leu Glu Gly Leu Phe Phe Thr Asn Gly Glu His
1               5                   10                  15

Thr Ser Lys Ala
            20

<210> SEQ ID NO 238
<211> LENGTH: 20
<212> TYPE: PRT
<213> ORGANISM: Artificial Sequence
<220> FEATURE:
<223> OTHER INFORMATION: Synthetic peptide

<400> SEQUENCE: 238

His Thr Ser Lys Ala Thr Leu Glu Leu Ser Pro Trp Gln Met Ser Ala
1               5                   10                  15

Leu Val Gln Val
            20

<210> SEQ ID NO 239
<211> LENGTH: 20
<212> TYPE: PRT
<213> ORGANISM: Artificial Sequence
<220> FEATURE:
<223> OTHER INFORMATION: Synthetic peptide

<400> SEQUENCE: 239

Ala Leu Val Gln Val His Ala Ser Gln Pro Ser Ser Phe His Asp Phe
1               5                   10                  15

Pro Asp Leu Gly
            20

<210> SEQ ID NO 240
<211> LENGTH: 20
<212> TYPE: PRT
<213> ORGANISM: Artificial Sequence
<220> FEATURE:
<223> OTHER INFORMATION: Synthetic peptide

<400> SEQUENCE: 240

Phe Pro Asp Leu Gly Gln Glu Val Ala Leu Asn Ala Asn Thr Lys Asn
1               5                   10                  15

Gln Lys Ile Arg
            20

<210> SEQ ID NO 241
<211> LENGTH: 20
<212> TYPE: PRT
<213> ORGANISM: Artificial Sequence
<220> FEATURE:
<223> OTHER INFORMATION: Synthetic peptide

<400> SEQUENCE: 241

Asn Gln Lys Ile Arg Trp Lys Asn Glu Val Arg Ile His Ser Gly Ser
1               5                   10                  15

Phe Gln Ser Gln
            20

<210> SEQ ID NO 242
<211> LENGTH: 20
<212> TYPE: PRT
<213> ORGANISM: Artificial Sequence
<220> FEATURE:
<223> OTHER INFORMATION: Synthetic peptide
```

```
<400> SEQUENCE: 242

Ser Phe Gln Ser Gln Val Glu Leu Ser Asn Asp Gln Glu Lys Ala His
1               5                   10                  15

Leu Asp Ile Ala
            20

<210> SEQ ID NO 243
<211> LENGTH: 20
<212> TYPE: PRT
<213> ORGANISM: Artificial Sequence
<220> FEATURE:
<223> OTHER INFORMATION: Synthetic peptide

<400> SEQUENCE: 243

His Leu Asp Ile Ala Gly Ser Leu Glu Gly His Leu Arg Phe Leu Lys
1               5                   10                  15

Asn Ile Ile Leu
            20

<210> SEQ ID NO 244
<211> LENGTH: 20
<212> TYPE: PRT
<213> ORGANISM: Artificial Sequence
<220> FEATURE:
<223> OTHER INFORMATION: Synthetic peptide

<400> SEQUENCE: 244

Lys Asn Ile Ile Leu Pro Val Tyr Asp Lys Ser Leu Trp Asp Phe Leu
1               5                   10                  15

Lys Leu Asp Val
            20

<210> SEQ ID NO 245
<211> LENGTH: 20
<212> TYPE: PRT
<213> ORGANISM: Artificial Sequence
<220> FEATURE:
<223> OTHER INFORMATION: Synthetic peptide

<400> SEQUENCE: 245

Leu Lys Leu Asp Val Thr Thr Ser Ile Gly Arg Arg Gln His Leu Arg
1               5                   10                  15

Val Ser Thr Ala
            20

<210> SEQ ID NO 246
<211> LENGTH: 20
<212> TYPE: PRT
<213> ORGANISM: Artificial Sequence
<220> FEATURE:
<223> OTHER INFORMATION: Synthetic peptide

<400> SEQUENCE: 246

Arg Val Ser Thr Ala Phe Val Tyr Thr Lys Asn Pro Asn Gly Tyr Ser
1               5                   10                  15

Phe Ser Ile Pro
            20

<210> SEQ ID NO 247
<211> LENGTH: 20
<212> TYPE: PRT
<213> ORGANISM: Artificial Sequence
<220> FEATURE:
<223> OTHER INFORMATION: Synthetic peptide
```

<400> SEQUENCE: 247

Ser Phe Ser Ile Pro Val Lys Val Leu Ala Asp Lys Phe Ile Thr Pro
1               5                   10                  15

Gly Leu Lys Leu
            20

<210> SEQ ID NO 248
<211> LENGTH: 20
<212> TYPE: PRT
<213> ORGANISM: Artificial Sequence
<220> FEATURE:
<223> OTHER INFORMATION: Synthetic peptide

<400> SEQUENCE: 248

Pro Gly Leu Lys Leu Asn Asp Leu Asn Ser Val Leu Val Met Pro Thr
1               5                   10                  15

Phe His Val Pro
            20

<210> SEQ ID NO 249
<211> LENGTH: 20
<212> TYPE: PRT
<213> ORGANISM: Artificial Sequence
<220> FEATURE:
<223> OTHER INFORMATION: Synthetic peptide

<400> SEQUENCE: 249

Thr Phe His Val Pro Phe Thr Asp Leu Gln Val Pro Ser Cys Lys Leu
1               5                   10                  15

Asp Phe Arg Glu
            20

<210> SEQ ID NO 250
<211> LENGTH: 20
<212> TYPE: PRT
<213> ORGANISM: Artificial Sequence
<220> FEATURE:
<223> OTHER INFORMATION: Synthetic peptide

<400> SEQUENCE: 250

Leu Asp Phe Arg Glu Ile Gln Ile Tyr Lys Lys Leu Arg Thr Ser Ser
1               5                   10                  15

Phe Ala Leu Asn
            20

<210> SEQ ID NO 251
<211> LENGTH: 20
<212> TYPE: PRT
<213> ORGANISM: Artificial Sequence
<220> FEATURE:
<223> OTHER INFORMATION: Synthetic peptide

<400> SEQUENCE: 251

Ser Phe Ala Leu Asn Leu Pro Thr Leu Pro Glu Val Lys Phe Pro Glu
1               5                   10                  15

Val Asp Val Leu
            20

<210> SEQ ID NO 252
<211> LENGTH: 20
<212> TYPE: PRT
<213> ORGANISM: Artificial Sequence
<220> FEATURE:

<223> OTHER INFORMATION: Synthetic peptide

<400> SEQUENCE: 252

Glu Val Asp Val Leu Thr Lys Tyr Ser Gln Pro Glu Asp Ser Leu Ile
1               5                   10                  15

Pro Phe Phe Glu
            20

<210> SEQ ID NO 253
<211> LENGTH: 20
<212> TYPE: PRT
<213> ORGANISM: Artificial Sequence
<220> FEATURE:
<223> OTHER INFORMATION: Synthetic peptide

<400> SEQUENCE: 253

Ile Pro Phe Phe Glu Ile Thr Val Pro Glu Ser Gln Leu Thr Val Ser
1               5                   10                  15

Gln Phe Thr Leu
            20

<210> SEQ ID NO 254
<211> LENGTH: 20
<212> TYPE: PRT
<213> ORGANISM: Artificial Sequence
<220> FEATURE:
<223> OTHER INFORMATION: Synthetic peptide

<400> SEQUENCE: 254

Ser Gln Phe Thr Leu Pro Lys Ser Val Ser Asp Gly Ile Ala Ala Leu
1               5                   10                  15

Asp Leu Asn Ala
            20

<210> SEQ ID NO 255
<211> LENGTH: 20
<212> TYPE: PRT
<213> ORGANISM: Artificial Sequence
<220> FEATURE:
<223> OTHER INFORMATION: Synthetic peptide

<400> SEQUENCE: 255

Leu Asp Leu Asn Ala Val Ala Asn Lys Ile Ala Asp Phe Glu Leu Pro
1               5                   10                  15

Thr Ile Ile Val
            20

<210> SEQ ID NO 256
<211> LENGTH: 20
<212> TYPE: PRT
<213> ORGANISM: Artificial Sequence
<220> FEATURE:
<223> OTHER INFORMATION: Synthetic peptide

<400> SEQUENCE: 256

Pro Thr Ile Ile Val Pro Glu Gln Thr Ile Glu Ile Pro Ser Ile Lys
1               5                   10                  15

Phe Ser Val Pro
            20

<210> SEQ ID NO 257
<211> LENGTH: 20
<212> TYPE: PRT
<213> ORGANISM: Artificial Sequence

```
<220> FEATURE:
<223> OTHER INFORMATION: Synthetic peptide

<400> SEQUENCE: 257

Lys Phe Ser Val Pro Ala Gly Ile Val Ile Pro Ser Phe Gln Ala Leu
1               5                   10                  15

Thr Ala Arg Phe
            20

<210> SEQ ID NO 258
<211> LENGTH: 20
<212> TYPE: PRT
<213> ORGANISM: Artificial Sequence
<220> FEATURE:
<223> OTHER INFORMATION: Synthetic peptide

<400> SEQUENCE: 258

Leu Thr Ala Arg Phe Glu Val Asp Ser Pro Val Tyr Asn Ala Thr Trp
1               5                   10                  15

Ser Ala Ser Leu
            20

<210> SEQ ID NO 259
<211> LENGTH: 20
<212> TYPE: PRT
<213> ORGANISM: Artificial Sequence
<220> FEATURE:
<223> OTHER INFORMATION: Synthetic peptide

<400> SEQUENCE: 259

Trp Ser Ala Ser Leu Lys Asn Lys Ala Asp Tyr Val Glu Thr Val Leu
1               5                   10                  15

Asp Ser Thr Cys
            20

<210> SEQ ID NO 260
<211> LENGTH: 20
<212> TYPE: PRT
<213> ORGANISM: Artificial Sequence
<220> FEATURE:
<223> OTHER INFORMATION: Synthetic peptide

<400> SEQUENCE: 260

Leu Asp Ser Thr Cys Ser Ser Thr Val Gln Phe Leu Glu Tyr Glu Leu
1               5                   10                  15

Asn Val Leu Gly
            20

<210> SEQ ID NO 261
<211> LENGTH: 20
<212> TYPE: PRT
<213> ORGANISM: Artificial Sequence
<220> FEATURE:
<223> OTHER INFORMATION: Synthetic peptide

<400> SEQUENCE: 261

Leu Asn Val Leu Gly Thr His Lys Ile Glu Asp Gly Thr Leu Ala Ser
1               5                   10                  15

Lys Thr Lys Gly
            20

<210> SEQ ID NO 262
<211> LENGTH: 20
<212> TYPE: PRT
```

<213> ORGANISM: Artificial Sequence
<220> FEATURE:
<223> OTHER INFORMATION: Synthetic peptide

<400> SEQUENCE: 262

Ser Lys Thr Lys Gly Thr Leu Ala His Arg Asp Phe Ser Ala Glu Tyr
1               5                   10                  15

Glu Glu Asp Gly
            20

<210> SEQ ID NO 263
<211> LENGTH: 20
<212> TYPE: PRT
<213> ORGANISM: Artificial Sequence
<220> FEATURE:
<223> OTHER INFORMATION: Synthetic peptide

<400> SEQUENCE: 263

Tyr Glu Glu Asp Gly Lys Phe Glu Gly Leu Gln Glu Trp Glu Gly Lys
1               5                   10                  15

Ala His Leu Asn
            20

<210> SEQ ID NO 264
<211> LENGTH: 20
<212> TYPE: PRT
<213> ORGANISM: Artificial Sequence
<220> FEATURE:
<223> OTHER INFORMATION: Synthetic peptide

<400> SEQUENCE: 264

Lys Ala His Leu Asn Ile Lys Ser Pro Ala Phe Thr Asp Leu His Leu
1               5                   10                  15

Arg Tyr Gln Lys
            20

<210> SEQ ID NO 265
<211> LENGTH: 20
<212> TYPE: PRT
<213> ORGANISM: Artificial Sequence
<220> FEATURE:
<223> OTHER INFORMATION: Synthetic peptide

<400> SEQUENCE: 265

Leu Arg Tyr Gln Lys Asp Lys Lys Gly Ile Ser Thr Ser Ala Ala Ser
1               5                   10                  15

Pro Ala Val Gly
            20

<210> SEQ ID NO 266
<211> LENGTH: 20
<212> TYPE: PRT
<213> ORGANISM: Artificial Sequence
<220> FEATURE:
<223> OTHER INFORMATION: Synthetic peptide

<400> SEQUENCE: 266

Ser Pro Ala Val Gly Thr Val Gly Met Asp Met Asp Glu Asp Asp
1               5                   10                  15

Phe Ser Lys Trp
            20

<210> SEQ ID NO 267
<211> LENGTH: 20

<212> TYPE: PRT
<213> ORGANISM: Artificial Sequence
<220> FEATURE:
<223> OTHER INFORMATION: Synthetic peptide

<400> SEQUENCE: 267

Asp Phe Ser Lys Trp Asn Phe Tyr Tyr Ser Pro Gln Ser Ser Pro Asp
1               5                   10                  15

Lys Lys Leu Thr
            20

<210> SEQ ID NO 268
<211> LENGTH: 20
<212> TYPE: PRT
<213> ORGANISM: Artificial Sequence
<220> FEATURE:
<223> OTHER INFORMATION: Synthetic peptide

<400> SEQUENCE: 268

Asp Lys Lys Leu Thr Ile Phe Lys Thr Glu Leu Arg Val Arg Glu Ser
1               5                   10                  15

Asp Glu Glu Thr
            20

<210> SEQ ID NO 269
<211> LENGTH: 20
<212> TYPE: PRT
<213> ORGANISM: Artificial Sequence
<220> FEATURE:
<223> OTHER INFORMATION: Synthetic peptide

<400> SEQUENCE: 269

Ser Asp Glu Glu Thr Gln Ile Lys Val Asn Trp Glu Glu Ala Ala
1               5                   10                  15

Ser Gly Leu Leu
            20

<210> SEQ ID NO 270
<211> LENGTH: 20
<212> TYPE: PRT
<213> ORGANISM: Artificial Sequence
<220> FEATURE:
<223> OTHER INFORMATION: Synthetic peptide

<400> SEQUENCE: 270

Ala Ser Gly Leu Leu Thr Ser Leu Lys Asp Asn Val Pro Lys Ala Thr
1               5                   10                  15

Gly Val Leu Tyr
            20

<210> SEQ ID NO 271
<211> LENGTH: 20
<212> TYPE: PRT
<213> ORGANISM: Artificial Sequence
<220> FEATURE:
<223> OTHER INFORMATION: Synthetic peptide

<400> SEQUENCE: 271

Thr Gly Val Leu Tyr Asp Tyr Val Asn Lys Tyr His Trp Glu His Thr
1               5                   10                  15

Gly Leu Thr Leu
            20

<210> SEQ ID NO 272

```
<211> LENGTH: 20
<212> TYPE: PRT
<213> ORGANISM: Artificial Sequence
<220> FEATURE:
<223> OTHER INFORMATION: Synthetic peptide

<400> SEQUENCE: 272

Thr Gly Leu Thr Leu Arg Glu Val Ser Ser Lys Leu Arg Arg Asn Leu
1               5                   10                  15

Gln Asn Asn Ala
            20

<210> SEQ ID NO 273
<211> LENGTH: 20
<212> TYPE: PRT
<213> ORGANISM: Artificial Sequence
<220> FEATURE:
<223> OTHER INFORMATION: Synthetic peptide

<400> SEQUENCE: 273

Leu Gln Asn Asn Ala Glu Trp Val Tyr Gln Gly Ala Ile Arg Gln Ile
1               5                   10                  15

Asp Asp Ile Asp
            20

<210> SEQ ID NO 274
<211> LENGTH: 20
<212> TYPE: PRT
<213> ORGANISM: Artificial Sequence
<220> FEATURE:
<223> OTHER INFORMATION: Synthetic peptide

<400> SEQUENCE: 274

Ile Asp Asp Ile Asp Val Arg Phe Gln Lys Ala Ala Ser Gly Thr Thr
1               5                   10                  15

Gly Thr Tyr Gln
            20

<210> SEQ ID NO 275
<211> LENGTH: 20
<212> TYPE: PRT
<213> ORGANISM: Artificial Sequence
<220> FEATURE:
<223> OTHER INFORMATION: Synthetic peptide

<400> SEQUENCE: 275

Thr Gly Thr Tyr Gln Glu Trp Lys Asp Lys Ala Gln Asn Leu Tyr Gln
1               5                   10                  15

Glu Leu Leu Thr
            20

<210> SEQ ID NO 276
<211> LENGTH: 20
<212> TYPE: PRT
<213> ORGANISM: Artificial Sequence
<220> FEATURE:
<223> OTHER INFORMATION: Synthetic peptide

<400> SEQUENCE: 276

Gln Glu Leu Leu Thr Gln Glu Gly Gln Ala Ser Phe Gln Gly Leu Lys
1               5                   10                  15

Asp Asn Val Phe
            20
```

<210> SEQ ID NO 277
<211> LENGTH: 20
<212> TYPE: PRT
<213> ORGANISM: Artificial Sequence
<220> FEATURE:
<223> OTHER INFORMATION: Synthetic peptide

<400> SEQUENCE: 277

```
Lys Asp Asn Val Phe Asp Gly Leu Val Arg Val Thr Gln Lys Phe His
1               5                   10                  15
Met Lys Val Lys
            20
```

<210> SEQ ID NO 278
<211> LENGTH: 20
<212> TYPE: PRT
<213> ORGANISM: Artificial Sequence
<220> FEATURE:
<223> OTHER INFORMATION: Synthetic peptide

<400> SEQUENCE: 278

```
His Met Lys Val Lys His Leu Ile Asp Ser Leu Ile Asp Phe Leu Asn
1               5                   10                  15
Phe Pro Arg Phe
            20
```

<210> SEQ ID NO 279
<211> LENGTH: 20
<212> TYPE: PRT
<213> ORGANISM: Artificial Sequence
<220> FEATURE:
<223> OTHER INFORMATION: Synthetic peptide

<400> SEQUENCE: 279

```
Asn Phe Pro Arg Phe Gln Phe Pro Gly Lys Pro Gly Ile Tyr Thr Arg
1               5                   10                  15
Glu Glu Leu Cys
            20
```

<210> SEQ ID NO 280
<211> LENGTH: 20
<212> TYPE: PRT
<213> ORGANISM: Artificial Sequence
<220> FEATURE:
<223> OTHER INFORMATION: Synthetic peptide

<400> SEQUENCE: 280

```
Arg Glu Glu Leu Cys Thr Met Phe Ile Arg Glu Val Gly Thr Val Leu
1               5                   10                  15
Ser Gln Val Tyr
            20
```

<210> SEQ ID NO 281
<211> LENGTH: 20
<212> TYPE: PRT
<213> ORGANISM: Artificial Sequence
<220> FEATURE:
<223> OTHER INFORMATION: Synthetic peptide

<400> SEQUENCE: 281

```
Leu Ser Gln Val Tyr Ser Lys Val His Asn Gly Ser Glu Ile Leu Phe
1               5                   10                  15
Ser Tyr Phe Gln
            20
```

```
<210> SEQ ID NO 282
<211> LENGTH: 20
<212> TYPE: PRT
<213> ORGANISM: Artificial Sequence
<220> FEATURE:
<223> OTHER INFORMATION: Synthetic peptide

<400> SEQUENCE: 282

Phe Ser Tyr Phe Gln Asp Leu Val Ile Thr Leu Pro Phe Glu Leu Arg
1               5                   10                  15

Lys His Lys Leu
            20

<210> SEQ ID NO 283
<211> LENGTH: 20
<212> TYPE: PRT
<213> ORGANISM: Artificial Sequence
<220> FEATURE:
<223> OTHER INFORMATION: Synthetic peptide

<400> SEQUENCE: 283

Arg Lys His Lys Leu Ile Asp Val Ile Ser Met Tyr Arg Glu Leu Leu
1               5                   10                  15

Lys Asp Leu Ser
            20

<210> SEQ ID NO 284
<211> LENGTH: 20
<212> TYPE: PRT
<213> ORGANISM: Artificial Sequence
<220> FEATURE:
<223> OTHER INFORMATION: Synthetic peptide

<400> SEQUENCE: 284

Leu Lys Asp Leu Ser Lys Glu Ala Gln Glu Val Phe Lys Ala Ile Gln
1               5                   10                  15

Ser Leu Lys Thr
            20

<210> SEQ ID NO 285
<211> LENGTH: 20
<212> TYPE: PRT
<213> ORGANISM: Artificial Sequence
<220> FEATURE:
<223> OTHER INFORMATION: Synthetic peptide

<400> SEQUENCE: 285

Gln Ser Leu Lys Thr Thr Glu Val Leu Arg Asn Leu Gln Asp Leu Leu
1               5                   10                  15

Gln Phe Ile Phe
            20

<210> SEQ ID NO 286
<211> LENGTH: 20
<212> TYPE: PRT
<213> ORGANISM: Artificial Sequence
<220> FEATURE:
<223> OTHER INFORMATION: Synthetic peptide

<400> SEQUENCE: 286

Leu Gln Phe Ile Phe Gln Leu Ile Glu Asp Asn Ile Lys Gln Leu Lys
1               5                   10                  15

Glu Met Lys Phe
            20
```

-continued

```
<210> SEQ ID NO 287
<211> LENGTH: 20
<212> TYPE: PRT
<213> ORGANISM: Artificial Sequence
<220> FEATURE:
<223> OTHER INFORMATION: Synthetic peptide

<400> SEQUENCE: 287

Lys Glu Met Lys Phe Thr Tyr Leu Ile Asn Tyr Ile Gln Asp Glu Ile
1               5                   10                  15

Asn Thr Ile Phe
            20

<210> SEQ ID NO 288
<211> LENGTH: 20
<212> TYPE: PRT
<213> ORGANISM: Artificial Sequence
<220> FEATURE:
<223> OTHER INFORMATION: Synthetic peptide

<400> SEQUENCE: 288

Ile Asn Thr Ile Phe Asn Asp Tyr Ile Pro Tyr Val Phe Lys Leu Leu
1               5                   10                  15

Lys Glu Asn Leu
            20

<210> SEQ ID NO 289
<211> LENGTH: 20
<212> TYPE: PRT
<213> ORGANISM: Artificial Sequence
<220> FEATURE:
<223> OTHER INFORMATION: Synthetic peptide

<400> SEQUENCE: 289

Leu Lys Glu Asn Leu Cys Leu Asn Leu His Lys Phe Asn Glu Phe Ile
1               5                   10                  15

Gln Asn Glu Leu
            20

<210> SEQ ID NO 290
<211> LENGTH: 20
<212> TYPE: PRT
<213> ORGANISM: Artificial Sequence
<220> FEATURE:
<223> OTHER INFORMATION: Synthetic peptide

<400> SEQUENCE: 290

Ile Gln Asn Glu Leu Gln Glu Ala Ser Gln Glu Leu Gln Gln Ile His
1               5                   10                  15

Gln Tyr Ile Met
            20

<210> SEQ ID NO 291
<211> LENGTH: 20
<212> TYPE: PRT
<213> ORGANISM: Artificial Sequence
<220> FEATURE:
<223> OTHER INFORMATION: Synthetic peptide

<400> SEQUENCE: 291

His Gln Tyr Ile Met Ala Leu Arg Glu Glu Tyr Phe Asp Pro Ser Ile
1               5                   10                  15

Val Gly Trp Thr
            20
```

```
<210> SEQ ID NO 292
<211> LENGTH: 20
<212> TYPE: PRT
<213> ORGANISM: Artificial Sequence
<220> FEATURE:
<223> OTHER INFORMATION: Synthetic peptide

<400> SEQUENCE: 292

Ile Val Gly Trp Thr Val Lys Tyr Tyr Glu Leu Glu Glu Lys Ile Val
1               5                   10                  15

Ser Leu Ile Lys
            20

<210> SEQ ID NO 293
<211> LENGTH: 20
<212> TYPE: PRT
<213> ORGANISM: Artificial Sequence
<220> FEATURE:
<223> OTHER INFORMATION: Synthetic peptide

<400> SEQUENCE: 293

Val Ser Leu Ile Lys Asn Leu Leu Val Ala Leu Lys Asp Phe His Ser
1               5                   10                  15

Glu Tyr Ile Val
            20

<210> SEQ ID NO 294
<211> LENGTH: 20
<212> TYPE: PRT
<213> ORGANISM: Artificial Sequence
<220> FEATURE:
<223> OTHER INFORMATION: Synthetic peptide

<400> SEQUENCE: 294

Ser Glu Tyr Ile Val Ser Ala Ser Asn Phe Thr Ser Gln Leu Ser Ser
1               5                   10                  15

Gln Val Glu Gln
            20

<210> SEQ ID NO 295
<211> LENGTH: 20
<212> TYPE: PRT
<213> ORGANISM: Artificial Sequence
<220> FEATURE:
<223> OTHER INFORMATION: Synthetic peptide

<400> SEQUENCE: 295

Ser Gln Val Glu Gln Phe Leu His Arg Asn Ile Gln Glu Tyr Leu Ser
1               5                   10                  15

Ile Leu Thr Asp
            20

<210> SEQ ID NO 296
<211> LENGTH: 20
<212> TYPE: PRT
<213> ORGANISM: Artificial Sequence
<220> FEATURE:
<223> OTHER INFORMATION: Synthetic peptide

<400> SEQUENCE: 296

Ser Ile Leu Thr Asp Pro Asp Gly Lys Gly Lys Glu Lys Ile Ala Glu
1               5                   10                  15

Leu Ser Ala Thr
            20
```

```
<210> SEQ ID NO 297
<211> LENGTH: 20
<212> TYPE: PRT
<213> ORGANISM: Artificial Sequence
<220> FEATURE:
<223> OTHER INFORMATION: Synthetic peptide

<400> SEQUENCE: 297

Glu Leu Ser Ala Thr Ala Gln Glu Ile Ile Lys Ser Gln Ala Ile Ala
1               5                   10                  15

Thr Lys Lys Ile
            20

<210> SEQ ID NO 298
<211> LENGTH: 20
<212> TYPE: PRT
<213> ORGANISM: Artificial Sequence
<220> FEATURE:
<223> OTHER INFORMATION: Synthetic peptide

<400> SEQUENCE: 298

Thr Lys Lys Ile Ile Ser Asp Tyr His Gln Gln Phe Arg Tyr Lys Leu
1               5                   10                  15

Gln Asp Phe Ser
            20

<210> SEQ ID NO 299
<211> LENGTH: 20
<212> TYPE: PRT
<213> ORGANISM: Artificial Sequence
<220> FEATURE:
<223> OTHER INFORMATION: Synthetic peptide

<400> SEQUENCE: 299

Leu Gln Asp Phe Ser Asp Gln Leu Ser Asp Tyr Tyr Glu Lys Phe Ile
1               5                   10                  15

Ala Glu Ser Lys
            20

<210> SEQ ID NO 300
<211> LENGTH: 20
<212> TYPE: PRT
<213> ORGANISM: Artificial Sequence
<220> FEATURE:
<223> OTHER INFORMATION: Synthetic peptide

<400> SEQUENCE: 300

Ile Ala Glu Ser Lys Arg Leu Ile Asp Leu Ser Ile Gln Asn Tyr His
1               5                   10                  15

Thr Phe Leu Ile
            20

<210> SEQ ID NO 301
<211> LENGTH: 20
<212> TYPE: PRT
<213> ORGANISM: Artificial Sequence
<220> FEATURE:
<223> OTHER INFORMATION: Synthetic peptide

<400> SEQUENCE: 301

His Thr Phe Leu Ile Tyr Ile Thr Glu Leu Leu Lys Lys Leu Gln Ser
1               5                   10                  15

Thr Thr Val Met
            20
```

```
<210> SEQ ID NO 302
<211> LENGTH: 20
<212> TYPE: PRT
<213> ORGANISM: Artificial Sequence
<220> FEATURE:
<223> OTHER INFORMATION: Synthetic peptide

<400> SEQUENCE: 302

Ser Thr Thr Val Met Asn Pro Tyr Met Lys Leu Ala Pro Gly Glu Leu
1               5                   10                  15

Thr Ile Ile Leu
            20
```